US012416030B2

(12) United States Patent
Papadakis

(10) Patent No.: US 12,416,030 B2
(45) Date of Patent: Sep. 16, 2025

(54) IDENTIFICATION OF AN α-1,2-FUCOSYLTRANSFERASE FOR THE IN VIVO PRODUCTION OF PURE LNFP-I

(71) Applicant: DSM IP Assets B.V., Heerlen (DK)

(72) Inventor: Manos Papadakis, Hørsholm (DK)

(73) Assignee: DSM IP Assets B.V., Heerlen (DK)

( * ) Notice: Subject to any disclaimer, the term of this patent is extended or adjusted under 35 U.S.C. 154(b) by 0 days.

(21) Appl. No.: 18/561,170

(22) PCT Filed: May 17, 2022

(86) PCT No.: PCT/EP2022/063315

§ 371 (c)(1),
(2) Date: Nov. 15, 2023

(87) PCT Pub. No.: WO2022/243312

PCT Pub. Date: Nov. 24, 2022

(65) Prior Publication Data

US 2024/0417766 A1 Dec. 19, 2024

(30) Foreign Application Priority Data

May 17, 2021 (DK) ............................ PA202170250

(51) Int. Cl.

| | |
|---|---|
| ***C12P 19/04*** | (2006.01) |
| ***C12N 1/20*** | (2006.01) |
| ***C12N 9/10*** | (2006.01) |
| ***C12N 9/26*** | (2006.01) |
| ***C12N 15/70*** | (2006.01) |
| ***C12P 19/18*** | (2006.01) |
| ***C12R 1/19*** | (2006.01) |

(52) U.S. Cl.

CPC ................ *C12P 19/04* (2013.01); *C12N 1/20* (2013.01); *C12N 9/1051* (2013.01); *C12N 9/2431* (2013.01); *C12N 15/70* (2013.01); *C12P 19/18* (2013.01); *C12R 2001/19* (2021.05); *C12Y 204/01122* (2013.01); *C12Y 204/01146* (2013.01); *C12Y 302/01026* (2013.01)

(58) Field of Classification Search

CPC . C12P 19/04; C12P 19/18; C12N 1/20; C12N 9/1051; C12N 9/2431; C12N 15/70; C12N 9/1048; C12N 15/09; C12R 2001/19; C12Y 204/01122; C12Y 204/01146; C12Y 302/01026; C12Y 204/01069; C07H 3/06

See application file for complete search history.

(56) References Cited

U.S. PATENT DOCUMENTS

| | | | |
|---|---|---|---|
| 11,608,504 B2 * | 3/2023 | Pedersen ................ | C12N 15/67 |
| 2012/0121772 A1 | 5/2012 | Bijl et al. | |
| 2016/0333042 A1 | 11/2016 | Jennewein | |
| 2017/0081353 A1 | 3/2017 | McCoy et al. | |
| 2020/0205430 A1 | 7/2020 | Owens | |
| 2021/0102216 A1 * | 4/2021 | Pedersen ................ | C12N 15/11 |

FOREIGN PATENT DOCUMENTS

| | | | |
|---|---|---|---|
| CN | 110669747 A * | 1/2020 | |
| DK | 202170250 | 11/2022 | |
| DK | 181242 | 5/2023 | |
| EP | 2927316 | 10/2015 | |
| EP | 3315610 | 5/2018 | |
| EP | 3425052 | 1/2019 | |
| EP | 3569713 | 11/2019 | |
| WO | WO 2010142305 | 12/2010 | |
| WO | WO 2012112777 | 8/2012 | |
| WO | WO 2015188834 | 12/2015 | |
| WO | WO 2015197082 | 12/2015 | |
| WO | WO 2016040531 | 3/2016 | |
| WO | WO 2017042382 | 3/2017 | |
| WO | WO 2017152918 | 9/2017 | |
| WO | WO 2017182965 | 10/2017 | |
| WO | WO 2018178271 | 10/2018 | |
| WO | WO 2019008133 | 1/2019 | |
| WO | WO 2019123324 | 6/2019 | |
| WO | WO 2020058251 | 3/2020 | |
| WO | WO 2020255054 | 12/2020 | |
| WO | WO-2020255054 A1 * | 12/2020 | ........... C12N 15/113 |
| WO | WO-2021148620 A1 * | 7/2021 | ............... C07H 3/06 |

OTHER PUBLICATIONS

K Singh, Raushan, et al. "Protein engineering approaches in the post-genomic era." Current Protein and Peptide Science 19.1 (2018): 5-15. (Year: 2018).*

Zhang, Meiling, David A. Case, and Jeffrey W. Peng. "Propagated perturbations from a peripheral mutation show interactions supporting WW domain thermostability." Structure 26.11 (2018): 1474-1485 (Year: 2018).*

Accession No. WP 126455392.1, Apr. 13, 2019, cited on IDS filed Jan. 30, 2024) {herein GenBank WP_126455392} (Year: 2019).*

Hao et al (2020, Date Published Nov. 6, 2020, JBC Research Article, https://doi.org/10.1074/jbc.RA120.015306) {herein Hao}. (Year: 2020).*

Hisaya et al (Date Issued: Sep. 1, 2016, Hokkaido University Collection of Scholarly and Academic Papers : HUSCAP, doi.org/10.1099/ijsem.0.001227) {herein Hisaya). (Year: 2016).*

Feng et al. (Machine Translated CN110669747A Jan. 10, 2020) {examiner cited) (Year: 2020).*

Altschul et al. Nucl. Acids Res. (1997) 25, 3389.

Gebus et al. Carbohydrate Research (2012) 363: 83-90.

(Continued)

*Primary Examiner* — Anand U Desai
*Assistant Examiner* — Erica Nicole Jones-Foster
(74) *Attorney, Agent, or Firm* — Neal, Gerber & Eisenberg LLP

(57) ABSTRACT

The present disclosure discloses the identification and introduction of a specific heterologous gene (denoted as smob), which encodes an α-1,2-fucosyltransferase, into an LNT production strain to produce LNFP-I in particular.

The smob gene originates from the organism *Sulfuriflexus mobilis* (https://www.dsmz.de/collection/catalogue/details/culture/DSM-102939), which is a sulfur-oxidizing bacterium isolated from a brackish lake sediment.

19 Claims, 11 Drawing Sheets

Specification includes a Sequence Listing.

(56) References Cited

OTHER PUBLICATIONS

GenBank, "alpha-1,2-fucosyltransferase [Helicobacter pylori]", Accession No. WP_080473865.1, Mar. 28, 2017.
GenBank, "alpha-1,2-fucosyltransferase [Sideroxydans lithotrophicus]", Accession No. WP_013031010.1 , Dec. 9, 2016.
GenBank, "alpha-1,2-fucosyltransferase [Sulfuriflexus mobilis]", Accession No. WP_126455392.1, Apr. 13, 2019.
GenBank, "beta-fructofuranosidase protein [Arthrobacter globiformis]", Accession No. BAD18121.1, Aug. 3, 2004.
GenBank, "*E. coli* gene lacZ coding for beta-galactosidase (EC 3.2.1.23)", Accession No. V00296.1 (GI:41901), Jul. 26, 2016.
GenBank, "glycosyltransferase family 2 protein [Neisseria meningitidis]", Accession No. WP_033911473.1, Mar. 20, 2023.
GenBank, "Major facilitator superfamily MFS_1 [Yersinia bercovieri ATCC 43970]", Accession No. EEQ08298.1., Jun. 1, 2009.
GenBank, "MFS transporter [Rosenbergiella nectarea]", Accession No. WP_092672081.1., Aug. 26, 2023.
GenBank, "MFS transporter [Rouxiella badensis]", Accession No. WP_017489914.1., Aug. 30, 2023.
GenBank, "MULTISPECIES: Lacl family DNA-binding transcriptional regulator [Enterobacterales]", Accession No. WP_000851062.1, Aug. 27, 2023.
GenBank, "MULTISPECIES: MFS transporter [Pantoea]", Accession No. WP_048785139.1, Aug. 31, 2023.
GenBank, "MULTISPECIES: sucrose-6-phosphate hydrolase [Enterobacterales]", Accession No. WP_000056853, Jul. 28, 2019.
GenBank, "MULTISPECIES: sugar efflux transporter [Serratia]", Accession No. WP_060448169.1., Feb. 28, 2022.
GenBank, "sucrose porin [Klebsiella pneumoniae]", Accession No. CAA40657, Apr. 18, 2005.
GenBank, "sucrose-specific enzyme Ii [Klebsiella pneumoniae]", Accession No. CAA40658, Apr. 18, 2005.
GenBank, "sugar efflux transporter [Yersinia alsatica]", Accession No. WP 087817556.1, Aug. 9, 2023.
GenBank, "beta-(1,3)-galactyltransferase, partial [Helicobacter pylori]", Accession No. AEZ55696.1, Mar. 23, 2012.
GenBank, "glycosyl transferase LgtA [Neisseria gonorrhoeae NCCP11945]", Accession No. ACF31229.1, Jan. 31, 2014.
GenBank, "glycosyltransferase [*Escherichia coli*]", Accession No. WP_000582563.1, Oct. 2, 2023.
GenBank, "Iacto-N-neotetraose biosynthesis glycosyl transferase LgtA [Neisseria meningitidis MC58]", Accession No. AAF42258.1, Jan. 31, 2014.
GenBank, "*Streptococcus agalactiae* cpslbD, cpslbF, cpslbG, cpslbH, cpslbl, cpslbJ, cpslbK, cpslbL, neuB, neuC genes, complete cds", Accession No. AB050723.1, Jul. 14, 2016.
GenBank, "WO 2002088364-A/1: Beta-1,3-galactose transferase and DNA encoding the same", Accession No. BD182026.1, Aug. 5, 2014.
GenBank, "glycoside hydrolase family 32 protein [Avibacterium gallinarum]", Accession No. WP_103853210.1, Feb. 10, 2018.
H. H. Freeze and A. D. Elbein: Chapter 4: Glycosylation precursors, in: Essentials of Glycobiology, 2nd edition (Eds. A. Varki et al.), Cold Spring Harbour Laboratory Press (2009).
Herring et al. Gene, 2003, 311:153-163.
Herring et al. J. Bacteriol., 2004, 186: 2673-81.
Kojima and Fukui, "Sulfuriflexus mobilis", DSM 102939, 2016 https://www.dsmz.de/collection/catalogue/details/culture/DSM-102939.
Murphy, J Bacteriol. (1998); 180(8):2063-7.
Muyrers et al., EMBO Rep. (2000) 1(3): 239-243.
Needleman and Wunsch, J. Mol. Biol., 1970, 48: 443-453.
Petschacher et al. Biotechnological production of fucosylated human milk oligosaccharides: Prokaryotic fucosyltransferases and their use in biocatalytic cascades or whole cell conversion systems. J Biotechnol., 2016, 235:61-83.
Rice, et al. EMBOSS: The European Molecular Biology Open Software Suite, 2000, Trends Genet. 16: 276-277.
UniProt, "GDP-L-fucose synthase", Accession No. P32055, https://www.uniprot.org/uniprotkb/P32055/entry.
UniProt, "GDP-mannose 4,6-dehydratase", Accession No. P0AC88, https://www.uniprot.org/uniprotkb/P0AC88/entry.
UniProt, "GDP-mannose mannosyl hydrolase", Accession No. P32056, https://www.uniprot.org/uniprotkb/P32056/entry.
UniProt, "Mannose-1-phosphate guanylyltransferase", Accession No. P24174, https://www.uniprot.org/uniprotkb/P24174/entry.
UniProt, "Phosphomannomutase", Accession No. P24175, https://www.uniprot.org/uniprotkb/P24175/entry.
UniProt, "Putative colanic acid biosynthesis glycosyl transferase Wcal", Accession No. P32057, https://www.uniprot.org/uniprotkb/P32057/entry.
Vetcher et al. Appl Environ Microbiol., 2005 ;71(4):1829-35.
Waddell C.S. and Craig N.L., Genes Dev. (1988) 2(2):137-49.
Wang et al. Mol. Microbiol., 1999, 31, 1265-1274.
Warming et al. Nucleic Acids Res., 2005, 33(4): e36.
Wenzel et al. Chem Biol. (2005), 12(3):349-56.
Zhang et al. Nature Genetics (1998) 20: 123-128.
First Technical Examination Report for DK Application No. PA202170250, mailed Oct. 20, 2021, 8 pages.
Database EMBL-EBI/UNIPROTKB [online], 2020, "Alpha-1,2-fucosyltransferase", Accession No. A0A661R6E9.
Database EMBL-EBI/UNIPROTKB [online], 2018, "Sucrose-6-phosphate hydrolase (scrB) from Avibacterium gallinarum"; Accession No. A0A379AWT7.
Isono, N et al.: "Cloning and heterologous expression of a beta-fructofuranosidase gene from Arthrobacter globiformis IFO 3062, and site-directed mutagenesis of the essential aspartic acid and glutamic acid of the active site", J. Biosci. Bioeng., vol. 97, No. 4 2004, pp. 244-249.
Second Technical Examination Report for DK Application No. PA202170250, mailed Apr. 7, 2022, 3 pages.
Third Technical Examination Report for DK Application No. PA202170250, mailed Oct. 28, 2022, 2 pages.
Intention to Grant for DK Application No. PA202170250, mailed Nov. 30, 2022, 15 pages.
International Search Report and Written Opinion for International Patent Application No. , mailed, pages.
Sternowsky HJ et al, "Arsenic in breast milk during the first 3 months of lactation", International Journal of Hygiene and Environmental Health, Urban U. Fischer, Jena, DE , vol. 205, No. 5, Jan. 1, 2002 (Jan. 1, 2002), p. 405-409.
Andreas N.J. et al, "Human breast milk: A review on its composition and bioactivity", Early Human Development , vol. 91, No. 11, Nov. 1, 2015 (Nov. 1, 2015), p. 629-635.
Albermann C et al, "Synthesis of the milk oligosaccharide 2'-fucosyllactose using recombinant bacterial enzymes", Carbohydrate Research, Pergamon, GB , vol. 334, No. 2, Aug. 23, 2001 (Aug. 23, 2001), p. 97-103.
Granted claims for DK Patent Application No. PA202170250.

* cited by examiner

SEQUENCE LISTING

```
<160> NUMBER OF SEQ ID NOS: 42

<210> SEQ ID NO 1
<211> LENGTH: 292
<212> TYPE: PRT
<213> ORGANISM: Sulfuriflexus mobilis

<400> SEQUENCE: 1

Met Ile Ile Ser Gln Ile Ile Gly Gly Leu Gly Asn Gln Met Phe Gln
1               5                   10                  15

Tyr Ala Ala Gly Arg Ala Leu Ser Leu Val Arg Gly Gln Pro Leu Leu
            20                  25                  30

Leu Asp Val Thr Gly Phe Ala Gly Tyr Gly Leu His Gln Gly Phe Glu
        35                  40                  45

Leu Gln Arg Val Phe Asp Cys Pro Ile Gly Ile Ala Thr Glu Glu Asp
    50                  55                  60

Val Arg Gly Ile Leu Gly Trp Gln Phe Ser Ala Gly Ile Arg Arg Ile
65                  70                  75                  80
```

-continued

```
Val Ala Arg Pro Gly Met Ala Ala Phe Arg Arg Lys Gly Phe Ile Val
            85                  90                  95

Glu Pro His Phe His Tyr Trp Pro Glu Ile Lys Asn Val Pro Arg Asp
            100                 105                 110

Cys Tyr Leu Leu Gly Tyr Trp Gln Ser Glu Arg Tyr Phe Arg Ala Ala
        115                 120                 125

Thr Ala Asp Ile Arg Ala Asp Phe Ser Phe Lys Ser Pro Leu Val Asn
    130                 135                 140

Arg Asn Ala Glu Thr Ala Ala Gln Ile Asp Gln Val Asn Ala Ile Ser
145                 150                 155                 160

Leu His Met Arg Arg Gly Asp Tyr Val Asn Asn Pro Lys Thr Ser Ala
            165                 170                 175

Thr His Gly Leu Cys Ser Leu Asp Tyr Tyr Gln Ala Ala Ile Lys Phe
            180                 185                 190

Val Ser Glu Arg Val Glu Glu Pro Phe Phe Phe Ile Phe Ser Asp Asp
        195                 200                 205

Ile Ala Trp Val Lys Ala Asn Leu Lys Leu Asp Phe Pro Cys Gln Tyr
    210                 215                 220

Val Asp His Asn His Gly Ala Glu Ser Phe Asn Asp Met His Leu Met
225                 230                 235                 240

Ser Leu Cys Gln His His Ile Ile Ala Asn Ser Ser Phe Ser Trp Trp
            245                 250                 255

Gly Ala Trp Leu Asn Ser Asp Pro Lys Lys Ile Val Leu Ala Pro Lys
            260                 265                 270

Lys Trp Phe Ala Asn Lys Asn Asn Ile Lys Asp Leu Phe Pro Pro Gly
        275                 280                 285

Trp Val Ser Leu
    290


<210> SEQ ID NO 2
<211> LENGTH: 879
<212> TYPE: DNA
<213> ORGANISM: Artificial Sequence
<220> FEATURE:
<223> OTHER INFORMATION: Promoter sequence

<400> SEQUENCE: 2

atgatcatca gccagattat tggtggtctg ggtaatcaga tgtttcagta tgcagcaggt     60

cgtgcactga gcctggttcg tggtcagccg ctgctgctgg atgttaccgg ttttgcaggt    120

tatggtctgc atcagggttt tgaactgcag cgtgtttttg attgtccgat tggtattgca    180

accgaagaag atgttcgcgg tattttaggt tggcagttta gcgcaggtat tcgtcgtatt    240

gttgcacgtc ctggtatggc agcatttcgt cgtaaaggtt ttattgtgga accgcacttt    300

cattattggc ctgagattaa aaacgttccg cgtgattgtt atctgcttgg ttattggcag    360

agcgaacgtt attttcgtgc agcaaccgca gatattcgtg cagatttttc atttaaaagt    420

ccgctggtta atcgcaatgc cgaaaccgca gcacagattg atcaggttaa tgcaattagc    480

ctgcatatgc gtcgtggtga ttatgtgaat aatccgaaaa ccagcgcaac ccatggtctg    540

tgtagcctgg attattatca ggcagcaatc aaatttgtta gcgaacgtgt tgaagaaccg    600

tttttcttta tcttctccga tgatattgca tgggtgaaag caaatctgaa actggatttt    660

ccgtgccagt atgtggatca taatcatggt gcagaaagct tcaatgatat gcatctgatg    720

agcctgtgtc agcatcatat tattgcaaac agcagcttta gttggtgggg tgcatggctg    780

aatagcgatc cgaaaaaaat cgttctggca ccgaaaaaat ggttcgccaa caaaaacaac    840
```

-continued atcaaagacc tgtttccgcc tggttgggtt agcctgtaa 879

<210> SEQ ID NO 3
<211> LENGTH: 387
<212> TYPE: PRT
<213> ORGANISM: Rouxiella badensis

<400> SEQUENCE: 3

```
Met Ser Ser Arg Arg Leu Ser Ile Ile Phe Ala Thr Phe Leu Leu Val
1               5                   10                  15

Ser Phe Leu Thr Gly Ile Ala Gly Ala Leu Gln Ala Pro Thr Leu Ser
            20                  25                  30

Leu Phe Leu Thr Asn Glu Val Lys Val Arg Pro Leu Trp Val Gly Leu
        35                  40                  45

Phe Tyr Thr Val Asn Ala Leu Gly Gly Ile Val Ile Ser Phe Leu Leu
    50                  55                  60

Ala Asn Tyr Ser Asp Lys Lys Gly Asp Arg Arg Lys Leu Leu Phe Phe
65                  70                  75                  80

Cys Thr Leu Met Ala Ile Gly Asn Ser Leu Ile Phe Ala Tyr Ser Arg
                85                  90                  95

Asp Tyr Leu Val Leu Ile Ser Val Gly Val Leu Leu Ala Ala Ile Gly
            100                 105                 110

Asn Ala Ser Met Pro Gln Leu Phe Ala Leu Ala Arg Glu Tyr Ala Asp
        115                 120                 125

Arg Ser Ala His Glu Val Val Met Phe Ser Ser Met Met Arg Ala Thr
    130                 135                 140

Leu Ser Leu Ala Trp Val Leu Gly Pro Pro Ile Ser Phe Thr Leu Ala
145                 150                 155                 160

Leu Asn Tyr Gly Phe Thr Leu Met Tyr Leu Cys Ala Ala Gly Val Phe
                165                 170                 175

Ile Phe Ser Ala Leu Met Val Trp Phe Phe Leu Pro Ser Val Gly Arg
            180                 185                 190

Ile Glu Gln Pro Val Asp Lys Val Val Val His Val Ser Ala Trp Lys
        195                 200                 205

Asn Arg Asp Val Arg Leu Leu Phe Phe Ala Ser Leu Leu Met Trp Thr
    210                 215                 220

Cys Asn Ile Met Tyr Ile Ile Asp Met Pro Leu Tyr Ile Thr Ser Asp
225                 230                 235                 240

Leu Gly Leu Pro Glu Gly Leu Ala Gly Leu Leu Met Gly Ala Ala Ala
                245                 250                 255

Gly Leu Glu Ile Pro Val Met Leu Ile Ala Gly Tyr Leu Val Lys Arg
            260                 265                 270

Thr Gly Lys Arg Arg Leu Met Leu Cys Ala Ala Val Phe Gly Ile Leu
        275                 280                 285

Phe Tyr Leu Gly Leu Val Leu Phe Gln Phe Lys Ala Ala Leu Met Ile
    290                 295                 300

Leu Gln Leu Phe Asn Ala Ile Phe Ile Gly Ile Ile Ala Gly Ile Gly
305                 310                 315                 320

Met Leu Tyr Phe Gln Asp Leu Met Pro Gly Arg Ala Gly Ser Ala Thr
                325                 330                 335

Thr Leu Phe Thr Asn Ser Ile Ser Thr Gly Ala Ile Leu Ala Gly Val
            340                 345                 350

Ile Gln Gly Thr Ile Val Gln Asn Phe Gly His Tyr Gln Val Tyr Trp
        355                 360                 365
```

```
Met Ala Leu Ala Leu Ala Val Gly Ala Leu Val Leu Met Thr Arg Val
    370                 375                 380

Lys Asn Val
385


<210> SEQ ID NO 4
<211> LENGTH: 394
<212> TYPE: PRT
<213> ORGANISM: Rosenbergiella nectarea

<400> SEQUENCE: 4

Met Gln Ser Phe Thr Pro Pro Ala Pro Lys Gly Gly Asn Pro Val Phe
1               5                   10                  15

Met Met Phe Met Leu Val Thr Phe Phe Val Ser Ile Ala Gly Ala Leu
            20                  25                  30

Gln Ala Pro Thr Leu Ser Leu Tyr Leu Ser Gln Glu Leu Ala Ala Lys
        35                  40                  45

Pro Phe Met Val Gly Leu Phe Phe Thr Ile Asn Ala Val Thr Gly Ile
    50                  55                  60

Ile Ile Ser Phe Ile Leu Ala Lys Arg Ser Asp Arg Lys Gly Asp Arg
65                  70                  75                  80

Arg Arg Leu Leu Met Phe Cys Cys Ala Met Ala Ile Ala Asn Ala Leu
                85                  90                  95

Met Phe Ala Phe Val Arg Gln Tyr Val Val Leu Ile Thr Leu Gly Leu
            100                 105                 110

Ile Leu Ser Ala Leu Thr Ser Val Val Met Pro Gln Leu Phe Ala Leu
        115                 120                 125

Ala Arg Glu Tyr Ala Asp Arg Thr Gly Arg Glu Val Val Met Phe Ser
    130                 135                 140

Ser Val Met Arg Thr Gln Met Ser Leu Ala Trp Val Ile Gly Pro Pro
145                 150                 155                 160

Ile Ser Phe Ala Leu Ala Leu Asn Tyr Gly Phe Ile Thr Leu Tyr Leu
                165                 170                 175

Val Ala Ala Ala Leu Phe Leu Leu Ser Leu Ile Leu Ile Lys Thr Thr
            180                 185                 190

Leu Pro Ser Val Pro Arg Leu Tyr Pro Ala Glu Asp Leu Ala Lys Ser
        195                 200                 205

Ala Ala Ser Gly Trp Lys Arg Thr Asp Val Arg Phe Leu Phe Ala Ala
    210                 215                 220

Ser Val Leu Met Trp Val Cys Asn Leu Met Tyr Ile Ile Asp Met Pro
225                 230                 235                 240

Leu Tyr Ile Ser Lys Ser Leu Gly Met Pro Glu Ser Phe Ala Gly Val
                245                 250                 255

Leu Met Gly Thr Ala Ala Gly Leu Glu Ile Pro Val Met Leu Leu Ala
            260                 265                 270

Gly Tyr Leu Ala Lys Arg Val Gly Lys Arg Pro Leu Val Ile Val Ala
        275                 280                 285

Ala Val Cys Gly Leu Ala Phe Tyr Pro Ala Met Leu Val Phe His Gln
    290                 295                 300

Gln Thr Gly Leu Leu Ile Ile Gln Leu Leu Asn Ala Val Phe Ile Gly
305                 310                 315                 320

Ile Val Ala Gly Leu Val Met Leu Trp Phe Gln Asp Leu Met Pro Gly
                325                 330                 335

Lys Ala Gly Ala Ala Thr Thr Leu Phe Thr Asn Ser Val Ser Thr Gly
```

340 345 350

Met Ile Phe Ala Gly Leu Cys Gln Gly Leu Leu Ser Asp Leu Leu Gly
355 360 365

His Gln Ala Ile Tyr Val Leu Ala Thr Val Leu Met Val Ile Ala Leu
370 375 380

Leu Leu Leu Leu Arg Val Lys Glu Gln Ala
385 390

<210> SEQ ID NO 5
<211> LENGTH: 393
<212> TYPE: PRT
<213> ORGANISM: Yersinia bercovieri

<400> SEQUENCE: 5

Met Lys Ser Ala Leu Thr Phe Ser Arg Arg Ile Asn Pro Val Phe Leu
1 5 10 15

Ala Phe Phe Val Val Ala Phe Leu Ser Gly Ile Ala Gly Ala Leu Gln
20 25 30

Ala Pro Thr Leu Ser Leu Phe Leu Ser Thr Glu Val Lys Val Arg Pro
35 40 45

Leu Trp Val Gly Leu Phe Tyr Thr Val Asn Ala Ile Ala Gly Ile Thr
50 55 60

Val Ser Phe Ile Leu Ala Lys Arg Ser Asp Ser Arg Gly Asp Arg Arg
65 70 75 80

Lys Leu Ile Met Val Cys Tyr Leu Met Ala Val Gly Asn Cys Leu Leu
85 90 95

Phe Ala Phe Asn Arg Asp Tyr Leu Thr Leu Ile Thr Ala Gly Val Leu
100 105 110

Leu Ala Ser Val Ala Asn Thr Ala Met Pro Gln Ile Phe Ala Leu Ala
115 120 125

Arg Glu Tyr Ala Asp Ser Ser Ala Arg Glu Val Val Met Phe Ser Ser
130 135 140

Ile Met Arg Ala Gln Leu Ser Leu Ala Trp Val Ile Gly Pro Pro Leu
145 150 155 160

Ser Phe Met Leu Ala Leu Asn Tyr Gly Phe Thr Leu Met Phe Ser Ile
165 170 175

Ala Ala Gly Ile Phe Val Leu Ser Ala Leu Val Val Trp Phe Ile Leu
180 185 190

Pro Ser Val Pro Arg Ala Glu Pro Val Val Asp Ala Pro Val Val Val
195 200 205

Gln Gly Ser Leu Phe Ala Asp Lys Asn Val Leu Leu Leu Phe Ile Ala
210 215 220

Ser Met Leu Met Trp Thr Cys Asn Thr Met Tyr Ile Ile Asp Met Pro
225 230 235 240

Leu Tyr Ile Thr Ala Ser Leu Gly Leu Pro Glu Arg Leu Ala Gly Leu
245 250 255

Leu Met Gly Thr Ala Ala Gly Leu Glu Ile Pro Ile Met Leu Leu Ala
260 265 270

Gly Tyr Ser Val Arg Tyr Phe Gly Lys Arg Lys Ile Met Leu Phe Ala
275 280 285

Val Leu Ala Gly Val Leu Phe Tyr Thr Gly Leu Val Leu Phe Lys Phe
290 295 300

Lys Thr Ala Leu Met Leu Leu Gln Ile Phe Asn Ala Ile Phe Ile Gly
305 310 315 320

-continued

```
Ile Val Ala Gly Ile Gly Met Leu Tyr Phe Gln Asp Leu Met Pro Gly
                325                 330                 335

Arg Ala Gly Ala Ala Thr Thr Leu Phe Thr Asn Ser Ile Ser Thr Gly
            340                 345                 350

Val Ile Leu Ala Gly Val Leu Gln Gly Gly Leu Thr Glu Thr Trp Gly
        355                 360                 365

His Asp Ser Val Tyr Val Met Ala Met Val Leu Ser Ile Leu Ala Leu
    370                 375                 380

Ile Ile Cys Ala Arg Val Arg Glu Ala
385                 390


<210> SEQ ID NO 6
<211> LENGTH: 393
<212> TYPE: PRT
<213> ORGANISM: Yersinia frederiksenii

<400> SEQUENCE: 6

Met Lys Ser Ala Leu Thr Phe Ser Arg Arg Ile Asn Pro Val Phe Leu
1               5                   10                  15

Ala Phe Phe Val Val Ala Phe Leu Ser Gly Ile Ala Gly Ala Leu Gln
            20                  25                  30

Ala Pro Thr Leu Ser Leu Phe Leu Ser Thr Glu Val Lys Val Arg Pro
        35                  40                  45

Leu Trp Val Gly Leu Phe Tyr Thr Val Asn Ala Ile Ala Gly Ile Thr
    50                  55                  60

Val Ser Phe Val Leu Ala Lys Arg Ser Asp Leu Arg Gly Asp Arg Arg
65                  70                  75                  80

Lys Leu Ile Leu Val Cys Tyr Leu Met Ala Val Gly Asn Cys Leu Leu
                85                  90                  95

Phe Ala Phe Asn Arg Asp Tyr Leu Thr Leu Ile Thr Ala Gly Val Leu
            100                 105                 110

Leu Ala Ala Val Ala Asn Thr Ala Met Pro Gln Ile Phe Ala Leu Ala
        115                 120                 125

Arg Glu Tyr Ala Asp Asn Ser Ala Arg Glu Val Val Met Phe Ser Ser
    130                 135                 140

Ile Met Arg Ala Gln Leu Ser Leu Ala Trp Val Ile Gly Pro Pro Leu
145                 150                 155                 160

Ser Phe Met Leu Ala Leu Asn Tyr Gly Phe Thr Leu Met Phe Cys Ile
                165                 170                 175

Ala Ala Gly Ile Phe Val Leu Ser Ala Leu Val Val Trp Phe Ile Leu
            180                 185                 190

Pro Ser Val Gln Arg Ala Glu Pro Val Met Asp Ala Pro Thr Val Ala
        195                 200                 205

Gln Gly Ser Leu Phe Ala Asp Lys Asp Val Leu Leu Leu Phe Ile Ala
    210                 215                 220

Ser Met Leu Met Trp Thr Cys Asn Thr Met Tyr Ile Ile Asp Met Pro
225                 230                 235                 240

Leu Tyr Ile Thr Ala Ser Leu Gly Leu Pro Glu Arg Leu Ala Gly Leu
                245                 250                 255

Leu Met Gly Thr Ala Ala Gly Leu Glu Ile Pro Ile Met Leu Leu Ala
            260                 265                 270

Gly Tyr Ser Val Arg Arg Phe Gly Lys Arg Lys Ile Met Leu Phe Ala
        275                 280                 285

Val Leu Ala Gly Val Leu Phe Tyr Thr Gly Leu Val Leu Phe Lys Phe
    290                 295                 300
```

-continued

```
Lys Ser Ala Leu Met Leu Leu Gln Ile Phe Asn Ala Ile Phe Ile Gly
305                 310                 315                 320

Ile Val Ala Gly Ile Gly Met Leu Tyr Phe Gln Asp Leu Met Pro Gly
                325                 330                 335

Arg Ala Gly Ala Ala Thr Thr Leu Phe Thr Asn Ser Ile Ser Thr Gly
            340                 345                 350

Val Ile Leu Ala Gly Val Leu Gln Gly Val Leu Thr Glu Thr Trp Gly
        355                 360                 365

His Asn Ser Val Tyr Val Met Ala Met Ile Leu Ala Ile Leu Ser Leu
    370                 375                 380

Ile Ile Cys Ala Arg Val Arg Glu Ala
385                 390


<210> SEQ ID NO 7
<211> LENGTH: 392
<212> TYPE: PRT
<213> ORGANISM: Pantoea vagans

<400> SEQUENCE: 7

Met Lys Ser Leu Leu Thr Arg Lys Arg Arg Ile Asn Pro Val Phe Leu
1               5                   10                  15

Ala Phe Met Ala Ala Ser Phe Met Ile Gly Val Ala Gly Ala Leu Gln
            20                  25                  30

Ala Pro Thr Leu Ser Leu Phe Leu Thr Arg Glu Val Gln Ala Arg Pro
        35                  40                  45

Leu Trp Val Gly Leu Phe Phe Thr Val Asn Ala Ile Ala Gly Ile Val
    50                  55                  60

Val Ser Met Leu Val Ala Lys Arg Ser Asp Ser Arg Gly Asp Arg Arg
65                  70                  75                  80

Thr Leu Ile Leu Phe Cys Cys Ala Met Ala Phe Cys Asn Ala Leu Leu
                85                  90                  95

Phe Ala Phe Thr Arg His Tyr Leu Thr Leu Ile Thr Leu Gly Val Leu
            100                 105                 110

Leu Ser Ala Leu Ala Ser Val Ser Met Pro Gln Ile Phe Ala Leu Ala
        115                 120                 125

Arg Glu Tyr Ala Asp Gln Ser Ala Arg Glu Ala Val Met Phe Ser Ser
    130                 135                 140

Val Met Arg Ala Gln Leu Ser Leu Ala Trp Val Ile Gly Pro Pro Leu
145                 150                 155                 160

Ser Phe Ala Leu Ala Leu Asn Phe Gly Phe Val Thr Leu Phe Leu Val
                165                 170                 175

Ala Ala Ala Leu Phe Leu Val Cys Ile Leu Leu Ile Lys Phe Thr Leu
            180                 185                 190

Pro Ser Val Pro Arg Ala Glu Pro Leu Met Arg Ser Gly Gly Met Pro
        195                 200                 205

Leu Ser Gly Trp Arg Asp Arg Asp Val Arg Leu Leu Phe Ile Ala Ser
    210                 215                 220

Val Thr Met Trp Thr Cys Asn Thr Met Tyr Ile Ile Asp Met Pro Leu
225                 230                 235                 240

Tyr Ile Ser Val Thr Leu Gly Leu Pro Glu Lys Leu Ala Gly Leu Leu
                245                 250                 255

Met Gly Thr Ala Ala Gly Leu Glu Ile Pro Val Met Leu Leu Ala Gly
            260                 265                 270

His Tyr Ala Lys Arg Val Gly Lys Arg Asn Leu Met Leu Ile Ala Val
```

```
        275                 280                 285

Ala Ala Gly Val Leu Phe Tyr Ala Gly Leu Ala Met Phe Ala Ser Gln
    290                 295                 300

Thr Ala Leu Met Ala Leu Gln Leu Phe Asn Ala Val Phe Ile Gly Ile
305                 310                 315                 320

Ile Ala Gly Ile Gly Met Leu Trp Phe Gln Asp Leu Met Pro Gly Arg
                325                 330                 335

Pro Gly Ala Ala Thr Thr Met Phe Thr Asn Ser Ile Ser Thr Gly Met
            340                 345                 350

Ile Leu Ala Gly Val Ile Gln Gly Thr Leu Ser Glu Arg Phe Gly His
        355                 360                 365

Ile Ala Val Tyr Trp Leu Ala Leu Gly Leu Ala Val Ala Ala Phe Ala
    370                 375                 380

Met Ser Ala Arg Val Lys Asn Val
385                 390


<210> SEQ ID NO 8
<211> LENGTH: 398
<212> TYPE: PRT
<213> ORGANISM: Serratia marcescens

<400> SEQUENCE: 8

Met Gln Arg Leu Ser Arg Leu Ser Leu Arg Ile Asn Pro Ile Phe Ala
1               5                   10                  15

Ala Phe Leu Leu Ile Ala Phe Leu Ser Gly Ile Ala Gly Ala Leu Leu
            20                  25                  30

Thr Pro Thr Leu Ser Leu Phe Leu Thr Thr Glu Val Lys Val Arg Pro
        35                  40                  45

Leu Trp Val Gly Leu Phe Tyr Thr Ala Asn Ala Val Ala Gly Ile Val
    50                  55                  60

Val Ser Phe Leu Leu Ala Lys Arg Ser Asp Thr Arg Gly Asp Arg Arg
65                  70                  75                  80

Arg Leu Ile Leu Leu Cys Cys Leu Met Ala Val Gly Asn Cys Leu Leu
                85                  90                  95

Phe Ala Phe Asn Arg Asp Tyr Leu Thr Leu Ile Thr Ala Gly Val Leu
            100                 105                 110

Met Ser Ala Val Ala Asn Thr Ala Met Pro Gln Ile Phe Ala Leu Ala
        115                 120                 125

Arg Glu Tyr Ala Asp Ser Glu Ala Arg Glu Val Val Met Phe Ser Ser
    130                 135                 140

Val Met Arg Ala Gln Leu Ser Leu Ala Trp Val Ile Gly Pro Pro Leu
145                 150                 155                 160

Ser Phe Ala Leu Ala Leu Asn Tyr Gly Phe Thr Val Met Phe Leu Ile
                165                 170                 175

Ala Ala Val Thr Phe Ala Val Cys Val Leu Leu Val Gly Phe Met Leu
            180                 185                 190

Pro Ser Val Pro Arg Ala Ala Glu Asn Glu Gly Leu Gln Gly Gly Val
        195                 200                 205

Ser Ala Pro Ile Ala Pro Ala Ser Ala Trp Arg Asn Arg Asp Val Arg
    210                 215                 220

Leu Leu Phe Ile Ala Ser Met Leu Met Trp Thr Cys Asn Thr Leu Tyr
225                 230                 235                 240

Ile Ile Asp Met Pro Leu Tyr Ile Thr Ala Asp Leu Gly Leu Pro Glu
                245                 250                 255
```

-continued

```
Gly Leu Ala Gly Val Leu Met Gly Thr Ala Ala Gly Leu Glu Ile Pro
            260                 265                 270

Ala Met Leu Leu Ala Gly Tyr Tyr Val Lys Arg Phe Gly Lys Arg Asn
        275                 280                 285

Met Met Leu Leu Ala Val Val Ala Gly Val Leu Phe Tyr Leu Gly Leu
    290                 295                 300

Thr Val Leu Glu Ser Lys Pro Ala Leu Ile Ala Leu Gln Leu Leu Asn
305                 310                 315                 320

Ala Val Phe Ile Gly Ile Val Ala Gly Ile Gly Met Leu Tyr Phe Gln
                325                 330                 335

Asp Leu Met Pro Gly Arg Pro Gly Ala Ala Thr Thr Leu Phe Thr Asn
            340                 345                 350

Ser Ile Ser Thr Gly Val Ile Leu Ala Gly Val Leu Gln Gly Ala Leu
        355                 360                 365

Val Glu Asn Leu Gly His Gly Ser Val Tyr Trp Met Ala Ala Leu Leu
    370                 375                 380

Ala Leu Ala Ala Leu Gly Met Ser Ala Lys Val Arg Glu Val
385                 390                 395


<210> SEQ ID NO 9
<211> LENGTH: 505
<212> TYPE: PRT
<213> ORGANISM: Klebsiella pneumoniae

<400> SEQUENCE: 9

Met Tyr Lys Lys Arg Lys Leu Ala Ile Leu Ile Ala Leu Leu Thr Gly
1               5                   10                  15

Thr Ala Ala Ala His Gly Gln Thr Asp Leu Asn Ser Ile Glu Ala Arg
            20                  25                  30

Leu Ala Ala Leu Glu Lys Arg Leu Gln Asp Ala Glu Thr Arg Ala Ser
        35                  40                  45

Thr Ala Glu Ser Arg Ala Ala Ser Ala Glu Gln Lys Val Gln Gln Leu
    50                  55                  60

Thr Gln Gln Gln Gln Gln Thr Gln Ala Thr Thr Gln Gln Val Ala Arg
65                  70                  75                  80

Arg Thr Thr Gln Leu Glu Glu Lys Ala Glu Arg Pro Gly Gly Phe Glu
                85                  90                  95

Phe His Gly Tyr Ala Arg Ser Gly Val Ile Met Asn Asp Ser Ala Ala
            100                 105                 110

Ser Thr Lys Ser Gly Ala Tyr Met Thr Pro Ala Gly Glu Thr Gly Gly
        115                 120                 125

Ala Ile Gly Arg Leu Gly Asn Gln Ala Asp Thr Tyr Val Glu Met Asn
    130                 135                 140

Leu Glu His Lys Gln Thr Leu Asp Asn Gly Ala Thr Thr Arg Phe Lys
145                 150                 155                 160

Val Met Val Ala Asp Gly Gln Thr Thr Tyr Asn Asp Trp Thr Ala Ser
                165                 170                 175

Ser Ser Asp Leu Asn Val Arg Gln Ala Phe Val Glu Leu Gly Asn Leu
            180                 185                 190

Pro Thr Phe Glu Gly Pro Phe Lys Gly Ser Thr Leu Trp Ala Gly Lys
        195                 200                 205

Arg Phe Asp Arg Asp Asn Phe Asp Ile His Trp Ile Asp Ser Asp Val
    210                 215                 220

Val Phe Leu Ala Gly Thr Gly Gly Gly Ile Tyr Asp Val Lys Trp Asn
225                 230                 235                 240
```

-continued

```
Asp Ser Leu Arg Ser Asn Phe Ser Leu Tyr Gly Arg Asn Phe Gly Asp
                245                 250                 255

Ile Ala Asp Ser Ser Asn Ser Val Gln Asn Tyr Ile Val Ser Met Asn
            260                 265                 270

Asn Phe Ala Gly Pro Val Gln Met Met Val Ser Gly Met Arg Ala Lys
        275                 280                 285

Asp Asn Asp Asp Arg Gln Asp Ala Asn Gly Asn Leu Val Lys Gly Asp
    290                 295                 300

Ala Ala Asn Thr Gly Val His Ala Leu Leu Gly Leu His Asn Glu Ser
305                 310                 315                 320

Phe Tyr Gly Leu Arg Asp Gly Thr Ser Lys Thr Ala Leu Leu Tyr Gly
                325                 330                 335

His Gly Leu Gly Ala Glu Val Lys Gly Ile Gly Ser Asp Gly Ala Leu
            340                 345                 350

Arg Pro Gly Ala Asn Thr Trp Arg Phe Ala Ser Tyr Gly Thr Thr Pro
        355                 360                 365

Leu Ser Asp Arg Trp Phe Ile Ala Pro Ala Val Leu Ala Gln Ser Ser
    370                 375                 380

Lys Asp Arg Tyr Val Asp Gly Asp Ser Tyr Gln Trp Ala Thr Leu Asn
385                 390                 395                 400

Leu Arg Leu Ile Gln Glu Val Thr Gln Asn Phe Ala Leu Ala Trp Glu
                405                 410                 415

Gly Ser Tyr Gln Tyr Met Asp Leu Gln Pro Glu Gly Tyr Asn Asp Arg
            420                 425                 430

His Ala Val Asn Gly Ser Phe Tyr Lys Leu Thr Phe Ala Pro Thr Phe
        435                 440                 445

Lys Val Gly Ser Ile Gly Asp Phe Phe Ser Arg Pro Glu Ile Arg Phe
    450                 455                 460

Tyr Thr Ser Trp Met Asp Trp Ser Lys Lys Leu Asp Asn Tyr Ala Asn
465                 470                 475                 480

Asp Asp Ala Leu Gly Ser Asn Gly Phe Lys Ser Gly Gly Glu Trp Ser
                485                 490                 495

Phe Gly Met Gln Met Glu Thr Trp Phe
            500                 505


<210> SEQ ID NO 10
<211> LENGTH: 456
<212> TYPE: PRT
<213> ORGANISM: Klebsiella pneumoniae

<400> SEQUENCE: 10

Met Asp Phe Glu Gln Ile Ser Arg Ser Leu Leu Pro Leu Leu Gly Gly
1               5                   10                  15

Lys Glu Asn Ile Ala Ser Ala Ala His Cys Ala Thr Arg Leu Arg Leu
            20                  25                  30

Val Leu Val Asp Asp Ala Leu Ala Asp Gln Gln Ala Ile Gly Lys Ile
        35                  40                  45

Asp Gly Val Lys Gly Cys Phe Arg Asn Ala Gly Gln Met Gln Ile Ile
    50                  55                  60

Phe Gly Thr Gly Val Val Asn Lys Val Tyr Ala Ala Phe Ile Gln Ala
65                  70                  75                  80

Ala Gly Ile Ser Glu Ser Ser Lys Ser Glu Ala Ala Asp Leu Ala Ala
                85                  90                  95

Lys Lys Leu Asn Pro Phe Gln Arg Ile Ala Arg Leu Leu Ser Asn Ile
```

-continued

```
            100                 105                 110

Phe Val Pro Ile Ile Pro Ala Ile Val Ala Ser Gly Leu Leu Met Gly
        115                 120                 125

Leu Leu Gly Met Val Lys Thr Tyr Gly Trp Val Asp Pro Ser Asn Ala
    130                 135                 140

Leu Tyr Ile Met Leu Asp Met Cys Ser Ser Ala Ala Phe Ile Ile Leu
145                 150                 155                 160

Pro Ile Leu Ile Gly Phe Thr Ala Ala Arg Glu Phe Gly Gly Asn Pro
                165                 170                 175

Tyr Leu Gly Ala Thr Leu Gly Gly Ile Leu Thr His Pro Ala Leu Thr
            180                 185                 190

Asn Ala Trp Gly Val Ala Ala Gly Phe His Thr Met Asn Phe Phe Gly
        195                 200                 205

Ile Glu Val Ala Met Ile Gly Tyr Gln Gly Thr Val Phe Pro Val Leu
    210                 215                 220

Leu Ala Val Trp Phe Met Ser Met Val Glu Lys Arg Leu Arg Arg Val
225                 230                 235                 240

Ile Pro Asp Ala Leu Asp Leu Ile Leu Thr Pro Phe Leu Thr Val Ile
                245                 250                 255

Ile Ser Gly Phe Ile Ala Leu Leu Leu Ile Gly Pro Ala Gly Arg Ala
            260                 265                 270

Leu Gly Asp Gly Ile Ser Phe Ile Leu Ser Thr Leu Ile Ser His Ala
        275                 280                 285

Gly Trp Leu Ala Gly Leu Leu Phe Gly Gly Leu Tyr Ser Val Ile Val
    290                 295                 300

Ile Thr Gly Ile His His Ser Phe His Ala Ile Glu Ala Gly Leu Leu
305                 310                 315                 320

Gly Asn Pro Ser Ile Gly Val Asn Phe Leu Leu Pro Ile Trp Ala Met
                325                 330                 335

Ala Asn Val Ala Gln Gly Gly Ala Cys Phe Ala Val Trp Phe Lys Thr
            340                 345                 350

Lys Asp Ala Lys Ile Lys Ala Ile Thr Leu Pro Ser Ala Phe Ser Ala
        355                 360                 365

Met Leu Gly Ile Thr Glu Ala Ala Ile Phe Gly Ile Asn Leu Arg Phe
    370                 375                 380

Val Lys Pro Phe Ile Ala Ala Leu Val Gly Gly Ala Ala Gly Gly Ala
385                 390                 395                 400

Trp Val Val Ser Met His Val Tyr Met Thr Ala Val Gly Leu Thr Ala
                405                 410                 415

Ile Pro Gly Met Ala Ile Val Gln Ala Ser Ser Leu Leu Asn Tyr Ile
            420                 425                 430

Ile Gly Met Ala Ile Ala Phe Ala Val Ala Phe Ala Leu Ser Leu Thr
        435                 440                 445

Leu Lys Tyr Lys Thr Asp Ala Glu
    450                 455
```

<210> SEQ ID NO 11
<211> LENGTH: 466
<212> TYPE: PRT
<213> ORGANISM: Salmonella enterica subsp. enterica serovar Typhimurium

<400> SEQUENCE: 11

```
Met Ser Leu Pro Ser Arg Leu Pro Ala Ile Leu Gln Ala Val Met Gln
1               5                   10                  15
```

-continued

```
Gly Gln Pro Arg Ala Leu Ala Asp Ser His Tyr Pro Arg Trp His His
            20                  25                  30

Ala Pro Val Thr Gly Leu Met Asn Asp Pro Asn Gly Phe Ile Glu Phe
        35                  40                  45

Ala Gly Arg Tyr His Leu Phe Tyr Gln Trp Asn Pro Leu Ala Cys Asp
    50                  55                  60

His Thr Phe Lys Cys Trp Ala His Trp Ser Ser Ile Asp Leu Leu His
65                  70                  75                  80

Trp Gln His Glu Pro Ile Ala Leu Met Pro Asp Glu Glu Tyr Asp Arg
                85                  90                  95

Asn Gly Cys Tyr Ser Gly Ser Ala Val Asp Asn Asn Gly Thr Leu Thr
            100                 105                 110

Leu Cys Tyr Thr Gly Asn Val Lys Phe Ala Glu Gly Gly Arg Thr Ala
        115                 120                 125

Trp Gln Cys Leu Ala Thr Glu Asn Ala Asp Gly Thr Phe Arg Lys Ile
    130                 135                 140

Gly Pro Val Leu Pro Leu Pro Glu Gly Tyr Thr Gly His Val Arg Asp
145                 150                 155                 160

Pro Lys Val Trp Arg His Glu Asp Leu Trp Tyr Met Val Leu Gly Ala
                165                 170                 175

Gln Asp Arg Gln Lys Arg Gly Lys Val Leu Leu Phe Ser Ser Ala Asp
            180                 185                 190

Leu His Gln Trp Thr Ser Met Gly Glu Ile Ala Gly His Gly Ile Asn
        195                 200                 205

Gly Leu Asp Asp Val Gly Tyr Met Trp Glu Cys Pro Asp Leu Phe Pro
    210                 215                 220

Leu Gly Asp Gln His Ile Leu Ile Cys Cys Pro Gln Gly Ile Ala Arg
225                 230                 235                 240

Glu Glu Glu Cys Tyr Leu Asn Thr Tyr Pro Ala Val Trp Met Ala Gly
                245                 250                 255

Glu Phe Asp Tyr Ala Ala Gly Ala Phe Arg His Gly Glu Leu His Glu
            260                 265                 270

Leu Asp Ala Gly Phe Glu Phe Tyr Ala Pro Gln Thr Met Leu Thr Ser
        275                 280                 285

Asp Gly Arg Arg Leu Leu Val Gly Trp Met Gly Val Pro Glu Gly Glu
    290                 295                 300

Glu Met Leu Gln Pro Thr Leu Asn Asn Gly Trp Ile His Gln Met Thr
305                 310                 315                 320

Cys Leu Arg Glu Leu Glu Phe Ile Asn Gly Gln Leu Tyr Gln Arg Pro
                325                 330                 335

Leu Arg Glu Leu Ser Ala Leu Arg Gly Glu Ala Asn Gly Trp Ser Gly
            340                 345                 350

Asn Ala Leu Pro Leu Ala Pro Met Glu Ile Asp Leu Gln Thr Arg Gly
        355                 360                 365

Gly Asp Met Leu Ser Leu Asp Phe Gly Gly Val Leu Thr Leu Glu Cys
    370                 375                 380

Asp Ala Ser Gly Leu Arg Leu Ala Arg Arg Ser Leu Ala Ser Asp Glu
385                 390                 395                 400

Met His Tyr Arg Tyr Trp Arg Gly Asn Val Arg Ser Leu Arg Val Phe
                405                 410                 415

Ile Asp Gln Ser Ser Val Glu Ile Phe Ile Asn Gly Gly Glu Gly Val
            420                 425                 430

Met Ser Ser Arg Tyr Phe Pro Ala Cys Ser Gly Gln Leu Thr Phe Ser
```

-continued

```
        435                 440                 445

Gly Ile Thr Pro Asp Ala Phe Cys Tyr Trp Pro Leu Arg Thr Cys Met
    450                 455                 460

Val Glu
465


<210> SEQ ID NO 12
<211> LENGTH: 334
<212> TYPE: PRT
<213> ORGANISM: Salmonella enterica subsp. enterica serovar Typhimurium

<400> SEQUENCE: 12

Met Lys Thr Lys Arg Val Thr Ile Lys Asp Ile Ala Glu Gln Ala Gly
1               5                   10                  15

Val Ser Lys Ala Thr Ala Ser Leu Val Leu Asn Gly Arg Gly Lys Glu
            20                  25                  30

Leu Arg Val Ala Gln Glu Thr Arg Glu Arg Val Leu Ser Ile Ala Arg
        35                  40                  45

Lys His His Tyr Gln Pro Ser Ile His Ala Arg Ser Leu Arg Asn Asn
    50                  55                  60

Arg Ser His Thr Ile Gly Leu Val Val Pro Glu Ile Thr Asn His Gly
65                  70                  75                  80

Phe Ala Val Phe Ala His Glu Leu Glu Met Leu Cys Arg Glu Ala Gly
                85                  90                  95

Val Gln Leu Leu Ile Ser Cys Thr Asp Glu Asn Pro Gly Gln Glu Ser
            100                 105                 110

Val Val Val Asn Asn Met Ile Ala Arg Gln Val Asp Gly Met Ile Val
        115                 120                 125

Ala Ser Cys Met His Asn Asp Ala Asp Tyr Leu Lys Leu Ser Gln Gln
    130                 135                 140

Leu Pro Val Val Leu Phe Asp Arg Cys Pro Asn Glu Ser Ala Leu Pro
145                 150                 155                 160

Leu Val Met Thr Asp Ser Ile Thr Pro Thr Ala Glu Leu Ile Ser Arg
                165                 170                 175

Ile Ala Pro Gln His Ser Asp Glu Phe Trp Phe Leu Gly Gly Gln Ala
            180                 185                 190

Arg Leu Ser Pro Ser Arg Asp Arg Leu Thr Gly Phe Thr Gln Gly Leu
        195                 200                 205

Ala Gln Ala Gly Ile Ala Leu Arg Pro Glu Trp Val Ile Asn Gly Asn
    210                 215                 220

Tyr His Pro Ser Ser Gly Tyr Glu Met Phe Ala Ala Leu Cys Ala Arg
225                 230                 235                 240

Leu Gly Arg Pro Pro Lys Ala Leu Phe Thr Ala Ala Cys Gly Leu Leu
                245                 250                 255

Glu Gly Val Leu Arg Tyr Met Ser Gln His His Leu Leu Asp Ser Asp
            260                 265                 270

Ile His Leu Thr Ser Phe Asp Asp His Tyr Leu Tyr Asp Ser Leu Ser
        275                 280                 285

Leu Arg Ile Asp Thr Val Gln Gln Asp Asn Arg Gln Leu Ala Trp His
    290                 295                 300

Cys Tyr Asp Leu Ile Ser Gln Leu Ile Glu Gly Asp Thr Pro Glu Thr
305                 310                 315                 320

Leu Gln Arg Tyr Leu Pro Ala Thr Leu Gln Phe Arg His Gln
                325                 330
```

-continued

<210> SEQ ID NO 13
<211> LENGTH: 483
<212> TYPE: PRT
<213> ORGANISM: Avibacterium gallinarum

<400> SEQUENCE: 13

```
Met Ile Ile Phe Asn Glu Gly Lys Tyr Lys Ser Leu Tyr Ala Ala Glu
1               5                   10                  15

Gln Gly Glu Leu Glu Lys Ile Ala Gln Thr Val Ala Gln Asp Gln Asp
            20                  25                  30

Phe Arg Pro Val Tyr His Leu Ala Pro Pro Thr Gly Leu Leu Asn Asp
        35                  40                  45

Pro Asn Gly Leu Ile Phe Asp Gly Glu Lys Tyr His Leu Phe Tyr Gln
    50                  55                  60

Trp Tyr Pro Phe Asp Ala Leu His Gly Met Lys His Trp Gln His Phe
65                  70                  75                  80

Ile Thr Gln Asp Phe Lys Gln Phe Ser Gln Ala Asp Leu Leu Val Pro
                85                  90                  95

Cys Glu Leu Tyr Glu Ser His Gly Cys Tyr Ser Gly Gly Ala Val Lys
            100                 105                 110

Ile Gly Asp Gln Ile Ala Val Phe Tyr Thr Gly Asn Thr Arg Arg Pro
        115                 120                 125

Ser Asp Asn Gln Arg Val Pro Tyr Gln Asn Leu Ala Ile Phe Ser Lys
    130                 135                 140

Asp Gly Lys Leu Leu Ser Lys Arg Pro Leu Ile Glu Gln Ala Pro Gln
145                 150                 155                 160

Gly Tyr Thr Glu His Val Arg Asp Pro Lys Pro Phe Leu Thr Lys Asp
                165                 170                 175

Gly Lys Ile Arg Phe Ile Cys Gly Ala Gln Arg Glu Asn Leu Thr Gly
            180                 185                 190

Thr Ala Leu Val Phe Glu Met Asp Asn Leu Ala Asp Thr Pro Arg Leu
        195                 200                 205

Leu Gly Glu Leu Ala Leu Pro Ala Phe Asp Asn Gln Gly Val Phe Met
    210                 215                 220

Trp Glu Cys Pro Asp Leu Ser Gln Met Gly Asp Lys Ser Leu Phe Ile
225                 230                 235                 240

Trp Ser Pro Gln Gly Lys Ala Arg Glu Leu Glu Gln Tyr Gln Asn Asn
                245                 250                 255

Tyr His Ala Val Tyr Ala Leu Gly Glu Leu Ala Asp Arg Gln Phe His
            260                 265                 270

Ala Glu Gln Ile Ala Glu Leu Asp Gln Gly Phe Asp Phe Tyr Ala Pro
        275                 280                 285

Gln Thr Phe Ser Gly Thr Gln Thr Met Leu Leu Gly Trp Val Gly Leu
    290                 295                 300

Pro Asp Leu Ser Tyr Pro Thr Asp Leu Tyr Lys Trp His Ser Met Leu
305                 310                 315                 320

Ser Met Pro Arg Gln Leu Arg Leu Gln Asp Gly Lys Ile Tyr Gln Gln
                325                 330                 335

Pro Ile Glu Asn Ile Tyr Lys Asn Leu Thr Ala Leu Gln Ser Ile Thr
            340                 345                 350

Val Glu Lys Glu Ala Glu Ile Ala Asp Leu Asp Arg Ala Tyr Leu Lys
        355                 360                 365

Phe Asp Ala Asn Ala Gln Pro Phe Ser Leu Lys Phe Phe Asn Asn Ala
    370                 375                 380
```

Gln Asn Gln Arg Leu Ile Leu Ser Tyr Asp Gly Glu Met Leu Cys Leu
385 390 395 400

Asp Arg Ser Gln Thr Glu Gln Thr Asp Ser Met Lys Ser Phe Gly Asp
405 410 415

Lys Arg Tyr Cys Arg Ile Glu Asp Leu Arg Gln Val Glu Ile Phe Phe
420 425 430

Asp Arg Ser Val Ala Glu Ile Phe Leu Asn Gln Gly Glu Lys Ala Met
435 440 445

Thr Ser Arg Phe Phe Ile Cys Ala Arg Glu Asn Gln Leu Cys Thr Asp
450 455 460

Lys Pro Leu Thr Leu Gln Val Gly Tyr Pro Lys Lys Ile Glu Val Asp
465 470 475 480

Tyr Thr Lys

<210> SEQ ID NO 14
<211> LENGTH: 548
<212> TYPE: PRT
<213> ORGANISM: Arthrobacter globiformis

<400> SEQUENCE: 14

Met Glu Arg Thr Cys Ile Thr Val Arg Ala Ile Val Arg Phe His Ile
1 5 10 15

Glu Gln Arg Gln Thr Ile Val Asn Lys Gln Arg Thr Lys Arg Gly Ile
20 25 30

Leu Thr Ala Ala Leu Ser Ile Gly Ala Leu Gly Ala Thr Leu Ile Ser
35 40 45

Gly Pro Ala Val Ala Ala Thr Asp Ala Ala Pro Gly Phe Pro Gln Pro
50 55 60

Thr Glu His Thr Gln Lys Ala Tyr Ser Pro Thr Asp Asn Phe Thr Ser
65 70 75 80

Arg Trp Thr Arg Ala Asp Ala Lys Gln Leu Lys Ala Met Ser Asp Pro
85 90 95

Asp Ala Gly Ser Arg Glu Asn Ser Met Pro Thr Glu Tyr Thr Met Pro
100 105 110

Thr Val Ser Gln Asp Phe Pro Asp Met Ser Asn Glu Lys Val Trp Val
115 120 125

Trp Asp Thr Trp Pro Leu Ile Asp Glu Asn Ala Asn Gln Tyr Ser Val
130 135 140

Asn Gly Gln Glu Ile Ile Phe Ser Leu Val Ala Asp Arg Lys Leu Gly
145 150 155 160

Phe Asp Glu Arg His Gln Tyr Ala Arg Ile Gly Tyr Phe Tyr Arg Pro
165 170 175

Ala Gly Ile Pro Ala Asp Glu Arg Pro Glu Asp Gly Gly Trp Thr Tyr
180 185 190

Gly Gly Gln Val Phe Asp Glu Gly Val Thr Gly Lys Ile Phe Glu Asp
195 200 205

Gln Ser Phe Thr His Gln Thr Gln Trp Ser Gly Ser Ala Arg Val Ser
210 215 220

Lys Asn Gly Glu Ile Lys Leu Phe Phe Thr Asp Val Ala Phe Tyr Arg
225 230 235 240

Asp Lys Asp Gly Gln Asp Val Lys Pro Tyr Asp Ser Arg Ile Ala Leu
245 250 255

Ser Val Gly His Val His Ser Asn Lys Lys Gly Val Lys Leu Thr Gly
260 265 270

Phe Asn Lys Val Lys Glu Leu Leu Gln Ala Asp Gly Lys Asn Tyr Gln
        275                 280                 285

Asn Ala Ala Gln Asn Ser Tyr Tyr Asn Phe Arg Asp Pro Phe Thr Phe
    290                 295                 300

Val Asp Pro Ala His Pro Gly Glu Thr Tyr Met Val Phe Glu Gly Asn
305                 310                 315                 320

Ser Ala Met Asp Arg Asp Glu Ala Lys Cys Thr Ala Glu Asp Leu Gly
                325                 330                 335

Tyr Arg Glu Gly Glu Thr Asn Gly Glu Thr Val Glu Gln Val Asn Asn
            340                 345                 350

Ser Gly Ala Thr Tyr Gln Ile Gly Asn Val Gly Leu Ala Arg Ala Lys
        355                 360                 365

Asn Lys Ala Leu Thr Glu Trp Glu Phe Leu Pro Pro Ile Leu Ser Ala
    370                 375                 380

Asn Cys Val Thr Asp Gln Thr Glu Arg Pro Gln Ile Tyr Met Gln Asp
385                 390                 395                 400

Gly Lys Tyr Tyr Leu Phe Thr Ile Ser His Arg Ser Thr Phe Ala Thr
                405                 410                 415

Gly Ile Asp Gly Pro Glu Gly Val Tyr Gly Phe Val Gly Asn Gly Ile
            420                 425                 430

Arg Ser Asp Tyr Gln Pro Leu Asn Arg Gly Ser Gly Leu Ala Leu Gly
        435                 440                 445

Ser Pro Thr Asn Leu Asn Phe Ala Ala Gly Thr Pro Phe Ala Pro Asp
    450                 455                 460

Tyr Asn Gln His Pro Gly Gln Phe Gln Ala Tyr Ser His Tyr Val Met
465                 470                 475                 480

Pro Gly Gly Leu Val Gln Ser Phe Ile Asp Thr Ile Gly Thr Lys Asp
                485                 490                 495

Asn Phe Val Arg Gly Gly Thr Leu Gly Pro Thr Val Lys Leu Asn Ile
            500                 505                 510

Lys Gly Asp Ser Ala Thr Val Asp Tyr Asn Tyr Gly Asp Asn Gly Leu
        515                 520                 525

Gly Gly Trp Ala Asp Ile Pro Ala Asn Arg Glu Leu Lys Asn Ser Lys
    530                 535                 540

Ala Val Ala Lys
545

<210> SEQ ID NO 15
<211> LENGTH: 203
<212> TYPE: DNA
<213> ORGANISM: Artificial
<220> FEATURE:
<223> OTHER INFORMATION: Promoter sequence

<400> SEQUENCE: 15
tgcgtcgcca ttctgtcgca acacgccaga atgcggcggc gatcactaac tcaacaaatc 60
aggcgatgta accgctttca atctgtgagt gatttcacag tatcttaaca atgtgatagc 120
tatgattgca ccgtgcctac aagcatcgtg gaggtccgtg actttcacgc atacaacaaa 180
cattaaccaa gagaaaaaca gct 203

<210> SEQ ID NO 16
<211> LENGTH: 203
<212> TYPE: DNA
<213> ORGANISM: Artificial
<220> FEATURE:

<223> OTHER INFORMATION: Promoter sequence

<400> SEQUENCE: 16
tgcgtcgcca ttctgtcgca acacgccaga atgcggcggc gatcactaac tcaacaaatc 60
aggcgatgta accgctttca atctgtgagt gatttcacag tatcttaaca atgtgatagc 120
tatgattgca ccgtgcctac aagcatcgtg gaggtccgtg actttcacgc atacaacaaa 180
cattaaccaa ctgagaaaca gct 203

<210> SEQ ID NO 17
<211> LENGTH: 203
<212> TYPE: DNA
<213> ORGANISM: Artificial
<220> FEATURE:
<223> OTHER INFORMATION: Promoter sequence

<400> SEQUENCE: 17
tgcgtcgcca ttctgtcgca acacgccaga atgcggcggc gatcactaac tcaacaaatc 60
aggcgatgta accgctttca atctgtgagt gatttcacag tatcttaaca atgtgatagc 120
tatgattgca ccgtgcctac aagcatcgtg gaggtccgtg actttcacgc atacaacaaa 180
cattaacaaa aaccggagat acc 203

<210> SEQ ID NO 18
<211> LENGTH: 141
<212> TYPE: DNA
<213> ORGANISM: Artificial
<220> FEATURE:
<223> OTHER INFORMATION: Promoter sequence

<400> SEQUENCE: 18
tgtgagttag ctcactcatt aggcacccca ggctttacac tttatgcttc cggctcgtat 60
gttgtgtgga atgcctacaa gcatcgtgga ggtccgtgac tttcacgcat acaacaaaca 120
ttaaccaagg aggaaacagc t 141

<210> SEQ ID NO 19
<211> LENGTH: 203
<212> TYPE: DNA
<213> ORGANISM: Artificial
<220> FEATURE:
<223> OTHER INFORMATION: Promoter sequence

<400> SEQUENCE: 19
tgcgtcgcca ttctgtcgca acacgccaga atgcggcggc gatcactaac tcaacaaatc 60
aggcgatgta accgctttca atctgtgagt gatttcacag tatcttaaca atgtgatagc 120
tatgattgca ccgtgcctac aagcatcgtg gaggtccgtg actttcacgc atacaacaaa 180
cattaaccaa aggaaaaaca gct 203

<210> SEQ ID NO 20
<211> LENGTH: 203
<212> TYPE: DNA
<213> ORGANISM: Artificial
<220> FEATURE:
<223> OTHER INFORMATION: Promoter sequence

<400> SEQUENCE: 20
tgcgtcgcca ttctgtcgca acacgccaga atgcggcggc gatcactaac tcaacaaatc 60
aggcgatgta accgctttca atctgtgagt gatttcacag tatcttaaca atgtgatagc 120
tatgattgca ccgtgcctac aagcatcgtg gaggtccgtg actttcacgc atacaacaaa 180
cattaaccaa ctaggaaaca gct 203

<210> SEQ ID NO 21
<211> LENGTH: 203
<212> TYPE: DNA
<213> ORGANISM: Artificial
<220> FEATURE:
<223> OTHER INFORMATION: Promoter sequence

<400> SEQUENCE: 21
tgcgtcgcca ttctgtcgca acacgccaga atgcggcggc gatcactaac tcaacaaatc 60
aggcgatgta accgctttca atctgtgagt gatttcacag tatcttaaca atgtgatagc 120
tatgattgca ccgtgcctac aagcatcgtg gaggtccgtg actttcacgc atacaacaaa 180
cattaaccaa ccgagaaaca gct 203

<210> SEQ ID NO 22
<211> LENGTH: 310
<212> TYPE: DNA
<213> ORGANISM: Artificial
<220> FEATURE:
<223> OTHER INFORMATION: Promoter sequence

<400> SEQUENCE: 22
atgcgcaaat gcggcacgcc ttgcagatta cggtttgcca cacttttcat ccttctcctg 60
gtgacataat ccacatcaat cgaaaatgtt aataaatttg ttgcgcgaat gatctaacaa 120
acatgcatca tgtacaatca gatggaataa atggcgcgat aacgctcatt ttatgacgag 180
gcacacacat tttaagttcg atatttctcg tttttgctcg ttaacgataa gtttacagca 240
tgcctacaag catcgtggag gtccgtgact ttcacgcata caacaaacat taaccaacta 300
ggaaacagct 310

<210> SEQ ID NO 23
<211> LENGTH: 203
<212> TYPE: DNA
<213> ORGANISM: Artificial
<220> FEATURE:
<223> OTHER INFORMATION: Promoter sequence

<400> SEQUENCE: 23
tgcgtcgcca ttctgtcgca acacgccaga atgcggcggc gatcactaac tcaacaaatc 60
aggcgatgta accgctttca atctgtgagt gatttcacag tatcttaaca atgtgatagc 120
tatgattgca ccgtgcctac aagcatcgtg gaggtccgtg actttcacgc atacaacaaa 180
cattaaccaa gagcaaaaca gct 203

<210> SEQ ID NO 24
<211> LENGTH: 203
<212> TYPE: DNA
<213> ORGANISM: Artificial
<220> FEATURE:
<223> OTHER INFORMATION: Promoter sequence

<400> SEQUENCE: 24
tgcgtcgcca ttctgtcgca acacgccaga atgcggcggc gatcactaac tcaacaaatc 60
aggcgatgta accgctttca atctgtgagt gatttcacag tatcttaaca atgtgatagc 120
tatgattgca ccgtgcctac aagcatcgtg gaggtccgtg actttcacgc atacaacaaa 180
cattaaccaa ggaggaaaca gct 203

<210> SEQ ID NO 25
<211> LENGTH: 189
<212> TYPE: DNA
<213> ORGANISM: Artificial
<220> FEATURE:
<223> OTHER INFORMATION: Promoter sequence

<400> SEQUENCE: 25
gaaaacattc ataaattaaa tgtgaattgc cgcacacatt attaaataag atttacaaaa 60
tgttcaaaat gacgcatgaa atcacgtttc actttcgaat tatgagcgaa tatgcgcgat 120
gcctacaagc atcgtggagg tccgtgactt tcacgcatac aacaaacatt aaccaaggag 180
gaaacagct 189

<210> SEQ ID NO 26
<211> LENGTH: 239
<212> TYPE: DNA
<213> ORGANISM: Artificial
<220> FEATURE:
<223> OTHER INFORMATION: Promoter sequence

<400> SEQUENCE: 26
ccatttagcc atagtaaaaa catgaattgt ttgatttcgc gcatattcgc tcataattcg 60
aaagtgaaac gtgatttcat gcgtcatttt gaacattttg taaatcttat ttaataatgt 120
gtgcggcaat tcacatttaa tttatgaatg ttttcttaac atcgcggcat gcctacaagc 180
atcgtggagg tccgtgactt tcacgcatac aacaaacatt aaccaaggag gaaacagct 239

<210> SEQ ID NO 27
<211> LENGTH: 300
<212> TYPE: DNA
<213> ORGANISM: artificial
<220> FEATURE:
<223> OTHER INFORMATION: Promoter sequence

<400> SEQUENCE: 27
gcggcacgcc ttgcagatta cggtttgcca cacttttcat ccttctcctg gtgacataat 60
ccacatcaat cgaaaatgtt aataaatttg ttgcgcgaat gatctaacaa acatgcatca 120
tgtacaatca gatggaataa atggcgcgat aacgctcatt ttatgacgag gcacacacat 180
tttaagttcg atatttctcg tttttgctcg ttaacgataa gtttacagca tgcctacaag 240
catcgtggag gtccgtgact ttcacgcata caacaaacat taaccaagga ggaaacagct 300

<210> SEQ ID NO 28
<211> LENGTH: 310
<212> TYPE: DNA
<213> ORGANISM: Artificial
<220> FEATURE:
<223> OTHER INFORMATION: Promoter sequence

<400> SEQUENCE: 28
atgcgcaaat gcggcacgcc ttgcagatta cggtttgcca cacttttcat ccttctcctg 60
gtgacataat ccacatcaat cgaaaatgtt aataaatttg ttgcgcgaat gatctaacaa 120
acatgcatca tgtacaatca gatggaataa atggcgcgat aacgctcatt ttatgacgag 180
gcacacacat tttaagttcg atatttctcg tttttgctcg ttaacgataa gtttacagca 240
tgcctacaag catcgtggag gtccgtgact ttcacgcata caacaaacat taaccaactg 300
agaaacagct 310

<210> SEQ ID NO 29
<211> LENGTH: 310
<212> TYPE: DNA
<213> ORGANISM: Artificial
<220> FEATURE:
<223> OTHER INFORMATION: Promoter sequence

<400> SEQUENCE: 29
atgcgcaaat gcggcacgcc ttgcagatta cggtttgcca cacttttcat ccttctcctg 60
gtgacataat ccacatcaat cgaaaatgtt aataaatttg ttgcgcgaat gatctaacaa 120
acatgcatca tgtacaatca gatggaataa atggcgcgat aacgctcatt ttatgacgag 180
gcacacacat tttaagttcg atatttctcg tttttgctcg ttaacgataa gtttacagca 240
tgcctacaag catcgtggag gtccgtgact ttcacgcata caacaaacat taaccaaccg 300
agaaacagct 310

<210> SEQ ID NO 30
<211> LENGTH: 310
<212> TYPE: DNA
<213> ORGANISM: Artificial
<220> FEATURE:
<223> OTHER INFORMATION: Promoter sequence

<400> SEQUENCE: 30
atgcgcaaat gcggcacgcc ttgcagatta cggtttgcca cacttttcat ccttctcctg 60
gtgacataat ccacatcaat cgaaaatgtt aataaatttg ttgcgcgaat gatctaacaa 120
acatgcatca tgtacaatca gatggaataa atggcgcgat aacgctcatt ttatgacgag 180
gcacacacat tttaagttcg atatttctcg tttttgctcg ttaacgataa gtttacagca 240
tgcctacaag catcgtggag gtccgtgact ttcacgcata caacaaacat taaccaagag 300
aaaaacagct 310

<210> SEQ ID NO 31
<211> LENGTH: 350
<212> TYPE: DNA
<213> ORGANISM: Artificial
<220> FEATURE:
<223> OTHER INFORMATION: Promoter sequence

<400> SEQUENCE: 31
tgcgtcgcca ttctgtcgca acacgccaga atgcggcggc gatcactaac tcaacaaatc 60
aggcgatgta accgctttca atctgtgagt gatttcacag tatcttaaca atgtgatagc 120
tatgattgca ccgttttaac gttgtaaccc gtatgtaaca gtgaataatc acttttgccg 180
aggtaacagc gtcataacaa caattaaagc cgttttctgg agcgttaccg ggcatggaag 240
aacgaatttt aaaaagtgag cttcggcgtt cagtaacact tcattaactc tactgccccg 300
ccgagcattt atctcaagca ctaccctgca taagcaagga ggaaacagct 350

<210> SEQ ID NO 32
<211> LENGTH: 310
<212> TYPE: DNA
<213> ORGANISM: Artificial
<220> FEATURE:
<223> OTHER INFORMATION: Promoter sequence

<400> SEQUENCE: 32
atgcgcaaat gcggcacgcc ttgcagatta cggtttgcca cacttttcat ccttctcctg 60
gtgacataat ccacatcaat cgaaaatgtt aataaatttg ttgcgcgaat gatctaacaa 120
acatgcatca tgtacaatca gatggaataa atggcgcgat aacgctcatt ttatgacgag 180
gcacacacat tttaagttcg atatttctcg tttttgctcg ttaacgataa gtttacagca 240
tgcctacaag catcgtggag gtccgtgact ttcacgcata caacaaacat taaccaaagg 300
aaaaacagct 310

<210> SEQ ID NO 33
<211> LENGTH: 300
<212> TYPE: DNA
<213> ORGANISM: Artificial
<220> FEATURE:
<223> OTHER INFORMATION: Promoter sequence

<400> SEQUENCE: 33
gcggcacgcc ttgcagatta cggtttgcca cacttttcat ccttctcctg gtgacataat 60
ccacatcaat cgaaaatgtt aataaatttg ttgcgcgaat gatctaacaa acatgcatca 120
tgtacaatca gatggaataa atggcgcgat aacgctcatt ttatgacgag gcacacacat 180
tttaagttcg atatttctcg tttttgctcg ttaacgataa gtttacagca tgcctacaag 240
catcgtggag gtccgtgact ttcacgcata caacaaacat taaccaagag caaaacagct 300

<210> SEQ ID NO 34
<211> LENGTH: 310
<212> TYPE: DNA
<213> ORGANISM: Artificial
<220> FEATURE:
<223> OTHER INFORMATION: Promoter sequence

<400> SEQUENCE: 34
atgcgcaaat gcggcacgcc ttgcagatta cggtttgcca cacttttcat ccttctcctg 60
gtgacataat ccacatcaat cgaaaatgtt aataaatttg ttgcgcgaat gatctaacaa 120
acatgcatca tgtacaatca gatggaataa atggcgcgat aacgctcatt ttatgacgag 180
gcacacacat tttaagttcg atatttctcg tttttgctcg ttaacgataa gtttacagca 240
tgcctacaag catcgtggag gtccgtgact ttcacgcata caacaaacat taaccaagag 300
ctaaacagct 310

<210> SEQ ID NO 35
<211> LENGTH: 189
<212> TYPE: DNA
<213> ORGANISM: Artificial
<220> FEATURE:
<223> OTHER INFORMATION: Promoter sequence

<400> SEQUENCE: 35
gaaaacattc ataaattaaa tgtgaattgc cgcacacatt attaaataag atttacaaaa 60
tgttcaaaat gacgcatgaa atcacgtttc actttcgaat tatgagcgaa tatgcgcgat 120
gcctacaagc atcgtggagg tccgtgactt tcacgcatac aacaaacatt aaccaaggag 180
gaaacagct 189

<210> SEQ ID NO 36
<211> LENGTH: 107
<212> TYPE: DNA
<213> ORGANISM: Escherichia coli

<400> SEQUENCE: 36
tgtgagttag ctcactcatt aggcacccca ggctttacac tttatgcttc cggctcgtat 60
gttgtgtgga attgtgagcg gataacaatt tcacacagga aacagct 107

<210> SEQ ID NO 37
<211> LENGTH: 300
<212> TYPE: DNA
<213> ORGANISM: Artificial
<220> FEATURE:
<223> OTHER INFORMATION: Promoter sequence

<400> SEQUENCE: 37
gcggcacgcc ttgcagatta cggtttgcca cacttttcat ccttctcctg gtgacataat 60
ccacatcaat cgaaaatgtt aataaatttg ttgcgcgaat gatctaacaa acatgcatca 120
tgtacaatca gatggaataa atggcgcgat aacgctcatt ttatgacgag gcacacacat 180
tttaagttcg atatttctcg tttttgctcg ttaacgataa gtttacagca tgcctacaag 240
catcgtggag gtccgtgact ttcacgcata caacaaacat taaccaagaa caaaacagct 300

<210> SEQ ID NO 38
<211> LENGTH: 300
<212> TYPE: DNA
<213> ORGANISM: Artificial
<220> FEATURE:
<223> OTHER INFORMATION: Promoter sequence

<400> SEQUENCE: 38
gcggcacgcc ttgcagatta cggtttgcca cacttttcat ccttctcctg gtgacataat 60
ccacatcaat cgaaaatgtt aataaatttg ttgcgcgaat gatctaacaa acatgcatca 120
tgtacaatca gatggaataa atggcgcgat aacgctcatt ttatgacgag gcacacacat 180
tttaagttcg atatttctcg tttttgctcg ttaacgataa gtttacagca tgcctacaag 240
catcgtggag gtccgtgact ttcacgcata caacaaacat taaccaaatt cgaaacagct 300

<210> SEQ ID NO 39
<211> LENGTH: 300
<212> TYPE: DNA
<213> ORGANISM: artificial
<220> FEATURE:
<223> OTHER INFORMATION: promoter sequence

<400> SEQUENCE: 39
gcggcacgcc ttgcagatta cggtttgcca cacttttcat ccttctcctg gtgacataat 60
ccacatcaat cgaaaatgtt aataaatttg ttgcgcgaat gatctaacaa acatgcatca 120
tgtacaatca gatggaataa atggcgcgat aacgctcatt ttatgacgag gcacacacat 180
tttaagttcg atatttctcg tttttgctcg ttaacgattt aattacagca tgcctacaag 240
catcgtggag gtccgtgact ttcacgcata caacaaacat taaccaagga ggaaacagct 300

<210> SEQ ID NO 40
<211> LENGTH: 332
<212> TYPE: PRT
<213> ORGANISM: Neisseria meningitidis

<400> SEQUENCE: 40

Met Gln Pro Leu Val Ser Val Leu Ile Cys Ala Tyr Asn Val Glu Lys
1 5 10 15

Tyr Phe Ala Gln Ser Leu Ala Ala Val Val Asn Gln Thr Trp Arg Asn
20 25 30

Leu Glu Ile Leu Ile Val Asp Asp Gly Ser Thr Asp Gly Thr Leu Ala
35 40 45

Ile Ala Lys Asp Phe Gln Lys Arg Asp Ser Arg Ile Lys Ile Leu Ala 50 55 60

Gln Ala Gln Asn Ser Gly Leu Ile Pro Ser Leu Asn Ile Gly Leu Asp
65 70 75 80

Glu Leu Ala Lys Ser Gly Met Gly Glu Tyr Ile Ala Arg Thr Asp Ala
85 90 95

Asp Asp Ile Ala Ala Pro Asp Trp Ile Glu Lys Ile Val Gly Glu Met
100 105 110

Glu Lys Asp Arg Ser Ile Ile Ala Met Gly Ala Trp Leu Glu Val Leu
115 120 125

Ser Glu Glu Lys Asp Gly Asn Arg Leu Ala Arg His His Arg His Gly
130 135 140

Lys Ile Trp Lys Lys Pro Thr Arg Pro Glu Asp Ile Ala Asp Phe Phe
145 150 155 160

Pro Phe Gly Asn Pro Ile His Asn Asn Thr Met Ile Met Arg Arg Ser
165 170 175

Val Ile Asp Gly Gly Leu Arg Tyr Asn Thr Glu Arg Asp Trp Ala Glu
180 185 190

Asp Tyr Gln Phe Trp Tyr Asp Val Ser Lys Leu Gly Arg Leu Ala Tyr
195 200 205

Tyr Pro Glu Ala Leu Val Lys Tyr Arg Leu His Ala Asn Gln Val Ser
210 215 220

Ser Lys Tyr Ser Ile Arg Gln His Glu Ile Ala Gln Gly Ile Gln Lys
225 230 235 240

Thr Ala Arg Asn Asp Phe Leu Gln Ser Met Gly Phe Lys Thr Arg Phe
245 250 255

Asp Ser Leu Glu Tyr Arg Gln Ile Lys Ala Val Ala Tyr Glu Leu Leu
260 265 270

Glu Lys His Leu Pro Glu Glu Asp Phe Glu Arg Ala Arg Arg Phe Leu
275 280 285

Tyr Gln Cys Phe Lys Arg Thr Asp Thr Leu Pro Ala Gly Ala Trp Leu
290 295 300

Asp Phe Ala Ala Asp Gly Arg Met Arg Arg Leu Phe Thr Leu Arg Gln
305 310 315 320

Tyr Phe Gly Ile Leu His Arg Leu Leu Lys Asn Arg
325 330

<210> SEQ ID NO 41
<211> LENGTH: 439
<212> TYPE: PRT
<213> ORGANISM: Helicobacter pylori

<400> SEQUENCE: 41

Met Ile Ser Val Tyr Ile Ile Ser Leu Lys Glu Ser Gln Arg Arg Leu
1 5 10 15

Asp Thr Glu Lys Leu Val Leu Glu Ser Asn Glu Lys Phe Lys Gly Arg
20 25 30

Cys Val Phe Gln Ile Phe Asp Ala Ile Ser Pro Lys His Glu Asp Phe
35 40 45

Glu Lys Phe Val Gln Glu Leu Tyr Asp Ser Ser Ser Leu Leu Lys Ser
50 55 60

Asp Trp Phe His Ser Asp Tyr Cys Tyr Gln Glu Leu Leu Pro Gln Glu
65 70 75 80

Phe Gly Cys Tyr Leu Ser His Tyr Leu Leu Trp Lys Glu Cys Val Lys
85 90 95

-continued

```
Leu Asn Gln Pro Val Val Ile Leu Glu Asp Asp Val Ala Leu Glu Ser
            100                 105                 110

Asn Phe Met Gln Ala Leu Glu Asp Cys Leu Lys Ser Pro Phe Asp Phe
        115                 120                 125

Val Arg Leu Tyr Gly His Tyr Trp Gly Gly His Lys Thr Asn Leu Cys
    130                 135                 140

Ala Leu Pro Val Tyr Thr Glu Thr Glu Glu Ala Glu Ala Ser Ile Glu
145                 150                 155                 160

Lys Thr Pro Ile Glu Asn Tyr Glu Val Thr Ser Pro Pro Pro Pro Asn
                165                 170                 175

Pro Thr Arg Asp Thr Gln Gln Asp Phe Ile Thr Glu Thr Gln Gln Asp
            180                 185                 190

Pro Lys Glu Leu Ser Glu Pro Cys Lys Ile Ala Pro Gln Lys Ile Ser
        195                 200                 205

Phe Asn Gln Val Val Phe Lys Lys Ile Lys Arg Lys Leu Asn Arg Phe
    210                 215                 220

Ile Gly Ser Ile Leu Ala Arg Thr Glu Val Tyr Lys Asn Ile Val Ala
225                 230                 235                 240

Lys Tyr Asp Asp Leu Thr Thr Lys Tyr Asp Asp Leu Thr Thr Lys Tyr
                245                 250                 255

Asp Asp Leu Thr Thr Lys Tyr Asp Asp Leu Thr Thr Lys Tyr Asp Asp
            260                 265                 270

Leu Asn Lys Asn Ile Ala Glu Lys Tyr Asp Glu Leu Met Gly Lys Tyr
        275                 280                 285

Glu Ser Leu Leu Ala Lys Glu Val Asn Ile Lys Glu Thr Phe Trp Glu
    290                 295                 300

Ser Arg Ala Asp Ser Glu Lys Glu Ala Leu Phe Leu Asp His Phe Tyr
305                 310                 315                 320

Leu Thr Ser Val Tyr Val Ala Thr Thr Ala Gly Tyr Tyr Leu Thr Pro
                325                 330                 335

Lys Gly Ala Lys Thr Phe Ile Glu Ala Thr Glu Arg Phe Lys Ile Ile
            340                 345                 350

Glu Pro Val Asp Met Phe Ile Asn Asn Pro Thr Tyr His Asp Ile Ala
        355                 360                 365

Asn Phe Thr Tyr Val Pro Cys Pro Val Ser Leu Asn Lys His Ala Phe
    370                 375                 380

Asn Ser Thr Ile Gln Asn Ala Lys Lys Pro Asp Ile Ser Leu Lys Pro
385                 390                 395                 400

Pro Lys Lys Ser Tyr Phe Asp Asn Leu Phe Tyr His Lys Phe Asn Ala
                405                 410                 415

Arg Lys Cys Leu Lys Ala Phe Asn Lys Tyr Ser Lys Gln Tyr Ala Pro
            420                 425                 430

Leu Lys Thr Pro Lys Glu Val
        435
```

<210> SEQ ID NO 42
<211> LENGTH: 730
<212> TYPE: DNA
<213> ORGANISM: Escherichia coli

<400> SEQUENCE: 42

```
atgaaacaaa cacaacgtca caacggtatt atcgaactgg ttaaacagca gggttatgtc      60

agtaccgaag agctggtaga gcatttctcc gtcagcccgc agactattcg ccgcgacctc     120

aatgagctgg cggagcaaaa cctgatcctg gccatcatgg cggtgcggcg ctgccttcca     180
```

-continued

```
gttcggttaa cacgccgtgg cacgatcgca aggccaccca gaccgaagaa aaagagcgca    240

tcgcccgcaa agtggcggag caaatcccca atggctcgac gctgtttatc gatatcggca    300

ccacgccgga agcggtagcg cacgcactgc tcaatcacag caatttgcgc attgtcacca    360

acaatctcaa cgttgctaac acgttgatgg taaaagaaga ttttcgcatc attctcgccg    420

gtggcgaatt acgcagccgc gatggcggga tcattggcga agcgacgctc gattttatct    480

cccagttccg ccttgatttc ggcattctgg ggataagcgg catcgatagc gacggctcgc    540

tgctggagtt cgattaccac gaagttcgca ccaaacgcgc cattattgag aactcgcgcc    600

acgttatgct ggttgtcgat cactcgaaat ttggccgtaa cgcgatggtc aatatgggca    660

gcatcagcat ggtagatgcc gtctacaccg acgccccgcc gccagtaagc gtgatgcagg    720

tgctgacgga                                                           730
```

IDENTIFICATION OF AN α-1,2-FUCOSYLTRANSFERASE FOR THE IN VIVO PRODUCTION OF PURE LNFP-I

CROSS-REFERENCE TO RELATED APPLICATIONS

This application is a National Stage entry pursuant to 35 U.S.C. § 371 of International Application No. PCT/EP2022/063315, filed on May 17, 2022, which claims priority to Denmark Application No. PA202170250, filed on May 17, 2021, the entire contents of all of which are hereby incorporated by reference in their entirety.

SEQUENCE LISTING

This instant application contains a sequence listing which has been submitted in a ascii text file via Patent Center and is hereby incorporated by reference in its entirety. Said text file, created on Nov. 14, 2023, is named 032991-8008 sequence listing.txt, and is 68,453 bytes in size.

FIELD

The present disclosure discloses the identification and introduction of a specific heterologous gene, which encodes an α-1,2-fucosyltransferase, into an LNT production strain to produce LNFP-I as the major HMO compound.

BACKGROUND

To bypass the drawbacks associated with the chemical synthesis of HMOs, several enzymatic methods and fermentative approaches have been developed. Fermentation based processes have been developed for several HMOs such as 2'-fucosyllactose, 3-fucosyllactose, lacto-N-tetraose, lacto-N-neotetraose, Lacto-N-fucopentaose I, 3'-sialyllactose and 6'-sialyllactose. Fermentation based processes typically utilize genetically engineered bacterial strains, such as recombinant *Escherichia coli* (*E. coli*).

Biosynthetic production, such as a fermentation process, of HMOs is a valuable, cost-effective and large-scale applicable solution for HMO manufacturing. It relies on genetically engineered bacteria constructed so as to express the glycosyltransferases needed for synthesis of the desired oligosaccharides and takes advantage of the bacteria's innate pool of nucleotide sugars as HMO precursors.

Recent developments in biotechnological production of HMOs have made it possible to overcome certain inherent limitations of bacterial expression systems. For example, HMO-producing bacterial cells may be genetically engineered to increase the limited intracellular pool of nucleotide sugars in the bacteria (WO2012112777), to improve activity of enzymes involved in the HMO production (WO2016040531), or to facilitate the secretion of synthesized HMOs into the extracellular media (WO2010142305, WO2017042382).

Further, expression of genes of interest in recombinant cells may be regulated by using particular promoter sequences or other gene expression regulators, like e.g. what has recently been described in WO2019123324.

Recently, improvements were made in the production of fucosylated HMOs, where a number of fucosyltransferases were identified, which showed enhanced functionality, thus enhancing the amount of produced product, as described in WO2019008133. In example, *E. coli* expressing a selection of α-1,2-fucosyltransferases, was shown in WO2019008133 to be capable of producing LNFP-I, however with considerable side product HMOs.

Thus, there is still an unmet need for alternative genetic engineering to produce HMOs.

SUMMARY

Herein we disclose an α-1,2-fucosyltransferase, Smob, which is superior to the previously disclosed α-1,2-fucosyltarsnferases for the biosynthetic production of LNFP-I, which overcomes the technical issue of side product formation and increases the LNFP-I titer and yield.

The expression of Smob, may in turn be combined with further genetic modifications, such as a sucrose utilization system or one or more metabolic pathway modifications that facilitate product formation and increase the titer of LNFP-I, while maintaining a low level of byproducts.

The present disclosure firstly relates to a method for producing one or more fucosylated human milk oligosaccharide (HMO), the method comprising the steps of, a) providing a genetically engineered cell capable of producing an HMO, wherein said cell comprises a recombinant nucleic acid encoding an α-1,2-fucosyltransferase protein as shown in SEQ ID NO: 1, or a functional homologue thereof having an amino acid sequence which is at least 70% identical to SEQ ID NO: 1,
b) culturing the cell according to (a) in a suitable cell culture medium to express said nucleic acid; and
c) harvesting the HMO(s) produced in step (b).

The disclosure further relates to a genetically engineered cell comprising a recombinant nucleic acid sequence encoding an α-1,2-fucosyltransferase protein as shown in SEQ ID NO: 1, or a functional homologue thereof having an amino acid sequence which is at least 70% identical, such as at least 75% identical, or such as at least 80% identical to SEQ ID NO: 1.

The disclosure also relates to a nucleic acid construct comprising a recombinant nucleic acid sequence which is at least 70% identical to SEQ ID NO: 2.

The disclosure further relates to the use of a genetically engineered cell, or the nucleic acid construct as described herein, in the manufacturing of one or more HMOs.

DETAILED DESCRIPTION

The steps of any method disclosed herein do not have to be performed in the exact order disclosed, unless explicitly stated.

The present disclosure relates to method for producing fucosylated oligosaccharides, wherein a genetically engineered cell is used for producing said fucosylated oligosaccharide. Said genetically engineered cell has been genetically engineered to express a heterologous α-1,2-fucosyltransferase which is capable of transferring a fucose residue from a donor substrate to an acceptor molecule, wherein said α-1,2-fucosyltransferase has higher specificity for lacto-N-tetraose (LNT) as acceptor molecule than towards lactose as acceptor molecule.

The α-1,2-Fucosyltransferase—Smob

The present disclosure refers to the identification of a specific heterologous gene (denoted as smob), which codes for an α-1,2-fucosyl-transferase, and its introduction into an LNT production strain in order to produce LNFP-I. The smob gene originates from the organism *Sulfuriflexus mobilis* (https://www.dsmz.de/collection/catalogue/details/culture/DSM-102939), which is a sulfur-oxidizing bacterium isolated from a brackish lake sediment.

In a preferred exemplary embodiment, the amino acid sequence encoding the α-1,2-fucosyltransferase Smob is 100% identical to SEQ ID NO: 1, which is the GenBank ID WP_126455392.1 originating from *Sulfuriflexus mobilis.*

Contrary to other α-1,2-fucosyltransferases, such as FutC (Genbank ref. no: WP_080473865.1), the Smob α-1,2-fucosyltransferase is able to selectively fucosylate LNT, while it has a very low activity on lactose. These beneficial effects have been confirmed in deep-well assays, see FIG. 1-5, as well as in fermentation data in the Examples below. Provided herein are α-1,2-fucosyltransferases originating from bacterial cells. Said fucosyltransferases utilizes lacto-N-tetraose as the acceptor molecule for their fucosyltransferase activity. Said fucosyltransferases can be used to synthesize fucosylated oligosaccharides based on LNT as acceptor molecule.

In this manner, not only higher LNFP-I titers can be achieved with Smob compared to FutC or FucT54 (FIG. 1A), but the pronounced formation of 2'-FL, which is a result of low specificity of the FutC enzyme, can be avoided (FIG. 2).

As shown in FIG. 3-5, the obtained final HMO profile differs significantly when the FutC, FucT54 or Smob enzymes are introduced in an LNT-producing strain. Notably, the HMO profile obtained from smob-expressing cells consists almost exclusively of LNFP-I (91%) (FIG. 5).

The features described here for the Smob enzyme are very interesting in the sense that a microorganism such as *Sulfuriflexus mobilis*, which is not a human pathogen, possesses an enzyme that can have such an activity on HMOs. Even more interesting, the expression of the Smob enzyme in *E. coli* cells can result in much higher LNFP-I titers compared to other α-1,2-fucosyltransferases, such as the FucT54 enzyme (Genbank ref. no: WP_013031010.1, also disclosed in WO2019/008133), when expressed in an identical strain background and under the control of the same regulatory elements and at the same gene dosage.

Also, one could expect that the ability to specifically fucosylate LNT and not lactose is a result of an enzyme (e.g. FutC) engineering effort. However, a wild-type enzyme produced by a naturally occurring microorganism that is found in an otherwise unexpected habitat, such as a brackish lake sediment, can show a desired fucosylation specificity towards an HMO molecule, i.e., LNT.

An α-1,2-fucosyl-transferase is responsible for adding a fucose onto the galactose residue of the O-antigen repeating unit via an α-1,2 linkage. The sequence of the protein may be altered without losing the functionality.

The functionality of the Smob α-1,2-fucosyl-transferase is the transfer of a fucosyl moiety from a donor molecule onto a Gal moiety of an acceptor through an α-1,2 coupling. The donor is e.g. GDP-Fucose, if the acceptor molecule is lactose, LNT and/or LNFP-I.

Thus, in one or more exemplary embodiments, the Smob α-1,2-fucosyltransferase or a functional homologue thereof transfers a fucosyl group from GDP-Fucose onto lactose and/or LNT, thus generating 2'-FL and/or LNFP-I (see FIG. 10). In a similar manner, the enzyme transfers a fucosyl group from GDP-Fucose onto lactose, thus generating 2'-FL.

The activity of the Smob α-1,2-fucosyltransferase is higher for the fucosylation of LNT than for lactose.

The Smob α-1,2-fucosyltransferase has a low activity on lactose and a high activity on LNT. Examples of high activity of the Smob α-1,2-fucosyltransferase on LNT and low activity of said α-1,2-fucosyltransferase on lactose is shown in Example 1.

In one or more exemplary embodiments, the recombinant nucleic acid encodes an α-1,2-fucosyltransferase protein as shown in SEQ ID NO: 1, or a functional homologue thereof having an amino acid sequence which is at least 70% identical to SEQ ID NO: 1, such as at least 71% identical, at least 72% identical, at least 73% identical, at least 74% identical, at least 75% identical, at least 76% identical, at least 77% identical, at least 78% identical, at least 79% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical at least 96% identical, at least 97% identical, at least 98% identical, or at least 99% identical.

In one or more presently preferred exemplary embodiments, the amino acid sequence is at least 75% identical to SEQ ID NO: 1.

Sequence Identity

The term "sequence identity of [a certain] %" in the context of two or more nucleic acid or amino acid sequences means that the two or more sequences have nucleic acids or amino acid residues in common in the given percent, when compared and aligned for maximum correspondence over a comparison window or designated sequences of nucleic acids or amino acids (i.e. the sequences have at least 90 percent (%) identity). Percent identity of nucleic acid or amino acid sequences can be measured using a BLAST 2.0 sequence comparison algorithm with default parameters, or by manual alignment and visual inspection (see e.g. http://www.ncbi.nlm.nih.gov/BLAST/). This definition also applies to the complement of a test sequence and to sequences that have deletions and/or additions, as well as those that have substitutions. An example of an algorithm that is suitable for determining percent identity, sequence similarity and for alignment is the BLAST 2.2.20+ algorithm, which is described in Altschul et al. *Nucl. Acids Res.* 25, 3389 (1997). BLAST 2.2.20+ is used to determine percent sequence identity for the nucleic acids and proteins of the disclosure. Software for performing BLAST analyses is publicly available through the National Center for Biotechnology Information (http://www.ncbi.nlm.nih.gov/). Examples of commonly used sequence alignment algorithms are CLUSTAL Omega (www.ebi.ac.uk/Tools/msa/clustalo/),
EMBOSS Needle (www.ebi.ac.uk/Tools/psa/emboss_needle/),
MAFFT (mafft.cbrc.jp/alignment/server/), or
MUSCLE (www.ebi.ac.uk/Tools/msa/muscle/).

Preferably, the sequence identity between two amino acid sequences is determined using the Needleman-Wunsch algorithm (Needleman and Wunsch, 1970, J. Mol. Biol. 48:443-453) as implemented in the Needle program of the EMBOSS package (EMBOSS: The European Molecular Biology Open Software Suite, Rice et al., 2000, Trends Genet. 16:276-277), preferably version 5.0.0 or later (available at https://www.ebi.ac.uk/Tools/psa/emboss needle/). The parameters used are gap open penalty of 10, gap extension penalty of 0.5, and the EBLOSUM62 (EMBOSS version of 30 BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment).

Preferably, the sequence identity between two nucleotide sequences is determined using the Needleman-Wunsch algorithm (Needleman and Wunsch, 1 970, supra) as implemented in the Needle program of the EMBOSS package (EMBOSS: The European Molecular Biology Open Software Suite, Rice et al., 2000, Trends Genet. 16:276-277), preferably version 5.0.0 or later. The parameters used are gap open penalty of 10, gap extension penalty of 0.5, and the DNAFULL (EMBOSS version of NCBI NUC4.4) substitution matrix. The output of Needle labeled "longest identity" (obtained using the -nobrief option) is used as the percent identity and is calculated as follows: (Identical Deoxyribonucleotides×100)/(Length of Alignment−Total Number of Gaps in Alignment).

Functional Homologue

A functional homologue of a protein/nucleotide as described herein is a protein/nucleotide with alterations in the genetic code, which retain its original functionality. A functional homologue may be obtained by mutagenesis. The functional homologue should have a remaining functionality of at least 50%, such as 60%, 70%, 80%, 90% or 100% compared to the functionality of the protein/nucleotide.

A functional homologue of any one of the disclosed amino acid sequences can also have a higher functionality. A functional homologue as described herein is able to participate in the HMO production, in terms of HMO yield, purity, reduction in biomass formation, viability of the genetically engineered cell, robustness of the genetically engineered cell, or reduction in consumables.

A Method for Producing One or More Human Milk Oligosaccharide (HMO)

When applying the Smob α-1,2-fucosyltransferases in industrial production, one is able to achieve higher conversion rates in the enzymatic production of complex HMOs.

Thus, in one or more exemplary embodiments, the present disclosure relates to a method for producing one or more human milk oligosaccharide (HMO) comprising the steps of, a) providing a genetically engineered cell capable of producing an HMO, wherein said cell comprises a recombinant nucleic acid encoding an α-1,2-fucosyltransferase protein as shown in SEQ ID NO: 1, or a functional homologue thereof having an amino acid sequence which is at least 70% identical to SEQ ID NO: 1,
b) culturing the cell according to (a) in a suitable cell culture medium to express said nucleic acid; and
c) harvesting the HMO(s) produced in step (b).

In one embodiment, the one or more HMOs contains a least one fucosylated HMO, preferably selected from the group consisting of 2'-FL, LNFP-I and DFL.

In another embodiment the one or more HMOs contains a least one fucosylated HMO, preferably selected from the group consisting of 2'-FL, LNFP-I and LNDFH-I.

In a preferred embodiment the method predominantly produces LNFP-1, meaning that more than 70% of the total HMO produced is LNFP-I. In the context of the present invention LNFP-I can also be termed the HMO product or major HMO.

Human Milk Oligosaccharide (HMO)

In the context of the disclosure, the term "oligosaccharide" means a saccharide polymer containing a number of monosaccharide units. In some embodiments, preferred oligosaccharides are saccharide polymers consisting of three, four, five or six monosaccharide units, i.e. trisaccharides, tetrasaccharides, pentasaccharides or hexasaccharides. Preferable oligosaccharides of the disclosure are human milk oligosaccharides (HMOs).

The term "human milk oligosaccharide" or "HMO" in the present context means a complex carbohydrate found in human breast milk. The HMOs have a core structure comprising a lactose unit at the reducing end that can be elongated by one or more β-N-acetyl-lactosaminyl and/or one or more β-lacto-N-biosyl units, and this core structure can be decorated by one or more α-L-fucopyranosyl and/or α-N-acetyl-neuraminyl (sialyl) moieties.

In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-triose II (LNT-II) lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-I), lacto-N-difucohexaose I (LNDFH-I), 3-fucosyllactose (3'-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), 3'-O-sialyllacto-N-tetraose a (LST a), fucosyl-LST a (FLST a), 6'-O-sialyllacto-N-tetraose b (LST b), fucosyl-LST b (FLST b), 6'-O-sialyllacto-N-neotetraose (LST c), fucosyl-LST c (FLST c), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DS-LNT).

In the context of the present disclosure lactose is not regarded as an HMO species.

One or More HMO(s)

By the term "one or more HMOs" is meant that an HMO production cell may be able to produce a single HMO structure (a first HMO) or multiple HMO structures (a second, a third, etc. HMO). Multiple HMO structures from one cell is in particular the case when the cell contains more than one glycosyl transferase, since this often leads to HMO by-product formation. Typically, by-product HMOs are either the major HMO precursors or products of further modification of the major HMO. In some embodiments, it may be desired to produce the product HMO in predominant amounts and by-product HMOs in minor amounts. Cells and methods for HMO production described herein allow for controlled production of an HMO product with a defined HMO profile, e.g., in one embodiment, the produced HMO mixture wherein the product HMO is a dominating HMO compared to the other HMOs (i.e. by-product HMOs) of the mixture, i.e. the product HMO is produced in higher amounts than other by-product HMOs; in other embodiments, the cell producing the same HMO mixture may be tuned to produce one or more by-product HMOs in higher amount than product HMO. For example, during the production of the major HMO LNFP-I, often a significant amount of 2'-FL and some DFL, LNT-II, LNT, and potentially also LNnH, parα-LNH are present after fermentation, these can be considered by-product HMO, but may also be desired as part of the final HMO product. With the genetically modified cells of the present invention the level of 2'-FL in the LNFP-I product can be significantly reduced.

Human Milk Oligosaccharide (HMO) Blend The term "blend" or "HMO blend" refers to a mixture of two or more HMOs and/or HMO precursors, such as but not limited to HMOs selected from LNT-II, LNT, LNnT, LNH, LNnH, p-LNH, p-LNnH, 2'-FL, 3FL, DFL, LNFP-I, LNFP-II, LNFP-III, LNFP-V, F-LNnH, DF-LNH I, DF-LNH II, DF-LNH I, DF-para-LNH, DF-para-LNnH, 3'-SL, 6'-SL, FSL, F-LST a, F-LST b, F-LST c, LST a, LST b, LST c and DS-LNT.

In some exemplary embodiments, it may be preferred that a genetically engineered cell produces a single HMO, in other preferred exemplary embodiments, a genetically engineered cell producing multiple HMO structures may be preferred.

In some exemplified embodiments, it may be desired to produce the predominant HMO or HMOs in abundant amounts and by-product HMOs in minor amounts.

In one or more exemplary embodiments, the method produces one or more fucosylated human milk oligosaccharide(s) (HMO(s)). In the context of the present invention this means comprising one or more fucosylated HMOs and it is understood that the production of one or more fucosylated HMOs does not rule out the presence of other HMO's such as neutral core HMO's, like LNT-II and LNT produced as by-product HMOs in the fermentation process.

In one or more exemplary embodiments, the method may produce one or more HMOs selected from the group consisting of 2'-FL, LNT-II, LNT, LNFP-I, LNDFH-I and DFL.

In one or more exemplary embodiments, the method may produce one or more fucosylated HMOs selected from the group consisting of 2'-FL, LNFP-I, LNDFH-I and DFL. Preferably, at least LNFP-I is present.

In one or more exemplary embodiments, the method may produce one or more HMOs, wherein the one or more HMOs are 2'-FL, DFL, LNT-II, LNT and LNFP-I.

In one or more exemplary embodiments, the method may produce one or more HMOs, wherein the one or more HMOs are 2'-FL, DFL, LNT and LNFP-I.

In one or more exemplary embodiments, the method may produce one or more HMOs, wherein the one or more HMOs are LNFP-I and potentially one or more of 2'-FL, LNT-II and/or LNT.

In one or more exemplary embodiments, the method may produce one or more HMOs, wherein the one or more HMOs are LNFP-I and potentially one or more of 2'-FL, DFL and/or LNT.

In one or more exemplary embodiments, the method may produce one or more HMOs, wherein the one or more HMOs are LNFP-I and LNT.

In one or more exemplary embodiments, the method may produce one or more HMOs, wherein the one or more HMOs are LNFP-I and 2'-FL.

Predominant HMO

The term "predominant" is used herein to define a single HMO species being more than 70 molar % of the total amount of harvested HMOs, such as but not limited to more than 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5%. The same definition applies to a blend of HMOs, meaning that a blend of for example two HMOs are "predominant", when the blend is more than 70% of the total amount of harvested HMOs.

In one or more exemplary embodiments, the method may produce one or more HMOs, wherein the predominant HMOs produced are LNFP-I, 2'-FL and/or LNT.

In one or more exemplary embodiments, the method produces one or more HMOs, wherein the predominant HMO produced is LNFP-I. Specifically, LNFP-I is produced in more than 70 molar % of the total HMO, such as more than 75%, such as more than 80%, such as more than 85%, such as more than 90%, such as more than 95 molar % of the total HMO.

In one or more exemplary embodiments, the method produces one or more HMOs, wherein the predominant HMO produced is a blend of LNT and LNFP-I.

In one or more exemplary embodiments, the method may produce one or more HMO, wherein the predominant HMOs produced is a blend of 2'-FL and LNFP-I.

In one or more exemplary embodiments, the method may produce one or more HMOs, wherein the predominant HMOs produced is a blend of LNFP-I and LNT-II.

LNFP-I as the Predominant HMO

One objective with the present disclosure is to achieve higher LNFP-I titers, while GDP-fucose and lactose are not exclusively used in the 2'-FL biosynthetic route, but remain available for and are directed to the LNFP-I route instead. This facilitates the development of an industrial process towards the production of LNFP-I by fermentation, since the HMO profile acquired in the end of the fermentation consists almost exclusively of LNFP-I. One advantage of the method described herein is therefore that production of LNFP-I by fermentation is enabled with only minimal levels of 2-'FL being formed by the producing cell.

In one or more presently preferred exemplary embodiments, the predominant HMO produced is LNFP-I. Specifically, LNFP-I is produced in more than 70 molar % of the total HMO, such as more than 75%, such as more than 80%, such as more than 85%, such as more than 90%, such as more than 95 molar % of the total HMO.

Lacto-N-fuco-pentaose I (LNFP-I) is a pentasaccharide, more precisely, a neutral fucosylated pentasaccharide composed of fucose, galactose, N-acetylglucosamine, galactose, and glucose (Fucα1-2Galβ1-3GlcNAcβ1-3Galβ1-4Glc). It is naturally present in human milk. LNFP-I supports immune health via inhibition of pathogen adherence to the intestinal cell wall and antimicrobial effects via binding to toxins. LNFP-I also has a positive impact on growth of bifidobacteria, which are beneficial for gut health.

The production of predominantly LNFP-I is particularly challenging in large scale, yet the present disclosure provides an effective means for the production of predominantly LNFP-I.

As seen from the Examples section and in particular FIG. 5, the Smob α-1,2-fucosyltransferase shows high specificity for LNT and simultaneously very low specificity for lactose, as revealed by the high-level LNFP-I production and the very low titers of other HMOs detected in smob-expressing cells. Thus, the genetically engineered cells shown herein expressing the two glycosyltransferases (β-1,3-N-acetylglucosaminyltransferase and β-1,3-Galactosyltransferase) required for LNT synthesis and in addition the Smob enzyme produce almost exclusively LNFP-I.

In one or more exemplary embodiments, the LNFP-I molar % fraction in the final HMO blend is more than 70%, such as but not limited to, more than 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5%.

In this manner, the present disclosure demonstrates an *E. coli* strain, that already produces LNT, can be advantageously employed to either increase the LNFP-I content of neutral HMO blends or establish an in vivo production process that results in an almost "pure" LNFP-I HMO product or at least a high-ratio LNFP-I:HMO by-product.

Thus, in one or more exemplary embodiments, the methods described herein relates to the production of one or more HMOs, wherein the harvested HMOs contain 80-99.9%, preferably 90-99.9% LNFP-I.

Performance Evaluation

In one or more exemplary embodiments, the performance of the engineered HMO producing strains are evaluated two-fold. Firstly, overall productivity is assessed by the % change in HMO titer of one or more given HMO(s), measured as concentrations under comparable culture conditions. Secondly, quality of a given product composition was assessed by the ratio between a specific target HMO and another specific HMO by-products or the ratio between the target HMO and the sum of all HMOs. HMO ratios are in all instances given as molar ratios, either in the form of an absolute ratio as x:y or as a relative ratio given in %. For the purpose of the present invention lactose is not considered an HMO.

Other HMOs

2'-FL

2'-Fucosyllactose (2'-FL or 2'O-fucosyllactose) is a trisaccharide, more precisely, fucosylated, neutral trisaccharide composed of L-fucose, D-galactose, and D-glucose units (Fucα1-2Galβ1-4Glc). It is the most prevalent human milk oligosaccharide (HMO) naturally present in human breast milk, making up about 30% of all of HMOs. In a genetically engineered cell or in an enzymatic reaction, 2'-FL is produced primarily by an α-1,2-fucosyltranferase enzymatic reaction with lactose and a fucosyl donor.

In one or more exemplary embodiments, a HMO produced by the methods described herein is 2'-Fucosyllactose.

LNT-II

Lacto-N-triose II (LNT-II) is a trisaccharide, more precisely, a neutral trisaccharide composed of N-acetylglucosamine, galactose, and glucose (GlcNAcβ1-3Galβ1-4Glc). It is naturally present in human milk.

In one or more exemplary embodiments, a HMO produced by the methods described herein is Lacto-N-triose II.

LNT

Lacto-N-tetraose (LNT) is a tetrasaccharide, more precisely, a neutral tetrasaccharide composed of galactose, N-acetylglucosamine, galactose, and glucose (Galβ1-3GlcNAcβ1-3Galβ1-4Glc). It is naturally present in human milk.

In one or more exemplary embodiments, a HMO produced by the methods described herein is Lacto-N-tetraose.

In one or more exemplary embodiments, the method may produce one or more HMOs, wherein the predominant HMO produced is LNT.

DFL

Difucosyllactose (DFL or 2',3-di-O-fucosyllactose) is tetrasaccharide, more precisely a fucosylated neutral tetrasaccharide composed of L-fucose, D-galactose, L-fucose, and D-glucose (Fucα1-2GalB1-4(Fucα1-3)Glc). It is naturally present in human milk.

HMO Blend Molar Ratios

The HMO products produced by the methods disclosed herein can also be given in ratios. The "ratio" as described herein is understood as the molar ratio between two HMOs or between one HMO and the sum of other HMOs. HMO ratios are in all instances given as molar ratios, either in the form of an absolute ratio as x:y or as a relative ratio given in %.

Thus, in one or more exemplary embodiments, the molar ratio of LNFP-I:2'-FL harvested in step c) is in the range of 20:1-1:1, such as but not limited to 15:1, 10:1, 5:1, 1:1 or 2'-FL is absent from said product.

In one or more exemplary embodiments, the molar ratio of LNFP-I:LNT harvested in step c) is in the range of 1000:1 to 1:1, such as but not limited to 100:1, 80:1, 50:1, 25:1, 15:1, 10:1, 5:1, 1:1 or LNT is absent from said product.

The Molar Ratio of LNFP-1:2'-FL in the Harvested HMOs

In one or more exemplary embodiments, the molar ratio of LNFP-I:2'-FL in the harvested HMOs in step c) according to the method, or in the final product is in the range of 15:1-2:1.

In one or more exemplary embodiments, the molar ratio of LNFP-I:2'-FL in the harvested HMOs in step c) according to the method, or in the final product is in the range of 15:1-3:1, such as in the range 14:1 to 7:1, such as in the range 13:1 to 9:1.

In one or more exemplary embodiments, the molar ratio of LNFP-I:2'-FL in the harvested HMOs in step c) according to the method, is in the range of 15:1 to 10:1, such as in the range 14:1 to 11:1, such as in the range 13:1 to 12:1.

In one or more exemplary embodiments, the molar ratio of LNFP-I:2'-FL in the harvested HMOs in step c) according to the method, is 10:1, 5:1, or 3:1.

The Ratio of LNFP-I:LNT in the Harvested HMOs

In one or more exemplary embodiments, the molar ratio of LNFP-I:LNT in the harvested HMOs in step c) according to the method is in the range of 1000:1 to 10:1.

In one or more exemplary embodiments, the molar ratio of LNFP-I:LNT in the harvested HMOs in step c) according to the method is in the range of 500:1 to 100:1.

In one or more exemplary embodiments, the molar ratio of LNFP-I:LNT in the harvested HMOs in step c) according to the method is in the range of 800:1 to 200:1.

In one or more exemplary embodiments, the molar ratio of LNFP-I:LNT in the harvested HMOs in step c) according to the method is in the range of 1000:1 to 500:1.

In one or more exemplary embodiments, the molar ratio of LNFP-I:LNT in the harvested HMOs in step c) according to the method, is in the range of 950:1 to 750:1.

In an exemplified embodiment, the molar ratio of LNFP-I:LNT in the harvested HMOs in step c) according to the method of the invention, is 100:1, 80:1, 50:1, or 10:1.

In another exemplified embodiment, the molar ratio of LNFP-I:LNT in the harvested HMOs in step c) according to the method of the invention, is in the range of 90:1 to 11:1.

In another exemplified embodiment, the molar ratio of LNFP-I:LNT in the harvested HMOs in step c) according to the method of the invention, is in the range of 50:1 to 20:1.

In another exemplified embodiment, the molar ratio of LNFP-I:LNT in the harvested HMOs in step c) according to the method of the invention, is above 10:1, but below 100:1, such as above 20:1, but below 90:1 or such as above 50:1, but below 99:1.

In another exemplified embodiment, the molar ratio of LNFP-I:LNT in the harvested HMOs in step c) according to the method of the invention, is above 10:1, but below 100:1, such as above 15:1, but below 50:1 or such as above 20:1, but below 40:1.

Absent HMOs

In one or more exemplary embodiments, LNT-II is absent from the harvested HMOs.

An HMO is considered absent from the harvested HMOs in step c) in the methods described herein, when the amount of said HMO constitute less than 1% of the total amount of harvested HMOs, such as but not limited to less than 0.9%, less than 0.1%, less than 0.01%, less than 0.001% of the total amount of harvested HMOs.

In one or more exemplary embodiments, 2'-FL and/or LNT-II and/or LNT and/or LNDFH-I and/or DFL is absent.

In one or more exemplary embodiments, LNT-II and/or LNT is absent.

In one or more exemplary embodiments, 2'-FL and/or LNDFH-I and/or DFL is absent.

Culturing

In the present context, culturing refers to the process by which cells are grown under controlled conditions, generally outside their natural environment, thus a method used to cultivate, propagate and grow a large number of cells.

Cell Culture Medium

In the present context, a growth medium or culture medium is a liquid or gel designed to support the growth of microorganisms, cells, or small plants. The medium comprises an appropriate source of energy and may comprise compounds which regulate the cell cycle. The culture medium may be semi-defined, i.e. containing complex media compounds (e.g. yeast extract, soy peptone, casamino acids, etc.), or it may be chemically defined, without any complex compounds. Exemplary suitable media are provided in experimental examples.

In one or more exemplary embodiments, the culture media is minimal media.

In one or more exemplary embodiments, the culture media is supplemented with one or more energy and carbon sources selected form the group containing lactose, glycerol, sucrose, glucose and fructose.

In one or more exemplary embodiments, the culturing media is supplemented with one or more energy and carbon sources selected form the group containing glycerol, sucrose and glucose.

In one or more exemplary embodiments, the culturing media is supplemented with glycerol, sucrose and/or glucose.

In one or more exemplary embodiments, the culturing media is supplemented with glycerol and/or glucose.

In one or more exemplary embodiments, the culturing media is supplemented with sucrose and/or glucose.

In one or more exemplary embodiments, the culturing media is supplemented with glycerol and/or sucrose.

In one or more exemplary embodiments, the culturing media is supplemented only with sucrose.

In one or more exemplary embodiments, the culturing media contains sucrose as the sole carbon and energy source.

In one or more exemplary embodiments, the culturing media is supplemented only with glucose.

In one or more exemplary embodiments, the culturing media contains glucose as the sole carbon and energy source.

Sucrose Fermentation

Biotechnological industry strives to develop (an) aerobic bioprocesses fueled by abundant and cheap carbon sources, like sucrose, thus in one or more exemplary embodiments, the genetically engineered cell is capable of utilizing sucrose as sole carbon and energy source.

In one or more preferred exemplary embodiment(s), the genetically engineered cell expresses a sucrose utilization system. Such a system can be endogenous to the cell, but it may also be heterologous if the cell is not capable of utilizing sucrose.

In one or more preferred exemplary embodiment(s), the genetically engineered cell comprises one or more heterologous nucleic acid sequence encoding one or more heterologous polypeptide(s), which enables utilization of sucrose as sole carbon and energy source of said genetically engineered cell.

In one or more exemplary embodiments, the genetically engineered cell may comprise a PTS-dependent sucrose utilization transport system and/or a recombinant nucleic acid sequence encoding a heterologous polypeptide capable of hydrolysing sucrose into fructose and glucose.

Such cells are capable of utilizing sucrose as carbon and energy source. For example, the culturing step according to step b) of the method(s) disclosed herein comprises a two-step sucrose feeding, with a second feeding phase by continuously adding to the culture an amount of sucrose that is less than that added continuously in a first feeding phase so as to slow the cell growth and increase the content of product produced in the high cell density culture.

The feeding rate of sucrose added continuously to the cell culture during the second feeding phase may be around 30-40% less than that of sucrose added continuously during the first feeding phase.

During both feeding phases, lactose can be added continuously, preferably with sucrose in the same feeding solution, or sequentially.

Optionally, the culturing further comprises a third feeding phase when considerable amount of unused acceptor remained after the second phase in the extracellular fraction. Then the addition of sucrose is continued without adding the acceptor, preferably with around the same feeding rate set for the second feeding phase until consumption of the acceptor.

In one or more exemplary embodiments, the genetically engineered cell may comprise one or more heterologous nucleic acid sequence encoding one or more heterologous polypeptide(s) which enables utilization of sucrose as sole carbon and energy source of said genetically engineered cell.

In one or more exemplary embodiments, the genetically engineered cell expresses a sucrose utilization system selected from a PTS-dependent sucrose utilization system, further comprising the scrYA and scrBR operons. One PTS-dependent sucrose system is described in WO2015197082.

In one or more exemplary embodiments, the polypeptide encoded by the scrYA operon are polypeptides with an amino acid sequence according to SEQ ID NOs: 9 and 10 [scrY and scrA] or a functional homologue of any one of SEQ ID NOs: 9 and 10 [scrY and scrA], having an amino acid sequence which is at least 80% identical to any one of SEQ ID NO: 9 and 10 [scrY and scrA].

In one or more exemplary embodiments the polypeptide encoded by the scrBR operon are polypeptides with an amino acid sequence according to SEQ ID NOs: 11 and 12 [scrB and scrR] or a functional homologue of any one of SEQ ID NOs: 11 and 12 [scrB and scrR], having an amino acid sequence which is at least 80% identical to any one of SEQ ID NOs: 11 and 12 [scrB and scrR].

In one or more preferred exemplary embodiment(s), the genetically engineered cell expresses a sucrose utilization system selected from a polypeptide capable of hydrolysing sucrose into glucose and fructose. Preferably, polypeptide capable of hydrolysing sucrose into glucose and fructose is a single heterologous enzyme.

In one or more exemplary embodiments, the polypeptide capable of hydrolyzing sucrose into fructose and glucose is selected from the group consisting of SEQ ID NOs: 13 or 14

[SacC_Agal and Bff], or a functional homologue of any one of SEQ ID NOs: 13 or 14 [SacC_Agal and Bff], having an amino acid sequence which is at least 80% identical, such as at least 85%, such as at least 90%, such as at least 95% identical to any one of SEQ ID NO: 13 or 14 [SacC_Agal and Bff]

ScrB, ScrR, ScrY and ScrA

ScrB is the heterologous polypeptide that is 100% identical to the GenBank ID: WP_000056853.1 or a functional homologue thereof having an amino acid sequence which is at least 80% identical and is a sucrose-6-phosphate hydrolase.

ScrR is the heterologous polypeptide that is 100% identical to the GenBank ID: WP_000851062.1 or a functional homologue thereof having an amino acid sequence which is at least 80% identical and is a sucrose repressor protein.

ScrY is the heterologous polypeptide that is 100% identical to the GenBank ID: CAA40657.1 or a functional homologue thereof having an amino acid sequence which is at least 80% identical and is a sucrose porin.

ScrA is the heterologous polypeptide that is 100% identical to the GenBank ID: CAA40658.1 or a functional homologue thereof having an amino acid sequence which is at least 80% identical and is a sucrose-specific enzyme II.

In the present context a sucrose utilization system is a group of heterologous polypeptides enabling the import and hydrolysis of sucrose into fructose and glucose as well as the DNA-level regulation of the system itself.

Bff or SacC_AgaI

SacC_AagI is the heterologous polypeptide which is 100% identical to the GenBank ID: WP_103853210.1 or a functional homologue thereof having an amino acid sequence which is at least 80% identical, such as at least 85%, such as at least 90%, such as at least 95% identical and is characterized as a glycoside hydrolase, and according to the current disclosure functions as an invertase and/or sucrose hydrolase.

Bff is the heterologous polypeptide that is 100% identical to the GenBank ID: BAD18121.1 or a functional homologue, having an amino acid sequence which is at least 80% identical, such as at least 85%, such as at least 90%, such as at least 95% identical and is a β-fructofuranosidase.

In the present context an invertase or sucrose hydrolase is an enzyme capable of hydrolysing sucrose into fructose and glucose.

Harvesting

The term "harvesting" in the context relates to collecting the produced HMO(s) following the termination of fermentation. In one or more exemplary embodiments it may include collecting the HMO(s) included in both the biomass (i.e. the host cells) and cultivation media, i.e. before/without separation of the fermentation broth from the biomass. In other embodiments, the produced HMOs may be collected separately from the biomass and fermentation broth, i.e. after/following the separation of biomass from cultivation media (i.e. fermentation broth). The definition of step c) is post fermentation.

The separation of cells from the medium can be carried out with any of the methods well known to the skilled person in the art, such as any suitable type of centrifugation or filtration. The separation of cells from the medium can follow immediately after harvesting the fermentation broth or be carried out at a later stage after storing the fermentation broth at appropriate conditions. Recovery of the produced HMO(s) from the remaining biomass (or total fermentation) include extraction thereof from the biomass (i.e the production cells). It can be done by any suitable methods of the art, e.g. by sonication, boiling/heating, homogenization, enzymatic lysis using lysozyme, or freezing and grinding.

After recovery from fermentation, HMO(s) are available for further processing and purification.

Genetically Engineered Cell

The present disclosure relates to a genetically engineered cell comprising a recombinant nucleic acid sequence encoding a smob α-1,2-fucosyltransferase protein as described above. The present disclosure relates further to a genetically engineered cell for use in a method for producing fucosylated oligosaccharides. Said genetically engineered cell has been genetically engineered to express a heterologous fucosyl-transferase, which is capable of transferring a fucose residue from a donor substrate to an acceptor molecule, wherein said acceptor molecule is preferably lacto-N-tetraose.

A "genetically engineered cell" as used herein is understood as a cell which has been transformed or transfected, by a recombinant nucleic acid sequence. Accordingly, a "genetically engineered cell" is in the present context understood as a host cell which has been transformed or transfected by a recombinant nucleic acid sequence.

An aspect of the present invention is a genetically engineered cell comprising a recombinant nucleic acid sequence encoding an α-1,2-fucosyltransferase protein as shown in SEQ ID NO: 1, or a functional homologue thereof having an amino acid sequence which is at least 70%, such as at least 80%, such as at least 90% such as at least 95% identical to SEQ ID NO: 1.

In a further embodiment of the present invention the genetically engineered cell is an LNT producing cell allowing production of LNFP-I from lactose as the substrate. Preferably, the genetically engineered cell further comprises a nucleic acid sequence encoding a β-1,3-N-acetyl-glucosaminyltransferase protein and/or a nucleic acid sequence encoding a β-1,3-galactosyltransferase protein.

To reduce the formation of 2'-FL it may be preferred to increase the β-1,3-N-acetyl-glucosaminyltransferase activity in the cell compared to the fucosyltransferase activity to favour addition of N-acetyl-glucosamine (GlcNAc) to lactose over fucose.

In a further embodiment, the β-1,3-N-acetyl-glucosaminyltransferase expression levels are increased either by increasing the copy number and/or by choosing a strong regulatory element to control the expression.

In a further embodiment, the β-1,3-galactosyltransferase expression levels are increased either by increasing the copy number and/or by choosing a strong regulatory element to control the expression.

In a further embodiment, both the β-1,3-N-acetyl-glucosaminyltransferase and the β-1,3-galactosyltransferase expression levels are increased either by increasing the copy number and/or by choosing a strong regulatory element to control the expression.

In further embodiments of the invention the genetically engineered cell of the present invention may contain further modifications described in the sections below, such as regulatory elements, in particular promoters and activators, repressor deletions, functional enzymes, such as sugar efflux transporters, additional glycosyl transferases, colanic acid pathway modifications etc.

In one or more exemplary embodiments, the cell is capable of producing one or more HMO(s) selected from the group consisting of 2'-FL, LNT-II, LNT, LNFP-I, LNDFH-I and DFL.

In one or more exemplary embodiments, the genetically engineered cell is capable of producing one or more HMO(s) selected from the group consisting of 2'-FL, LNT-II, LNT and LNFP-I.

In one or more exemplary embodiments, the predominant HMO produced by the genetically engineered cell is LNFP-I.

The genetically engineered cell may be any cell useful for HMO production including mammalian cell lines. Preferably, the host cell is a unicellular microorganism of eucaryotic or prokaryotic origin.

Appropriate microbial cells that may function as a host cell include yeast cells, bacterial cells, archaebacterial cells, algae cells, and fungal cells.

The genetically engineered cell (host cell) may be e.g. a bacterial or yeast cell. In one preferred embodiment, the genetically engineered cell is a prokaryotic cell, such as a bacterial cell.

Bacterial Host Cells

Regarding the bacterial host cells, there are, in principle, no limitations; they may be eubacteria (gram-positive or gram-negative) or archaebacteria, as long as they allow genetic manipulation for insertion of a gene of interest and can be cultivated on a manufacturing scale. Preferably, the host cell has the property to allow cultivation to high cell densities. Non-limiting examples of bacterial host cells that are suitable for recombinant industrial production of an HMO(s) according to the invention could be *Erwinia herbicola* (*Pantoea agglomerans*), *Citrobacter freundii*, *Pantoea citrea*, *Pectobacterium carotovorum*, or *Xanthomonas campestris*. Bacteria of the genus Bacillus may also be used, including *Bacillus subtilis*, *Bacillus licheniformis*, *Bacillus coagulans*, *Bacillus thermophilus*, *Bacillus laterosporus*, *Bacillus megaterium*, *Bacillus mycoides*, *Bacillus pumilus*, *Bacillus lentus*, *Bacillus cereus*, *and Bacillus circulans*. Similarly, bacteria of the genera *Lactobacillus* and *Lactococcus* may be engineered using the methods of this invention, including but not limited to *Lactobacillus acidophilus*, *Lactobacillus salivarius*, *Lactobacillus plantarum*, *Lactobacillus helveticus*, *Lactobacillus delbrueckii*, *Lactobacillus rhamnosus*, *Lactobacillus bulgaricus*, *Lactobacillus crispatus*, *Lactobacillus gasseri*, *Lactobacillus casei*, *Lactobacillus reuteri*, *Lactobacillus jensenii*, and *Lactococcus lactis*. *Streptococcus thermophiles* and *Proprionibacterium freudenreichii* are also suitable bacterial species for the invention described herein. Also included as part of this invention are strains, engineered as described here, from the genera *Enterococcus* (e.g., *Enterococcus faecium* and *Enterococcus thermophiles*), *Bifidobacterium* (e.g., *Bifidobacterium longum*, *Bifidobacterium infantis*, and *Bifidobacterium bifidum*), *Sporolactobacillus* spp., *Micromomospora* spp., *Micrococcus* spp., *Rhodococcus* spp., and *Pseudomonas* (e.g., *Pseudomonas fluorescens* and *Pseudomonas aeruginosa*).

Non-limiting examples of fungal host cells that are suitable for recombinant industrial production of an HMO(s) according to the invention could be yeast cells, such as *Komagataella phaffii*, *Kluyveromyces lactis*, *Yarrowia lipolytica*, *Pichia pastoris*, and *Saccaromyces cerevisiae* or filamentous fungi such as *Aspargillus* sp, *Fusarium* sp or *Thricoderma* sp, exemplary species are *A. niger*, *A. nidulans*, *A. oryzae*, *F. solani*, *F. graminearum* and *T. reesei*.

In one or more exemplary embodiments, the genetically engineered cell is *S. cerevisiae* or *P pastoris*.

In one or more exemplary embodiments, the genetically engineered cell is *Pichia pastoris*.

In one or more exemplary embodiments, the genetically engineered cell is *S. cerevisiae*.

In one or more exemplary embodiments, the genetically engineered cell is selected from the group consisting of *E. coli*, *C. glutamicum*, *L. lactis*, *B. subtilis*, *S. lividans*, *P. pastoris*, and *S. cerevisiae*.

In one or more exemplary embodiments, the genetically engineered cell is selected from the group consisting of *B. subtilis*, *S. cerevisiae* and *Escherichia coli*.

In one or more exemplary embodiments, the genetically engineered cell is *B. subtilis*.

In one or more exemplary embodiments, the genetically engineered cell is *Escherichia coli*.

In one or more exemplary embodiments, the invention relates to a genetically engineered cell, wherein the cell is derived from the *E. coli* K-12 strain or DE3.

Controlling the Expression

In the present context the term "controlling the expression" relates to gene expression where the transcription of a gene into mRNA and its subsequent translation into protein is controlled. Gene expression is primarily controlled at the level of transcription, largely as a result of binding of proteins to specific sites on DNA, such as but not limited to regulatory elements.

As described above, engineering strategy can be applied in multiple ways:

1) the copy number
2) the controlling the expression of any copy of these genes at the transcriptional or the translational level
3) the deletion of regulators that repress the expression of key genes in the HMO production process
4) the over-expression of regulators that activate and/or enhance the expression of key genes in the HMO production process Increasing the gene copy number and/or the expression of genes coding the enzymes that are directly involved in the LNFP-I and 2'-FL biosynthetic pathways, including the synthesis of the activated sugars GDP-fucose, UDP-N-acetyl-glucosaminyl and UDP-Gal (donor sugars) and the decoration of lactose, LNT-II and LNT (acceptor sugars) to form, respectively, LNT-II or 2'-FL, LNT, and LNFP-I is desired, in particular LNFP-I.

In one or more exemplary embodiments, the expression of different heterologous and/or native genes I the cell are controlled to achieve the optimal balance increasing either total HMO yield and/or the molar % of the total HMO of one or more selected HMOs, such as LNFP-I Over-Expression A variety of molecular mechanisms ensures that genes are expressed at the appropriate level and under conditions of relevance to the applied production process. For instance, the regulation of transcription can be summarized into the following routes of influence; genetic (direct interaction of a control factor with the gene of interest), modulation and/or interaction of a control factor within the transcriptional machinery and epigenetic (non-sequence changes in DNA structure that influence transcription).

It is known that a reduction in gene expression below a critical threshold for any gene will result in a mutant phenotype, since such a defect essentially mimics either a partial or complete loss of function of the target gene, whereas increased expression of a native gene can be both beneficial or disruptive to a cell or organism.

Over-expression of a gene may be achieved directly by transcriptional activators that bind to key gene regulatory sequences to promote transcription or enhancers that constitute sequence elements positively affecting transcription.

Similarly, direct over-expression of a gene can be achieved by simply increasing its copy number in the genome, or replacing its native promoter with a promoter of higher strength or even modifying the sequence controlling the binding of the corresponding mRNA to the ribosomes, i.e. the Shine-Dalgarno sequence being present upstream of the gene's coding sequence.

Moreover, over-expression of a gene may also be achieved indirectly through the partial or full inactivation of transcriptional repressors that normally bind key regulatory sequences around the coding sequence of the gene of interest and thereby inhibit its transcription.

Thus, in one or more exemplary embodiments, the over-expression of the protein(s) can be is provided by increasing the copy number of the genes coding said protein(s), and/or by choosing an appropriate element for or adding an extra genomic copy, and/or conferring a non-functional (or absent) gene product that normally binds to and repress the expression.

Increasing the Copy Number

Copy number variation is a type of structural variation: specifically, it is a type of duplication or multiplication of a considerable number of base pairs which if representing a protein encoding gene will result in an increase of the number of genes encoding the same protein. Such variation can occur naturally in many species but can also be introduced by genetically modifying a host cell In one or more exemplary embodiments, expression is controlled by increasing the copy number of the desired genes. Copy numbers can be increased either by introducing a plasmid which has a high copy number in the cell or by introducing an additional copy of the gene into the genome of the host cell.

Thus, in one or more exemplary embodiments, the present disclosure relates to a method, wherein the overexpression of the protein(s) is provided by increasing the copy number of the genes coding for said protein(s) and/or by choosing an appropriate regulatory element.

Regulatory Element

The genetically engineered cell may comprise recombinant genes and/or nucleic acids of homologous or heterologous origin. The expression of said recombinant genes and/or nucleic acids can be regulated by one or more nucleic acid sequences comprising a regulatory element.

The term "regulatory element" is to be understood as a regulatory nucleic acid sequence that modulates the expression of a nucleic acid sequence comprising e.g., a coding sequence.

In general, the transcriptional and translational regulatory sequences include, but are not limited to, promoter sequences, ribosomal binding sites, transcriptional start and stop sequences, translational start and stop sequences, and enhancer or activator sequences.

In one or more exemplary embodiments, the expression of the recombinant nucleic acid is regulated by one or more nucleic acid sequences comprising a regulatory element.

In one or more exemplary embodiments, the regulatory element or elements comprise(s) a promoter sequence.

In one or more exemplary embodiments, the recombinant regulatory element comprises more than one promoter sequence, or a recombinant promoter sequence with elements combined from different promoters.

In one or more exemplary embodiments, the recombinant regulatory element comprises a single promoter sequence, suitable for regulating the genes and/or heterologous nucleic acid sequences of the genetically engineered cell of the present invention.

In one or more exemplary embodiments, the recombinant regulatory element comprises two or more regulatory elements with identical promoter sequences suitable for regulating the genes and/or heterologous nucleic acid sequences of the genetically engineered cell of the present invention.

In one or more exemplary embodiments, the recombinant regulatory element comprises two or more regulatory elements with non-identical promoter sequences, suitable for regulating the genes and/or heterologous nucleic acid sequences of the genetically engineered cell of the present invention.

The regulatory architectures i.e., gene-by-gene distributions of transcription-factor-binding sites and identities of the transcription factors that bind those sites can be used multiple different growth conditions and there are more than 100 genes from across the *E. coli* genome, which acts as regulatory elements. Thus, any promoter sequence enabling transcription and/or regulation of the level of transcription, of one or more heterologous or native nucleic acid sequences that encode one or more proteins as described herein may be suitable.

Promoters

The regulatory element or elements, as described above, regulating the expression of the genes and/or nucleic acid sequence(s), may comprise one or more promoter sequence(s), wherein the promoter sequence, is operably linked to the nucleic acid sequence of the gene of interest in that sense regulating the expression of the nucleic acid sequence of the gene of interest.

The term "operably linked" as used herein, refers to a functional relationship between two or more nucleic acid (e.g., DNA) segments. Operably linked refers to the functional relationship of a transcriptional regulatory sequence (such as a promoter sequence, signal sequence, or array of transcription factor binding sites) to a transcribed sequence. For example, a promoter sequence is operably linked to a coding sequence if it stimulates or modulates the transcription of the coding sequence in an appropriate host cell or other expression system. Accordingly, the term "promoter sequence" designates DNA sequences which usually "precede" a gene in a DNA polymer and provide a site for initiation of the transcription into mRNA. "Regulator" DNA sequences, also usually "upstream" of (i.e., preceding) a gene in a given DNA polymer, bind proteins that determine the frequency (or rate) of transcriptional initiation. Collectively referred to as "promoter/regulator sequence" or "control" DNA sequence, these sequences which precede a selected gene (or series of genes) in a functional DNA polymer cooperate to determine whether the transcription (and eventual expression) of a gene will occur. DNA sequences which "follow" a gene in a DNA polymer and provide a signal for termination of the transcription into mRNA are referred to as transcription "terminator" sequences.

Generally, promoter sequences that are operably linked to a transcribed sequence are physically contiguous to the transcribed sequence, i.e., they are cis-acting.

The regulatory element, such as a promoter, controls the expression of the mentioned glycosyltransferases, transporters and the colanic acid gene cluster, and this regulatory element should precede the coding sequence of the construct (promoter/regulatory element+coding sequence). The construct may be integrated into the genome, or it can be introduced into the cell in the form of a plasmid or another episomal element.

The promoter may be of heterologous origin, native to the genetically modified cell or it may be a recombinant promoter, combining heterologous and/or native elements. In general, a promoter may comprise native, heterologous and/or synthetic nucleic acid sequences, and may be a recombinant nucleic acid sequence, recombining two or more nucleic acid sequences or same or different origin as described above, thereby generating a homologous, heterologous or synthetic nucleic promoter sequence, and/or a homologous, heterologous or synthetic nucleic regulatory element.

example of a weak promoter is Plac which when induced with IPTG has an activity of approximately 2300 MU. Table 4 below illustrates various suitable promoters of the invention sorted according to strength relative to the PglpF promoter.

Alternatively, if there is a need for balancing the expression level of one or more proteins to optimize the production it may be beneficial to use a promoter with the desired strength, e.g., middle or low strength.

TABLE 4

Selected promoter sequences

| Promoter name | % Activity relative to PglpF* | Strength | Reference | Seq ID in appl. |
|---|---|---|---|---|
| PmglB_70UTR_SD8 | 291% | high | WO2020255054 | 15 |
| PmglB_70UTR_SD10 | 233-281% | high | WO2020255054 | 16 |
| PmglB_54UTR | 197% | high | WO2020255054 | 17 |
| Plac_70UTR | 182-220% | high | WO2019123324 | 18 |
| PmglB_70UTR_SD9 | 180-226% | high | WO2020255054 | 19 |
| PmglB_70UTR_SD4 | 153%-353% | high | WO2020255054 | 20 |
| PmglB_70UTR_SD5 | 146-152% | high | WO2020255054 | 21 |
| PglpF_SD4 | 140-161% | high | WO2019123324 | 22 |
| PmglB_70UTR_SD7 | 127-173% | high | WO2019123324 | 23 |
| PmglB_70UTR | 124-234% | high | WO2020255054 | 24 |
| PglpA_70UTR | 102-179% | high | WO2019123324 | 25 |
| PglpT_70UTR | 102-240% | high | WO2019123324 | 26 |
| PglpF | 100% | high | WO2019123324 | 27 |
| PglpF_SD10 | 88-96% | high | WO2019123324 | 28 |
| PglpF_SD5 | 82-91% | high | WO2019123324 | 29 |
| PglpF_SD8 | 81-82% | high | WO2019123324 | 30 |
| PmglB_16UTR | 78-171% | high | WO2019123324 | 31 |
| PglpF_SD9 | 73-93% | middle | WO2019123324 | 32 |
| PglpF_SD7 | 47-57% | middle | WO2019123324 | 33 |
| PglpF_SD6 | 46-47% | middle | WO2019123324 | 34 |
| PglpA_16UTR | 38-64% | middle | WO2019123324 | 35 |
| Plac_wt* | 15-28% | low | WO2019123324 | 36 |
| PglpF_SD3 | 9% | low | WO2019123324 | 37 |
| PglpF_SD1 | 5% | low | WO2019123324 | 38 |
| PglpF_B28 | | Not assessed | | 39 |

*The promoter activity is assessed in the LacZ assay described below with the PglpF promoter run as positive reference in the same assay. To compare across assays the activity is calculated relative to the PglpF promoter, a range indicates results from multiple assays One way to increase the production of a product may be to regulate the production of the desired enzyme activity used to produce the product, such as the glycosyltransferases, transporters or enzymes involved in the biosynthetic pathway of the glycosyl donor.

Increasing the promoter strength driving the expression of the desired enzyme may be one way of doing this. The strength of a promoter can be assed using a lacZ enzyme assay where β-galactosidase activity is assayed as described previously (see e.g. Miller J. H. *Experiments in molecular genetics*, Cold spring Harbor Laboratory Press, NY, 1972). Briefly the cells are diluted in Z-buffer and permeabilized with sodium dodecyl sulfate (0.1%) and chloroform. The LacZ assay is performed at 30° C. Samples are preheated, the assay initiated by addition of 200 μl ortho-nitro-phenyl-β-galactosidase (4 mg/ml) and stopped by addition of 500 μl of 1 M $Na_2CO_3$ when the sample had turned slightly yellow. The release of ortho-nitrophenol is subsequently determined as the change in optical density at 420 nm. The specific activities are reported in Miller Units (MU) [A420/(min*ml*A600)]. A regulatory element with an activity above 10,000 MU is considered strong and a regulatory element with an activity below 3,000 MU is considered weak, what is in between has intermediate strength. An example of a strong regulatory element is the PglpF promoter with an activity of approximately 14.000 MU and an In embodiments of the invention the expression of selected nucleic acid sequences of the present invention is under control of a PglpF (SEQ ID NO: 27) or Plac (SEQ ID NO: 36) or PmglB_UTR70 (SEQ ID NO: 24) or PglpA_70UTR (SEQ ID NO: 25) or PglpT_70UTR (SEQ ID NO: 26) or variants of these promoters as identified in Table 5.

Specific PglpF variants can be selected from the group consisting of SEQ ID NO: 22, 28, 29, 30, 32, 33 or 34. A specific Plac variant is SEQ ID NO: 28. Specific PmglB_70UTR variants can be selected from the group consisting of SEQ ID NO: 15, 16, 17, 19, 20, 21, 23 or 31.

Further suitable variants of PglpF, PglpA_70UTR, PglpT_70UTR and PmglB_70UTR promoter sequences are described in or WO2019/123324 and WO2020/255054 respectively (hereby incorporated by reference).

In one or more exemplary embodiments, the regulatory element is a promoter with high or middle strength, such as a promoter sequence selected from the group consisting of PmglB_70UTR_SD8, PmglB_70UTR_SD10, PmglB_54UTR, Plac_70UTR, PmglB_70UTR_SD9, PmglB_70UTR_SD4, PmglB_70UTR_SD5, PglpF_SD4, PmglB_70UTR_SD7, PmglB_70UTR, PglpA_70UTR, PglpT_70UTR, pgatY_70UTR, PglpF, PglpF_SD10, PglpF_SD5, PglpF_SD8, PglpF_B28, PglpF_B29, PmglB_16UTR, PglpF_SD9, PglpF_SD7, PglpF_SD6 and PglpA_16UTR In on referred embodiment the promoter is a strong promoter selected from the group consisting of PmglB_70UTR_SD8, PmglB_70UTR_SD10, PmglB_54UTR, Plac_70UTR, PmglB_70UTR_SD9, PmglB_70UTR_SD4, PmglB_70UTR_SD5, PglpF_SD4, PmglB_70UTR_SD7, PmglB_70UTR, PglpA_70UTR, PglpT_70UTR, pgatY_70UTR, PglpF, PglpF_SD10, PglpF_SD5, PglpF_SD8, and PmglB_16UTR. This may in particular be advantageous for the expression the glycosyltransferases.

In another embodiment the promoter is selected from the group consisting of promoters with middle strength, such as PglpF_SD9, PglpF_SD7, PglpF_SD6 and PglpA_16UTR.

In another embodiment the promoter is selected from the group consisting of promoters with low strength, such as Plac_wt. PglpF_SD3 and PglpF_SD1.

In one or more exemplary embodiments, the regulatory element for the regulation of the expression of a recombinant nucleic acid sequence construct of the present disclosure is the glpFKX operon promoter sequence, PglpF.

In a presently preferred embodiment, the promoter sequence is PglpF.

In one or more exemplary embodiments, the promoter sequence is selected from the group consisting of PBAD, Ptet, Pxyl, PsacB, PxylA, PrpR, PnitA, PT7, Ptac, PL, PR, PnisA, Pb, PgatY_70UTR, PglpF, PglpF_SD1, PglpF_SD10, PglpF_SD2, PglpF_SD3, PglpF_SD4, PglpF_SD5, PglpF_SD6, PglpF_SD7, PglpF_SD8, PglpF_SD9, PglpF_B28, Plac_16UTR, Plac, PmglB_70UTR and PmglB_70UTR_SD4.

In one or more exemplary embodiments, the promoter sequence is selected from the group consisting of PglpF, PglpF_SD1, PglpF_SD10, PglpF_SD2, PglpF_SD3, PglpF_SD4, PglpF_SD5, PglpF_SD6, PglpF_SD7, PglpF_SD8, PglpF_SD9 and PglpF_B28.

In one or more exemplary embodiments, the promoter sequence is selected from the group consisting of PglpF and PglpF_B28. PglpF_B28 is an engineered version of the PglpF sequence comprising an engineered ribosomal binding site sequence downstream of the promoter sequence.

Apart from nucleic acid(s) encoding glycosyltransferase(s), the coding sequence may also comprise one or more recombinant nucleic acid(s) encoding one or more gene regulatory proteins and/or metabolic enzymes of the production host organism and/or a native or heterologous sugar efflux transporter and/or proteins enabling the utilization of sucrose as a carbon and energy source.

Repressors

In one or more exemplary embodiment(s), the genetically engineered cell disclosed herein comprises a non-functional or absent gene product that normally binds to a regulatory element and represses the expression of any of the proteins of the present disclosure regulated by said regulatory element.

The term a non-functional (or absent) gene product that normally binds to and represses the expression driven by the regulatory element in the present context relates to DNA binding sites upstream of the coding sequence of a gene of interest and specifically at the promoter region of said gene.

In one or more exemplary embodiments, the cell may have a non-functional (or absent) gene product(s) that would normally bind to and repress the expression of the α-1,2-fucosyl-transferase protein as shown in SEQ ID NO: 1 or regions upstream of the regulatory element for controlling the expression of the α-1,2-fucosyl-transferase protein as shown in SEQ ID NO: 1.

In one or more exemplary embodiments, said gene product is the DNA-binding transcriptional repressor GlpR.

GlpR

GlpR belongs to the DeoR family of transcriptional regulators and acts as the repressor of the glycerol-3-phosphate regulon, which is organized in different operons. This regulator is part of the glpEGR operon, yet it can also be constitutively expressed as an independent (glpR) transcription unit. In addition, the operons regulated are induced when *Escherichia coli* is grown in the presence of inductor, glycerol, or glycerol-3-phosphate (G3P), and the absence of glucose. In the absence of inductor, this repressor binds in tandem to inverted repeat sequences that consist of 20-nucleic acid-long DNA target sites.

The term "non-functional or absent" in relation to the glpR gene refers to the inactivation of the glpR gene by complete or partial deletion of the corresponding nucleic acid sequence from the bacterial genome (e.g. SEQ ID NO: 42 or variants thereof encoding glpR capable of downregulating glpF derived promoters). The glpR gene encodes the DNA-binding transcriptional repressor GlpR. In this way promoter sequences of the PglpF family are more active in the genetically engineered cell, due to deletion of the repressor gene that would otherwise reduce the transcriptional activity associated with the PglpF promoters.

In one or more exemplary embodiments, the glpR gene is deleted.

The deletion of the glpR gene could eliminate the GlpR-imposed repression of transcription from all PglpF promoters in the cell and in this manner enhance gene expression from all PglpF-based cassettes.

Activators

In one or more exemplary embodiment(s), the genetically engineered cell disclosed herein comprises an over-expressed gene product that enhances the expression of any of the proteins of the present disclosure regulated by said regulatory element.

In one or more exemplary embodiments, the cell of the present disclosure may comprise an over-expressed gene product that enhances the expression of the α-1,2-fucosyl-transferase protein as shown in SEQ ID NO: 1 or regions upstream of the regulatory element for controlling the expression of the α-1,2-fucosyl-transferase protein as shown in SEQ ID NO: 1.

In one or more exemplary embodiments, said gene product is the cAMP DNA-binding transcriptional dual regulator CRP.

CRP

CRP belongs to the CRP-FNR superfamily of transcription factors. CRP regulates the expression of several of the *E. coli* genes, many of which are involved in catabolism of secondary carbon sources. Upon activation by cyclic-AMP, (cAMP) CRP binds directly to specific promoter sequences, the binding recruits the RNA polymerase through direct interaction, which in turn activates the transcription of the nucleic acid sequence following the promoter sequence leading to expression of the gene of interest. Thus, over-expression of CRP may lead to an enhanced expression of a gene/nucleic acid sequence of interest. Amongst other functions, CRP exerts its function on the PglpF promoters, where it contrary to the repressor GlpR, activates promoter sequences of the PglpF family. In this way, over-expression of CRP in the genetically engineered cell of the present disclosure, promotes expression of genes that are regulated by promoters of the PglpF family.

Thus, in one or more exemplary embodiments, the crp gene is over-expressed.

Genetic engineering of GlpR and/or CRP, as suggested in the present disclosure, in 2'-FL producing strains is beneficial for the overall production of 2'-FL by these strains.

Nucleic Acid Constructs

An aspect of the present disclosure is the provision of a nucleic acid construct comprising a heterologous nucleic acid sequence(s) encoding an α-1,2-fucosyl-transferase protein as shown in SEQ ID NO: 1, or a functional homologue thereof having an amino acid sequence which is at least 70% identical, such as at least 80%, such as at least 85%, such as at least 90%, such as at least 95% identical to SEQ ID NO: 1.

In one or more exemplary embodiments, the nucleic acid construct comprising a recombinant nucleic acid sequence which is at least 70% identical to SEQ ID NO: 2, such as more than 80%, such as more than 85%, such as more than 90%, such as more than 95% or such as more than 99% identical to SEQ ID NO: 2.

In an exemplified embodiment, the nucleic acid construct comprising a recombinant nucleic acid sequence which is identical to SEQ ID NO: 2.

In one or more exemplary embodiments, the nucleic acid construct comprising a recombinant nucleic acid sequence or a functional homologue having a nucleic acid sequence which is at least 70% identical to any one of SEQ ID NO: 3, 4, 5, 6, 7, 8. SEQ ID NO: 3, 4, 5, 6, 7 and 8 encodes a polypeptide capable of transporting an HMO out of the cell. These constructs are functional or a functional homologue of any one of the GenBank accession IDs: WP_017489914.1, WP_092672081.1, EEQ08298.1, WP_087817556.1, WP_048785139.1 or WP_060448169.1 having an amino acid sequence which is at least 80% identical to any one of any one of the GenBank accession IDs: WP_017489914.1, WP_092672081.1, EEQ08298.1, WP_087817556.1, WP_048785139.1 or WP_060448169.1.

In one or more exemplary embodiments the invention relates to a nucleic acid construct further comprising a recombinant nucleic acid sequence which is at least 70% identical, such as at least 80%, such as at least 85%, such as at least 90%, such as at least 95% identical to SEQ ID NO: 9 or 10 encoding a polypeptide capable of hydrolyzing sucrose into fructose and glucose of any one of the GenBank accession IDs: WP_103853210.1 and BAD18121.1, or a functional homologue of any one of the GenBank accession IDs: WP_103853210.1 and BAD18121.1, having an amino acid sequence which is at least 80% identical to any one of the GenBank accession IDs: WP_103853210.1 and BAD18121.1.

The nucleic acid construct can be a recombinant nucleic acid sequence. By the term "recombinant nucleic acid sequence", "recombinant gene/nucleic acid/DNA encoding" or "coding nucleic acid sequence" used interchangeably is meant an artificial nucleic acid sequence (i.e. produced in vitro using standard laboratory methods for making nucleic acid sequences) that comprises a set of consecutive, non-overlapping triplets (codons) which is transcribed into mRNA and translated into a protein when under the control of the appropriate control sequences, i.e. a promoter sequence.

The boundaries of the coding sequence are generally determined by a ribosome binding site located just upstream of the open reading frame at the 5'end of the mRNA, a transcriptional start codon (AUG, GUG or UUG), and a translational stop codon (UAA, UGA or UAG). A coding sequence can include, but is not limited to, genomic DNA, cDNA, synthetic, and recombinant nucleic acid sequences.

The term "nucleic acid" includes RNA, DNA and cDNA molecules. It is understood that, as a result of the degeneracy of the genetic code, a multitude of nucleic acid sequences encoding a given protein may be produced.

In a presently preferred embodiment, the nucleic acid construct comprises a recombinant nucleic acid sequence which is identical to SEQ ID NO: 2, wherein the nucleic acid sequence encodes an α-1,2-fucosyltransferase of SEQ ID NO: 1.

A Recombinant Nucleic Acid Sequence

The recombinant nucleic sequence may be a coding DNA sequence e.g., a gene, or non-coding DNA sequence e.g., a regulatory DNA, such as a promoter sequence.

Accordingly, in one exemplified embodiment the invention relates to a nucleic acid construct comprising a coding nucleic sequence, i.e. recombinant DNA sequence of a gene of interest, e.g. a fucosyltransferase gene, and a non-coding regulatory DNA sequence, e.g. a promoter DNA sequence, e.g. a recombinant promoter sequence derived from the promoter sequence of lac operon or an glp operon, or a promoter sequence derived from another genomic promoter DNA sequence, or a synthetic promoter sequence, wherein the coding and promoter sequences are operably linked.

In one exemplified embodiment, the nucleic acid construct of the invention may be a part of the vector DNA, in another embodiment the construct it is an expression cassette/cartridge that is integrated in the genome of a host cell.

Accordingly, the term "nucleic acid construct" means an artificially constructed segment of nucleic acid, in particular a DNA segment, which is intended to be 'transplanted' into a target cell, e.g. a bacterial cell, to modify expression of a gene of the genome or express a gene/coding DNA sequence which may be included in the construct.

Integration of the nucleic acid construct of interest comprised in the construct (expression cassette) into the bacterial genome can be achieved by conventional methods, e.g. by using linear cartridges that contain flanking sequences homologous to a specific site on the chromosome, as described for the attTn7-site (Waddell C. S. and Craig N. L., Genes Dev. (1988) February; 2(2):137-49); methods for genomic integration of nucleic acid sequences in which recombination is mediated by the Red recombinase function of the phage λ or the RecE/RecT recombinase function of the Rac prophage (Murphy, J Bacteriol. (1998); 180(8): 2063-7; Zhang et al., Nature Genetics (1998) 20:123-128 Muyrers et al., EMBO Rep. (2000) 1(3):239-243); methods based on Red/ET recombination (Wenzel et al., Chem Biol. (2005), 12(3):349-56; Vetcher et al., Appl Environ Microbiol. (2005); 71(4):1829-35); or positive clones, i.e. clones that carry the expression cassette, can be selected e.g. by means of a marker gene, or loss or gain of gene function.

As described above, the disclosure enables the use of regulatory elements for the expression of a nucleic acid or gene of interest, and thus a nucleic acid construct may further comprise one or more recombinant nucleic acid sequence(s) comprising a regulatory element, such as a promoter sequence described in the section "promoters" above.

As shown in the Examples and described above, particularly good results are achieved by using a nucleic acid construct, wherein said promoter sequence is PglpF.

In another exemplified embodiment of the invention, the promoter sequence is lac operon promoter sequence, Plac.

Functional Enzymes

To be able to synthesize one or more HMOs, the recombinant cell of the present invention may further comprise the necessary functional enzyme with activity enabling a viable industrial process for HMO production.

Sugar Efflux Transporter

Over the past decade several new and efficient sugar efflux transporter proteins have been identified, each having specificity for different recombinantly produced HMOs and development of recombinant cells expressing said protein are advantageous for large-scale industrial HMO manufacturing. Sugar transport relates to the transport of a sugar, such as, but not limited to, an oligosaccharide.

The genetically engineered cell(s) described herein, may also comprise a recombinant nucleic acid encoding a sugar efflux transporter. A sugar efflux transporter may for example enhance the level of a HMO in a method as described herein. In one or more exemplary embodiments, the genetically engineered cell further comprises a gene product that acts as a sugar efflux transporter.

Influx and/or efflux transport of one/or more HMOs, from the cytoplasm or periplasm of a genetically engineered cell as described herein to the production media and/or from the production media to the cytoplasm or periplasm is disclosed.

A polypeptide, expressed in the genetically engineered cell as disclosed herein, capable of transporting one or more HMOs from the cytoplasm or periplasm to the production medium and/or from the production media to the cytoplasm or periplasm of a genetically engineered cell, is a polypeptide capable of sugar transport.

Thus, in the present context, sugar transport can mean efflux and/or influx transport of sugar(s), such as, but not limited to, an HMO.

Thus, in one or more exemplary embodiments, the genetically engineered cell according to the method described herein further comprises a gene product that acts as a sugar efflux transporter. The gene product that acts as a sugar efflux transporter may be encoded by a recombinant nucleic acid sequence that is expressed in the genetically engineered cell. The recombinant nucleic acid sequence encoding a sugar efflux transporter, may be integrated into the genome of the genetically engineered cell. It may be plasmid borne, or it may be part of an episomal expression element.

MFS Transporters

Exemplary sugar efflux transporters are a subspecies of the Major Facilitator Superfamily proteins. The MFS transporters facilitate the transport of molecules, such as but not limited to sugars like oligosaccharides, across the cellular membranes.

By the term "Major Facilitator Superfamily (MFS)" is meant a large and exceptionally diverse family of the secondary active transporter class, which is responsible for transporting a range of different substrates, including sugars, drugs, hydrophobic molecules, peptides, organic ions, etc.

The term "MFS transporter" in the present context means, a protein that facilitates transport of an oligosaccharide, preferably, an HMO, through the cell membrane, preferably transport of an HMO/oligosaccharide synthesized by the genetically engineered cell as described herein from the cell cytosol to the cell medium. Additionally, or alternatively, the MFS transporter may also facilitate efflux of molecules that are not considered HMO or oligosaccharides, such as lactose, glucose, cell metabolites and/or toxins.

In one or more exemplary embodiments, the MFS transporter protein is selected from the group consisting of Bad, Nec, YberC, Fred, Vag and Marc.

In one or more presently preferred exemplary embodiments, the sugar efflux transporter is Nec or YberC.

Bad

The MFS transporter protein identified herein as "Bad protein" or "Bad transporter" or "Bad", interchangeably, has the amino acid sequence of SEQ ID NO: 3; The amino acid sequence identified herein as SEQ ID NO: 3 is an amino acid sequence that has 100% identity with the amino acid sequence having the GenBank accession ID WP_017489914.1.

In one or more exemplary embodiments, the sugar efflux transporter and/or MFS transport protein is Bad.

Nec

The MFS transporter protein having the amino acid sequence of SEQ ID NO: 4 is identified herein as "Nec protein" or "Nec transporter" or "Nec", interchangeably; a nucleic acid sequence encoding nec protein is identified herein as "Nec coding nucleic acid/DNA" or "nec gene" or "nec"; The amino acid sequence identified herein as SEQ ID NO: 4 is the amino acid sequence that is 100% identical to the amino acid sequence having the GenBank accession ID WP_092672081.1.

In one or more exemplary embodiments, the sugar efflux transporter and/or MFS transport protein is Nec. In a further embodiment the sugar efflux transporter has the amino acid sequence of SEQ ID NO: 4 or is a functional homologue having an amino acid sequence which is at least 70% identical, such as at least 80% identical, such as at least 85% identical, such as at least 90% identical, such as at least 95% identical or such as at least 99% identical to any one of SEQ ID NO: 4.

In one or more exemplary embodiments, the sugar efflux transporter and/or MFS transport protein is Nec.

YberC

The MFS transporter protein having the amino acid sequence of SEQ ID NO: 5 is identified herein as "YberC protein" or "YberC transporter" or "YberC", interchangeably; a nucleic acid sequence encoding yberC protein is identified herein as "YberC coding nucleic acid/DNA" or "yberC gene" or "yberC"; The amino acid sequence identified herein as SEQ ID NO: 5 is the amino acid sequence that is 100% identical to the amino acid sequence having the GenBank accession ID EEQ08298.1.

In one or more exemplary embodiments, the sugar efflux transporter and/or MFS transport protein is YberC. In a further embodiment the sugar efflux transporter has the amino acid sequence of SEQ ID NO: 5 or is a functional homologue having an amino acid sequence which is at least 70% identical, such as at least 80% identical, such as at least 85% identical, such as at least 90% identical, such as at least 95% identical or such as at least 99% identical to any one of SEQ ID NO: 5.

In one or more exemplary embodiments, the sugar efflux transporter and/or MFS transport protein is YberC.

Fred

The MFS transporter protein having the amino acid sequence of SEQ ID NO: 6 is identified herein as "Fred protein" or "Fred transporter" or "Fred", interchangeably; a nucleic acid sequence encoding fred protein is identified herein as "Fred coding nucleic acid/DNA" or "fred gene" or "fred"; The amino acid sequence identified herein as SEQ ID NO: 6 is the amino acid sequence that is 100% identical to the amino acid sequence having the GenBank accession ID WP_087817556.1.

In one or more exemplary embodiments, the sugar efflux transporter and/or MFS transport protein is Fred.

Vag

The MFS transporter protein having the amino acid sequence of SEQ ID NO: 7 is identified herein as "Vag protein" or "Vag transporter" or "Vag", interchangeably; a nucleic acid sequence encoding vag protein is identified herein as “Vag coding nucleic acid/DNA” or “vag gene” or “vag”; The amino acid sequence identified herein as SEQ ID NO: 7 is the amino acid sequence that is 100% identical to the amino acid sequence having the GenBank accession ID WP_048785139.1.

In one or more exemplary embodiments, the sugar efflux transporter and/or MFS transport protein is Vag.

Marc

The MFS transporter protein having the amino acid sequence of SEQ ID NO: 8 is identified herein as “Marc protein” or “Marc transporter” or “Marc”, interchangeably; a nucleic acid sequence encoding marc protein is identified herein as “Marc coding nucleic acid/DNA” or “marc gene” or “Marc”; The amino acid sequence identified herein as SEQ ID NO: 8 is the amino acid sequence that is 100% identical to the amino acid sequence having the GenBank accession ID WP_060448169.1.

In one or more exemplary embodiments, the sugar efflux transporter and/or MFS transport protein is Marc.

In one or more exemplary embodiments, the sugar efflux transporter and/or MFS transport protein selected from the group consisting of Bad, Nec, YberC, Fred, Vag, and Marc, may be a functional homologue.

In one or more exemplary embodiments, a sugar efflux transporter functional homologue having an amino acid sequence which is at least 70% identical, such as at least 80% identical, such as at least 85% identical, such as at least 90% identical, such as at least 95% identical or such as at least 99% identical to any one of SEQ ID NOs: 3, 4, 5, 6, 7 or 8.

Glycosyltransferases

To be able to synthesize one or more HMOs, the recombinant cell of the described herein comprises at least one recombinant nucleic acid which encodes a functional enzyme with glycosyltransferase activity. The galactosyltransferase gene may be integrated into the genome (by chromosomal integration) of the genetically engineered cell, or alternatively, it may be comprised in a construct that may be integrated into the genome of the genetically engineered cell or inserted into a plasmid DNA and expressed as plasmid borne. If two or more glycosyltransferases are needed for the production of an HMO, e.g. LNT or LNnT, two or more recombinant nucleic acids encoding different enzymes with glycosyltransferase activity may be integrated in the genome, included in a construct and/or expressed from a plasmid, e.g. a β-1,3-N-acetylglucosaminyltransferase (a first recombinant nucleic acid encoding a first glycosyltransferase) in combination with a β-1,3-galactosyltransferase (a second recombinant nucleic acid encoding a second glycosyltransferase) for the production of LNT, where the first and second recombinant nucleic acid can independently from each other be integrated chromosomally or on a plasmid.

A protein/enzyme with glycosyltransferase activity (glycosyltransferase) may be selected in different embodiments from enzymes having the activity of α-1,2-fucosyltransferase, α-1,3-fucosyltransferase, α-1,3/4-fucosyltransferase, α-1,4-fucosyltransferase α-2,3-sialyltransferase, α-2,6-sialyltransferase, β-1,3-N-acetylglucosaminyltransferase, β-1,6-N-acetylglucosaminyltransferase, β-1,3-galactosyltransferase and β-1,4-galactosyltransferase.

For example, the production of 2'-FL requires that the engineered cell expresses an active α-1,2-fucosyltransferase enzyme; for the production of LNT the engineered cell need to express at least two glycosyltransferases, a β-1,3-N-acetylglucosaminyltransferase and a β-1,3-galactosyltransferase; the production of LNFP-I requires that the engineered cell expresses at least one active α-1,2-fucosyltransferase enzyme in combination with at least two glycosyltransferases, a β-1,3-N-acetylglucosaminyltransferase and a β-1,3-galactosyltransferase. Some non-limiting embodiments of proteins having glycosyltransferase activity, which can be encoded by the recombinant genes comprised by the production cell, can be selected from non-limiting examples of Table 1.

Beta-1,3-N-Acetyl-Glucosaminyltransferase

A β-1,3-N-acetyl-glucosaminyltransferase (also known as UDP-GlcNAc:Gala/β-R β-3-N-acetylglucosaminyltransferase) is any protein which comprises the ability of transferring the N-acetyl-glucosamine of UDP-N-acetyl-glucosamine to lactose or another acceptor molecule, in a beta-1,3-linkage. Preferably, a β-1,3-N-acetyl-glucosaminyltransferase used herein does not originate in the species of the genetically engineered cell i.e. the gene encoding the β-1,3-galactosyltransferase is of heterologous origin. Non-limiting examples of β-1,3-N-acetyl-glucosaminyltransferase are given in table 1. β-1,3-N-acetyl-glucosaminyltransferase variants may also be useful, preferably such variants are at least 80%, such as at least 85%, such as at least 90, such as at least 95% identical to one of the β-1,3-N-acetyl-glucosaminyltransferase in table 1.

Production of neutral N-acetylglucosamine-containing HMOs in modified bacteria is also known in the art (see e.g. Gebus C et al. (2012) Carbohydrate Research 363 83-90).

For the production of N-acetylglucosamine-containing HMOs, such as Lacto-N-triose II (LNT-II), Lacto-N-tetraose (LNT), Lacto-N-neotetraose (LNnT), Lacto-N-fucopentaose I (LNFP-I), Lacto-N-fucopentaose II (LNFP-II), Lacto-N-fucopentaose III (LNFP-III), Lacto-N-fucopentaose V (LNFP-V), Lacto-N-fucohexaose V (LNFP-VI), Lacto-N-difucohexaose I (LDFH-I), Lacto-N-difucohexaose II (LDFH-II), and Lacto-N-neodifucohexaose II (LNDFH-III), the genetically engineered cell comprises a dysfunctional lacZ gene, and it is modified to comprise an exogenous UDP-GlcNAc:Gala/β-R β-3-N-acetylglucosaminyltransferase gene, or a functional homologue or fragment thereof.

This exogenous gene may be obtained from any one of a number of sources, e.g., the IgtA gene described from *N. meningitidis* (Genbank protein Accession AAF42258.1 or WP_033911473.1) or *N. gonorrhoeae* (Genbank protein Accession ACF31229.1).

In an exemplary embodiment of the present invention the genetically engineered cell comprises at least one copy of a β-1,3-N-acetyl-glucosaminyltransferase of SEQ ID NO: 40 or a functional homologue thereof having an amino acid sequence which is at least 80% identical, such as at least 85%, such as at least 90%, such as at least 95% identical to SEQ ID NO: 40. It may be advantageous to have at least to copies of β-1,3-N-acetyl-glucosaminyltransferase in the genetically engineered cell of the present invention.

Optionally, an additional exogenous glycosyltransferase gene may be co-expressed in the bacterium comprising an exogenous UDP-GlcNAc:Gala/β-R β-3-N-acetylglucosaminyltransferase. For example, a β-1,3-galactosyltransferase gene is co-expressed with the UDP-GlcNAc:Gala/β-R β-3-N-acetylglucosaminyltransferase gene to generate an LNT producing cell.

β-1,3-Galactosyltransferase

A β-1,3-Galactosyltransferase is any protein that comprises the ability of transferring the galactose of UDP-Galactose to a N-acetyl-glucosaminyl moiety to an acceptor molecule in a beta-1,3-linkage. Preferably, a β-1,3-galactosyltransferase used herein does not originate in the species of the genetically engineered cell i.e., the gene encoding the β-1,3-galactosyltransferase is of heterologous or exogenous origin. Non-limiting examples of β-1,3-galactosyltransferases are given in table 2. β-1,3-galactosyltransferases variants may also be useful, preferably such variants are at least 80%, such as at least 85%, such as at least 90, such as at least 95% identical to one of the β-1,3-galactosyltransferases in table 1.

This exogenous β-1,3-galactosyltransferase gene can be obtained from any one of a number of sources, e.g., the one described from *H. pylori*, the galTK gene (homologous to Genbank protein Accession BD182026.1), or from the wbgO gene (Genbank protein Accession WP_000582563.1), or from *H. pylori*, the jhp0563 gene (Genbank protein Accession AEZ55696.1), or from *Streptococcus agalactiae* type lb O12 the cpslBJ gene (Genbank protein Accession AB050723. Functional variants and fragments of any of the enzymes described above are also encompassed by the disclosed invention In an exemplary embodiment of the present invention the genetically engineered cell comprises at least one copy of a β-1,3-galactosyltransferase of SEQ ID NO: 41 or a functional homologue thereof having an amino acid sequence which is at least 80% identical, such as at least 85%, such as at least 90%, such as at least 95% identical to SEQ ID NO: 41. It may be advantageous to have at least to copies of β-1,3-N-acetyl-glucosaminyltransferase in the genetically engineered cell of the present invention.

In an exemplified embodiment, both the first and second recombinant nucleic acids are stably integrated into the chromosome of the production cell; in another presently exemplified embodiment at least one of the first and second glycosyltransferase is plasmid-borne.

Lactose Permease

In the present invention, lactose is used as the substrate for the synthesis of LNT-II, which is then sued as substrate for the synthesis of LNT (or LNnT) which is then used as substrate for the synthesis of LNFP-I. Thus, a genetically engineered cell of the present invention should be capable of importing lactose into the cell. While lactose is naturally imported into some microorganisms, other microorganisms lack the ability to do so. To enable lactose import, such microorganisms would need to be genetically engineered to take up lactose. Thus, in embodiments of the present invention, the genetically engineered cell of the present invention, is able to import lactose into the cell.

One way to enable lactose import into a cell of the present invention is by expression of a lactose permease. In microorganisms comprising a lactose import pathway, the overexpression of an endogenous lactose import pathway, such as but not limited to an endogenous lactose permease protein, and/or incorporation of a heterologous lactose import pathway, such as but not limited to a heterologous lactose permease, may be used to enhance the lactose import of said microorganism. Thus, in embodiments of the present invention, the genetically engineered cell of the present invention overexpresses an endogenous lactose permease protein and/or expresses a heterologous lactose permease.

β-Galactosidase

A genetically engineered cell capable of producing one or more HMOs, e.g. *E. coli*, may comprise an endogenous β-galactosidase gene or an exogenous β-galactosidase gene, e.g. *E. coli* comprises an endogenous lacZ gene (e.g., GenBank Accession ID V00296 (GI:41901)).

An HMO-producing host cell is genetically manipulated to either not comprise any β-galactosidase gene or to comprise the gene that is inactivated. The gene may be inactivated by a complete or partial deletion of the corresponding nucleic acid sequence from the bacterial genome, or the gene sequence is mutated in the way that it is not transcribed, or, if transcribed, the transcript is not translated or if translated to a protein (i.e. β-galactosidase), the protein does not have the corresponding enzymatic activity. In this way the HMO-producing bacterium accumulates an increased intracellular lactose pool which is beneficial for the production of HMOs.

Glycosyl-Donor-Nucleotide-Activated Sugar Pathways

When carrying out the method of this invention, preferably a glycosyltransferase mediated glycosylation reaction takes place in which an activated sugar nucleotide serves as glycosyl-donor. An activated sugar nucleotide generally has a phosphorylated glycosyl residue attached to a nucleoside. A specific glycosyl transferase enzyme accepts only a specific sugar nucleotide. Thus, preferably the following activated sugar nucleotides are involved in the glycosyl transfer: glucose-UDP-GlcNAc, UDP-galactose, UDP-glucose, UDP-N-acetylglucosamine, UDP-N-acetylgalactosamine (GlcNAc) and CMP-N-acetylneuraminic acid. The genetically modified cell according to the present invention can comprise one or more pathways to produce a nucleotide-activated sugar selected from the group consisting of glucose-UDP-GlcNAc, GDP-fucose, UDP-galactose, UDP-glucose, UDP-N-acetylglucosamine, UDP-N-acetylgalactosamine and CMP-N-acetylneuraminic acid (CMP-Neu5Ac). In table 5 below are non-limiting examples of glycosyl-doners and the HMO products they can be used to produce, the list may not be exhaustive.

TABLE 5 glycosyl-donor HMO product list

| Glycosyl-donor | HMO product |
|---|---|
| UDP-GlcNAc | LNT, LNnT, LNFP-I, LNFP-II, LNFP-III, LNFP-V, LNFP-VI, LNDFH-I, LNDFH-II, LNDFH-III, LNH, LNnH, pLNH, pLNnH, F-pLNH-I, F-pLNH-II, F-pLNH-I, F-pLNnH-II, FLSTa, FLSTb, FLSTc, FLSTd, LSTa, LSTb, LSTc, LSTd, DSLNT, SLNH, SLNH-II |
| UDP-Gal | LNT, LNnT, LNFP-I, LNFP-II, LNFP-III, LNFP-V, LNFP-VI, LNDFH-I, LNDFH-II, LNDFH-III, LNH, LNnH, pLNH, pLNnH, F-pLNH-I, F-pLNH-II, F-pLNH-I, F-pLNnH-II, FLSTa, FLSTb, FLSTc, FLSTd, LSTa, LSTb, LSTc, LSTd, DSLNT, SLNH-I, SLNH-II |
| GDP-fucose | 2'FL, 3FL, DFL, LNFP-I, LNFP-II, LNFP-III, LNFP-V, LNFP-VI, LNDFH-I, LNDFH-II, LNDFH-III, F-LNH, F-LNnH, F-pLNH-I, F-pLNH-II, F-pLNH-I, F-pLNnH-II, FSL, FLSTa, FLSTb, FLSTc, FLSTd |
| CMP-Neu5Ac | 3'SL, 6'SL, FSL, FLSTa, FLSTb, FLSTc, FLSTd, LSTa, LSTb, LSTc, LSTd, DSLNT, SLNH-I, SLNH-II |

In one embodiment of the method of the invention, the genetically modified cell is capable of producing one or more activated sugar nucleotides mentioned above by a de novo pathway. In this regard, an activated sugar nucleotide is made by the cell under the action of enzymes involved in the de novo biosynthetic pathway of that respective sugar nucleotide in a stepwise reaction sequence starting from a simple carbon source like glycerol, sucrose, fructose or glucose (for a review for monosaccharide metabolism see e.g. H. H. Freeze and A. D. Elbein: Chapter 4: Glycosylation precursors, in: Essentials of Glycobiology, 2nd edition (Eds. A. Varki et al.), Cold Spring Harbour Laboratory Press (2009)).

The enzymes involved in the de novo biosynthetic pathway of an activated sugar nucleotide can be naturally present in the cell or introduced into the cell by means of gene technology or recombinant DNA techniques, all of them are parts of the general knowledge of the skilled person.

In another embodiment, the genetically modified cell can utilize salvaged monosaccharides for sugar nucleotide. In the salvage pathway, monosaccharides derived from degraded oligosaccharides are phosphorylated by kinases, and converted to nucleotide sugars by pyrophosphorylases. The enzymes involved in the procedure can be heterologous ones, or native ones of the host cell.

Colanic Acid Gene Cluster

For the production of fucosylated HMO's the colanic acid gene cluster is important to ensure presence of sufficient GDP-fucose. In *Escherichia coli* GDP-fucose is an intermediate in the production of the extracellular polysaccharide colanic acid, a major oligosaccharide of the bacterial cell wall. In the context of the present invention the colanic acid gene cluster encodes the enzymes involved in the de novo synthesis of GDP-fucose (gmd, wcaG, wcaH, wcaI, manB, manC), whereas one or several of the genes downstream of GDP-L-fucose, such as wcaJ, can be deleted to prevent conversion of GDP-fucose to colanic acid.

The colanic acid gene cluster responsible for the formation of GDP-fucose comprises or consists of the genes: gmd which encodes the protein GDP-mannose-4,6-dehydratase (UniProt accession nr P0AC88); wcaG (fcl) which encodes the protein GDP-L-fucose synthase (EC 1.1.1.271, UniProt accession nr P32055); wcaH which encodes the protein GDP-mannose mannosyl hydrolase hydrolase (EC 3.6.1.-, UniProt accession nr P32056); wcaI which encodes the colanic acid biosynthesis glycosyltransferase (UniProt accession nr P32057); manB which encodes the protein phosphomannomutase (EC 5.4.2.8, UniProt accession nr P24175) and manC which encodes the protein mannose-1-phosphate guanylyltransferase guanylyltransferase (EC: 2.7.7.13, UniProt accession nr P24174).

In one or more exemplary embodiment(s), the colanic acid gene cluster responsible for the formation of GDP-fucose may be expressed from its native genomic locus. The expression may be actively modulated to increase GDP-fucose formation. The expression can be modulated by swapping the native promoter with a promoter of interest, and/or increasing the copy number of the colanic acid genes coding said protein(s) by expressing the gene cluster from another genomic locus than the native, or episomally expressing the colanic acid gene cluster or specific genes thereof.

In relation to the present disclosure, the term "native genomic locus", in relation to the colanic acid gene cluster, relates to the original and natural position of the gene cluster in the genome of the genetically engineered cell.

Use of a Genetically Engineered Cell

The disclosure also relates to any commercial use of the genetically engineered cell or the nucleic acid construct, comprising a recombinant nucleic acid sequence which is at least 70% identical to SEQ ID NO: 2, wherein the nucleic acid sequence encodes an $\alpha$-1,2-fucosyltransferase of SEQ ID NO: 1, or a functional homologue thereof having an amino acid sequence which is at least 80% identical, such as at least 85% identical, or such as at least 90% identical, or such as at least 95% identical to SEQ ID NO: 1.

Thus, in one or more exemplary embodiments, the genetically engineered cell or the nucleic acid construct according to the invention is used in the manufacturing of one or more HMOs, in particular one or more fucosylated HMOs. The one or more HMOs can be selected from the group consisting of 2'-FL, LNT-II, LNT, LNnT, LNFP-I, DFL pLNnH, and LNDFH-I, and the one or more fucosylated HMOs may be selected from the group consisting of 2'-FL, LNFP-I, DFL pLNnH, and LNDFH-I. The one or more fucosylated HMOs may further comprise other HMOs such as LNT-II, LNT, LNnT or even sialylated HMOs.

In a presently preferred embodiment, the one or more HMOs is/are selected from the group consisting of 2'-FL, LNT-II, LNT, LNFP-I and LNDFH-I.

In one or more exemplary embodiments, the genetically engineered cell and/or the nucleic acid construct is used in the manufacturing of more than one HMO(s), wherein the one or more HMOs is/are selected from the group consisting of 2'-FL, LNT, LNFP-I and LNDFH-I.

In another exemplified embodiment, the genetically engineered cell and/or the nucleic acid construct according to the invention, is used in the manufacturing of more than one fucosylated HMO(s), wherein the HMOs are 2'-FL, LNFP-I and LNDFH-I.

In another exemplified embodiment, the genetically engineered cell and/or the nucleic acid construct according to the present disclosure, is used in the manufacturing of more than one HMO(s), wherein the HMOs are 2'-FL, LNT and LNFP-I.

In another exemplified embodiment, the genetically engineered cell and/or the nucleic acid construct according to the invention, is used in the manufacturing of more than one HMO(s), wherein the HMOs are 2'-FL and LNFP-I.

In another exemplified embodiment, the genetically engineered cell and/or the nucleic acid construct according to the invention, is used in the manufacturing of more than one HMO(s), wherein the HMOs are LNT and LNFP-I.

In one or more exemplary embodiments, the genetically engineered cell and/or the nucleic acid construct is used in the manufacturing of LNFP-I.

In one or more exemplary embodiments, the one or more HMOs described above, contains LNFP-I as the predominant HMO. Specifically, LNFP-I constitute more than 70 molar % of the total HMO, such as more than 75%, such as more than 80%, such as more than 85%, such as more than 90%, such as more than 95 molar % of the total HMO.

Manufacturing of HMOs

To produce one or more HMOs, the genetically engineered cell as described herein are cultivated according to the procedures known in the art in the presence of a suitable carbon source, e.g. glucose, glycerol, sucrose, etc., and the produced HMO is harvested from the cultivation media and the microbial biomass formed during the cultivation process. Thereafter, the HMOs are purified according to the procedures known in the art, e.g. such as described in WO2015188834, WO2017182965 or WO2017152918, and the purified HMOs are used as food ingredients, nutraceuticals, pharmaceuticals, or for any other purpose, e.g. for research.

Manufacturing of HMOs is typically accomplished by performing cultivation in larger volumes. The term "manufacturing" and "manufacturing scale" in the meaning of the invention defines a fermentation with a minimum volume of 5 L culture broth. Manufacturing scale or large-scale production are typically a fermentation with a minimum volume of 1,000 L, such as 10,000 L, such as 50,000 L, such as 100,000 L, such as 200,000 L, such as 300,000 L culture broth. Usually, a "manufacturing scale" process is defined by being capable of processing large volumes of a preparation containing the product of interest and yielding amounts of the HMO of interest that meet, e.g. in the case of a therapeutic compound or composition, the demands for clinical trials as well as for market supply. In addition to the large volume, a manufacturing scale method, as opposed to simple lab scale methods like shake flask cultivation, is characterized by the use of the technical system of a bioreactor (fermenter) which is equipped with devices for agitation, aeration, nutrient feeding, monitoring and control of process parameters (pH, temperature, dissolved oxygen tension, back pressure, etc.). To a large extent, the behaviour of an expression system in a lab scale method, such as shake flasks, benchtop bioreactors or the deep well format described in the examples of the disclosure, does allow to predict the behaviour of that system in the complex environment of a manufacturing bioreactor.

With regard to the suitable cell medium used in the fermentation process, there are no limitations. The culture medium may be semi-defined, i.e. containing complex media compounds (e.g. yeast extract, soy peptone, casamino acids, etc.), or it may be chemically defined, without any complex compounds. Where sucrose is used as the carbon and energy source, a minimal medium might be preferable.

Manufactured Product

The term "manufactured product" according to the use of the genetically engineered cell or the nucleic acid construct refer to the one or more HMOs intended as the one or more product HMO. The various products are described above.

Advantageously, the methods disclosed herein provides both a decreased ratio of by-product to product and an increased overall yield of the product (and/or HMOs in total). This, less by-product formation in relation to product formation facilitates an elevated product production and increases efficiency of both the production and product recovery process, providing superior manufacturing procedure of HMOs.

The manufactured product may be a powder, a composition, a suspension, or a gel comprising one or more HMOs.

TABLE 1

Non-limiting examples of glycosyltransferases in the framework of the present disclosure

| Gene | Protein Sequence ID (GenBank) | Description | HMO example |
|---|---|---|---|
| IgtA_Nm | WP_033911473.1 | β-1,3-N-acetylglucosaminyl-transferase | LNT-II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| IgtA_Nm_MC58 | AAF42258.1 | β-1,3-N-acetylglucosaminyl-transferase | LNT-II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| IgtA_Hd | AAN05638.1 | β-1,3-N-acetylglucosaminyl-transferase | LNT-II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| IgtA_Ng_PID2 | AAK70338.1 | β-1,3-N-acetylglucosaminyl-transferase | LNT-II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| IgtA_Ng_NCCP11945 | ACF31229.1 | β-1,3-N-acetylglucosaminyl-transferase | LNT-II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| IgtA_Past | AAK02595.1 | β-1,3-N-acetylglucosaminyl-transferase | LNT-II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| IgtA_Nc | EEZ72046.1 | β-1,3-N-acetylglucosaminyl-transferase | LNT-II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| IgtA_Nm_87255 | ELK60643.1 | β-1,3-N-acetylglucosaminyl-transferase | LNT-II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| HD0466 | WP_010944479.1 | β-1,3-N-acetylglucosaminyl-transferase | LNT II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| PmnagT | WP_014390683.1 | β-1,3-N-acetylglucosaminyl-transferase | LNT II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| galT_Hp | WP_001262061.1 | β-1,4-galactosyl-transferase | LNnT, LNFP-III, LNFP-VI, LNDFH-III, pLNH I, F-pLNH I, pLNnH |
| wbgO | WP_000582563.1 | β-1,3-galactosyl-transferase | LNT, LNFP-I, LNFP-II, LNFP-V, LNDFH-I, LNDFH-II, pLNH, F-pLNH I |
| cpslBJ | AB050723.1 | β-1,3-galactosyl-transferase | LNT, LNFP-I, LNFP-II, LNFP-V, LNDFH-I, LNDFH-II, pLNH, F-pLNH I |
| jhp0563 | AEZ55696.1 | β-1,3-galactosyl-transferase | LNT, LNFP-I, LNFP-II, LNFP-V, LNDFH-I, LNDFH-II, pLNH, F-pLNH I |
| galTK | homologous to BD182026.1 WP_111735921.1 | β-1,3-galactosyl-transferase | LNT, LNFP-I, LNFP-II, LNFP-V, LNDFH-I, LNDFH-II, pLNH, F-pLNH I |

TABLE 1-continued

Non-limiting examples of glycosyltransferases in the framework of the present disclosure

| Gene | Protein Sequence ID (GenBank) | Description | HMO example |
|---|---|---|---|
| Cvb3galT | WP_080969100.1 | β-1,3-galactosyl-transferase | LNT, LNFP-I, LNFP-II, LNFP-V, LNDFH-I, LNDFH-II, pLNH, F-pLNH I |
| futC | WP_080473865.1 | α-1,2-fucosyl-transferase | 2'-FL, DFL, LNFP-I, LNDFH-I, DFL |
| FucT2_HpUA802 | AAC99764.1 | α-1,2-fucosyl-transferase | 2'-FL, DFL, LNFP-I, LNDFH-I, DFL |
| FucT2_EcO126t | ABE98421.1 | α-1,2-fucosyl-transferase | 2'-FL, DFL, LNFP-I, LNDFH-I, DFL |
| FucT2_Hm12198 | CBG40460.1 | α-1,2-fucosyl-transferase | 2'-FL, DFL, LNFP-I, LNDFH-I, DFL |
| FucT2_Pm9515 | ABM71599.1 | α-1,2-fucosyl-transferase | 2'-FL, DFL, LNFP-I, LNDFH-I, DFL |
| FucT2_HpF57 | BAJ59215.1 | α-1,2-fucosyl-transferase | 2'-FL, DFL, LNFP-I, LNDFH-I, DFL |
| FucT54 | ADE13114.1 | α-1,2-fucosyl-transferase | 2'-FL, DFL, LNFP-I, LNDFH-I, DFL |
| Smob | WP_126455392.1 | α-1,2-fucosyl-transferase | 2'-FL, DFL, LNFP-I, LNDFH-I, DFL |
| Mtun | WP_031437198.1 | α-1,2-fucosyl-transferase | 2'-FL, LNFP-I, LNDFH-I, DFL |

TABLE 2

Genotypes of the strains MP1, MP3 and MP2

| Strain ID | Genotype | Heterologous Protein Sequence ID (GenBank) |
|---|---|---|
| MP1 | MDO, x1 GlcNAcT*, x1 GalTK**, x1 CA***, x1 futC[4] | WP_033911473.1<br>BD182026.1 (modified)[5]<br>WP_080473865.1 |
| MP2 | MDO, x1 GlcNAcT*, x1 GalTK**, x1 CA***, x1 fucT54[6] | WP_033911473.1<br>BD182026.1 (modified)[5]<br>ADE13114.1 |
| MP3 | MDO, x1 GlcNAcT*, x1 GalTK**, x1 CA***, x1 smob[7] | WP_033911473.1<br>BD182026.1 (modified)[5]<br>WP_126455392.1 |

*GlcNAcT: IgtA β-1,3-N-acetyloglucosamine transferase (SEQ ID NO: 40) under control of PglpF promoter

**GalTK: β-1,3-galactosyltransferase (SEQ ID NO: 41) under control of PglpF promoter

***CA: extra colanic acid gene cluster (gmd-wcaG-wcaH-wcal-manC-manB) at a locus that is different than the native locus (see for example PCT/EP2021/086932 SEQ ID NO: 30)

[4]futC: α-1,2-fucosyltransferase with NCBI accession No: WP_080473865.1 under control of PglpF promoter

[5]BD182026.1 (modified): compared to BD182026.1, the applied β-1,3-galactosyltransferase sequence has two deletions of 12 and 30 amino acids and shares 90% identity in the homologous regions

[6]fucT54: α-1,2-fucosyltransferase with NCBI accession No: ADE13114.1 under control of PglpF promoter

[7]smob: gene coding for α-1,2-fucosyltransferase of SEQ ID NO: 1 under control of PglpF promoter

TABLE 3

Genotypes of the strains MP4, MP5, MP6 and MP7

| Strain ID | Genotype | Heterologous Protein Sequence ID (GenBank) |
|---|---|---|
| MP4 | MDO, x2 GlcNAcT, x1 GalTK, x1 CA***, x1 smob[4] | WP_033911473.1<br>BD182026.1 (modified)[5]<br>WP_126455392.1 |
| MP5 | MDO, x2 GlcNAcT, x1 GalTK, x1 CA***, x1 smob[4], x1 PglpF-nec[6] | WP_033911473.1<br>BD182026.1 (modified)[5]<br>WP_126455392.1<br>WP_092672081.1 |
| MP6 | MDO, x2 GlcNAcT, x1 GalTK, x1 CA***, x1 smob[4], x1 Plac-yberC[7] | WP_033911473.1<br>BD182026.1 (modified)[5]<br>WP_126455392.1<br>EEQ08298.1 |

TABLE 3-continued

Genotypes of the strains MP4, MP5, MP6 and MP7

| Strain ID | Genotype | Heterologous Protein Sequence ID (GenBank) |
|---|---|---|
| MP7 | MDO, x2 GlcNAcT, x1 GalTK, x1 CA***, x1 smob[4], x1 Plac-nec[6] | WP_033911473.1<br>BD182026.1 (modified)[5]<br>WP_126455392.1<br>WP_092672081.1 |

*GlcNAcT: Igta β-1,3-N-acetyloglucosamine transferase (SEQ ID NO: 40)

**GalTK: β-1,3-galactosyltransferase (SEQ ID NO: 41)

***CA: colanic acid gene cluster (gmd-wcaG-wcaH-wcal-manC-manB) at a locus that is different than the native locus (see for example PCT/EP2021/086932 SEQ ID NO: 30)

[4]smob: gene coding for α-1,2-fucosyltransferase of SEQ ID NO: 1

[5]BD182026.1 (modified): compared to BD182026.1, the applied β-1,3-galactosyltransferase sequence has two deletions of 12 and 30 amino acids and shares 90% identity in the homologous regions

[7]nec: MFS transporter with GenBank accession ID WP_092672081.1 under control of PglpF promoter

[6]YberC: MFS transporter with GenBank accession ID EEQ08298.1

TABLE 6

Genotypes of the strains MP5, MP8 and MP9

| Strain ID | Genotype (all genese are genetically integrated) | Heterologous Protein Sequence ID (GenBank) |
|---|---|---|
| MP5 | MDO, x2 GlcNAcT[1], x1 GalTK[2], x1 CA[3], x1 smob[4], x1 PglpF-nec[6] | WP_033911473.1<br>BD182026.1 (modified)[5]<br>WP_126455392.1<br>WP_092672081.1 |
| MP8 | MDO, x2 GlcNAcT[1], x1 GalTK[2], x1 CA[3], x1 smob[4], x1 PglpF-nec[6], x1 PglpF-sacC_Agal[7] | WP_033911473.1<br>BD182026.1 (modified)[5]<br>WP_126455392.1<br>WP_092672081.1<br>WP_103853210.1 |

TABLE 6-continued

Genotypes of the strains MP5, MP8 and MP9

| Strain ID | Genotype (all genese are genetically integrated) | Heterologous Protein Sequence ID (GenBank) |
|---|---|---|
| MP9 | MDO, x2 GlcNAcT[1], x1 GalTK[2], x1 CA[3], x1 smob[4], x1 PglpF-nec[6], x2 PglpF-sacC_Agal[7] | WP_033911473.1<br>BD182026.1 (modified)[5]<br>WP_126455392.1<br>WP_092672081.1<br>WP_103853210.1 |

[1]GlcNAcT: gene coding for the β-1,3-N-acetyloglucosamine transferase LgtA

[2]GalTK: gene coding for the β-1,3-galactosyltransferase GalTK

[3]CA: extra colanic acid gene cluster (gmd-wcaG-wcaH-wcal-manC-manB) at a locus that is different than the native locus (see for example PCT/EP2021/086932 SEQ ID NO: 30)

[4]smob: gene coding for α-1,2-fucosyltransferase of SEQ ID NO: 1

[5]BD182026.1 (modified): compared to BD182026.1, the applied β-1,3-galactosyltransferase sequence has two deletions of 12 and 30 amino acids and shares 90% identity in the homologous regions

[6]nec: MFS transporter with GenBank accession ID GenBank accession ID WP_092672081.1 under control of PglpF promoter

[7]sacC_Agal: sucrose invertase with GenBank accession ID GenBank accession WP_103853210.1 (SEQ ID NO: 13)

General

It should be understood that any feature and/or aspect discussed above in connections with the described methods apply by analogy to the cells, nucleic acid constructs and uses thereof described herein.

The terms culturing and fermentation are used interchangeably.

The terms Lacto-N-triose, LNT-II, LNT II, LNT2 and LNT 2, are used interchangeably.

The terms genetically modified and genetically engineered are used interchangeably.

Each specific variation of the features disclosed herein can be applied to all other embodiments of the disclosure unless specifically stated otherwise.

Generally, all terms used herein are to be interpreted according to their ordinary meaning in the technical field, and applicable to all aspects and embodiments of the disclosure, unless explicitly defined or stated otherwise.

All references to "a/an/the [cell, sequence, gene, transporter, step, etc]" are to be interpreted openly as referring to at least one instance of said cell, sequence, gene, transporter, step, etc., unless explicitly stated otherwise.

The following figures and examples are provided below to illustrate the present disclosure. They are intended to be illustrative and are not to be construed as limiting in any way.

EXAMPLES

Figure 1:
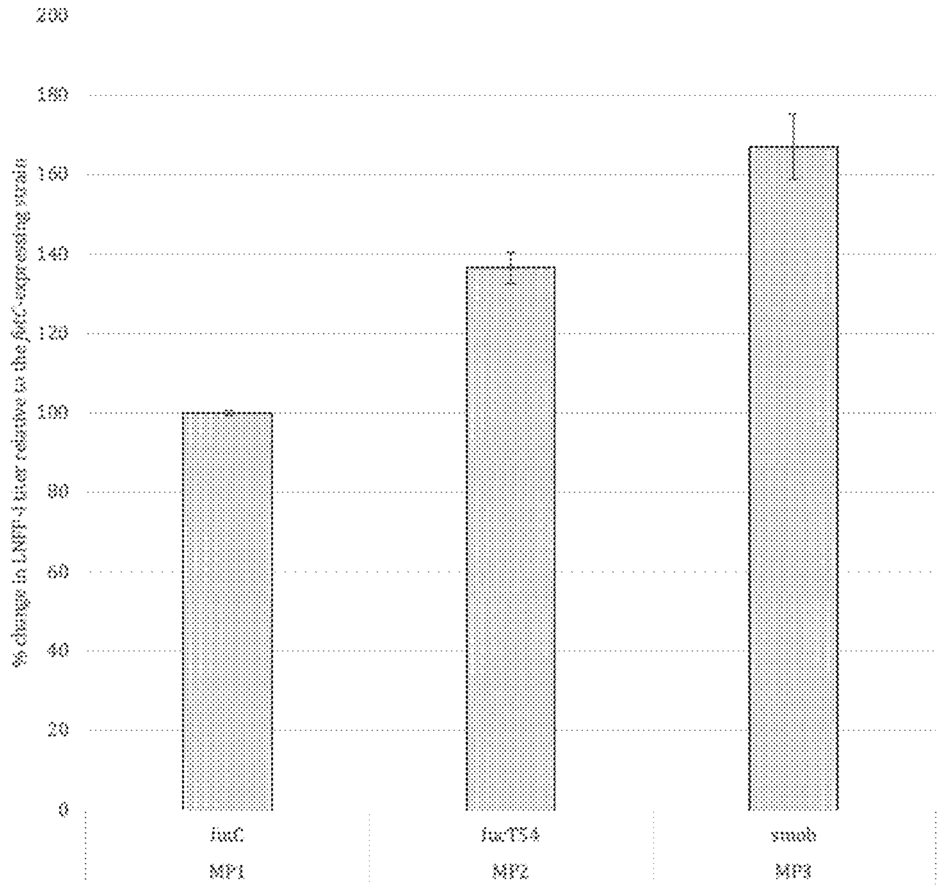
FIG. 1 The choice of the α-1,2-fucosyltransferase that is introduced in an *E. coli* DH1 K12 strain producing LNT has a large impact on the HMO content of the final HMO blend. % change in the final LNFP-I titer of fucT54- and smob-expressing cells relative to cells expressing futC.

Example 1—The LNFP-I Content in Neutral HMO Blends can be Modulated by the Choice of the Expressed α-1,2-Fucosyltransferase Description of the Genotype of Strains MP1, MP2 and MP3 Tested in Deep Well Assays The strains (genetically engineered cells) constructed in the present application were based on *Escherichia coli* K-12 DH1 with the genotype: $F^-$, $\lambda^-$, gyrA96, recA1, relA1, endA1, thi-1, hsdR17, supE44. Additional modifications were made to the *E. coli* K-12 DH1 strain to generate the platform strain "MDO" with the following modifications: lacZ: deletion of 1.5 kbp, lacA: deletion of 0.5 kbp, nanKETA: deletion of 3.3 kbp, melA: deletion of 0.9 kbp, wcaJ: deletion of 0.5 kbp, mdoH: deletion of 0.5 kbp, and insertion of Plac promoter upstream of the gmd gene.

Methods of inserting or deleting gene(s) of interest into the genome of *E. coli* are well known to the person skilled in the art. Insertion of genetic cassettes into the *E. coli* chromosome can be done using gene gorging (see e.g., Herring and Blattner 2004 J. Bacteriol. 186:2673-81 and Warming et al 2005 Nucleic Acids Res. 33(4):e36) with specific selection marker genes and screening methods.

Based on the platform strain ("MDO"), the modifications summarised in Table 2, were made to obtain the fully chromosomal strains MP1, MP3 and MP2. The strains can produce the pentasaccharide HMO, LNFP-I. The glycosyltransferase enzymes LgtA (a β-1,3-N-acetyloglucosamine transferase) from *N. meningitidis* and GalTK (a β-1,3-galactosyltransferase) from *H. pylori* are present in all three strains.

In addition, each of these strains bears a single genomic copy of a gene encoding an α-1,2-fucosyltransferase as indicated in table 2, whose expression is driven by the synthetic inducible promoter PglpF.

Specifically, the strain MP1 expresses a single PglpF-driven copy of the futC gene (*Helicobacter pylori* 26695, Wang et al, Mol. Microbiol., 1999, 31, 1265-1274, GenBank ID: WP_080473865.1), the strain MP3 expresses a single PglpF-driven copy of the fucT54 gene (Sideroxydans lithotrophicus ES-11, WO2019008133A1, GenBank ID: WP_013031010.1) and the strain MP3 expresses a single PglpF-driven copy of the smob gene (*Sulfuriflexus mobilis*, SEQ ID NO: 1 of the present disclosure).

The present Example describes for the first time an α-1,2-fucosyltransferase that is found in nature, Smob, and shows an unpreceded high specificity for LNT and simultaneously a very low specificity for lactose. Contrary to previously tested α-1,2-fucosyltransferases, cells that concomitantly express two glycosyltransferases (SEQ ID NO: 40 and 41) required for LNT synthesis and the Smob enzyme produce almost exclusively LNFP-I. In this manner, the present disclosure demonstrates how the simple strain engineering approach of introducing a single heterologous gene, smob, into the genome of an *E. coli* DH1 K12 strain that already produces LNT can be advantageously employed to either increase the LNFP-I content of neutral HMO blends or establish an in vivo production process that results in an almost "pure" LNFP-I HMO product.

See: Table 2. Genotypes of the strains MP1, MP3 and MP2

Description of the Applied Deep Well Assay Protocol for Strain Characterization

The strains disclosed in the present example were screened in 96 deep well plates using a 4-day protocol. During the first 24 hours, precultures were grown to high densities and subsequently transferred to a medium that allowed induction of gene expression and product formation. More specifically, during day 1, fresh precultures were prepared using a basal minimal medium supplemented with magnesium sulphate, thiamine and glucose. The precultures were incubated for 24 hours at 34° C. and 1000 rpm shaking and then further transferred to a new basal minimal medium (BMM, pH 7.5) in order to start the main culture. The new BMM was supplemented with magnesium sulphate, thiamine, a bolus of 20% glucose solution (50 ul per 100 mL) and a bolus of 10% lactose solution (5 ml per 100 ml). Moreover, 50% sucrose solution was provided as carbon source, accompanied by the addition of sucrose hydrolase (invertase), so that glucose was released at a rate suitable for C-limited growth. The main cultures were incubated for 72 hours at 28° C. and 1000 rpm shaking.

For the analysis of total broth, the 96-well plates were boiled at 100° C., subsequently centrifuged, and finally the supernatants were analysed by HPLC. For supernatant samples, the initial centrifugation of microtiter plates was followed by the removal of 0.1 mL supernatant for direct analysis by HPLC. For pellet samples, the cells were initially washed, then dissolved in deionized water and centrifuged. Following centrifugation, the pellets were analysed for HMO content in the cell interior after resuspension, boiling, centrifugation and analysis of the final supernatant. Results of the Deep Well Assays Since the FutC enzyme is known to have a higher specificity for lactose than for LNT, the formation of 2'-FL is favoured in futC-expressing cells (Wang et al, Mol. Microbiol., 1999, 31, 1265-1274). To promote LNFP-I synthesis in vivo, it is therefore desirable to identify α-1,2-fucosyltransferases other than FutC that show higher specificity for LNT than for lactose. This has been attempted before in patent WO2019008133A1, where several α-1,2-fucosyltransferases were associated with a high specificity for LNT, including the FucT54 enzyme.

In our experiments, strains that express the FutC, FucT54 or Smob enzymes were constructed and characterized in deep well assays, and samples were collected from the total broth of the cultures. All samples were analysed for HMO content by HPLC following the 72-hour protocol described above. The concentration of the detected HMOs in each sample was used to calculate the relative differences in the HMO content of the strains tested, i.e., the % HMO content of fucT54- and smob-expressing cells relative to the HMO content of futC-expressing cells. LNFP-I to 2'-FL ratios were also calculated based on the HMO concentrations determined by HPLC analysis. Finally, the molar % fraction of each HMO in the final blend acquired by each strain was calculated to report the overall HMO profile of each strain.

Figure 2:
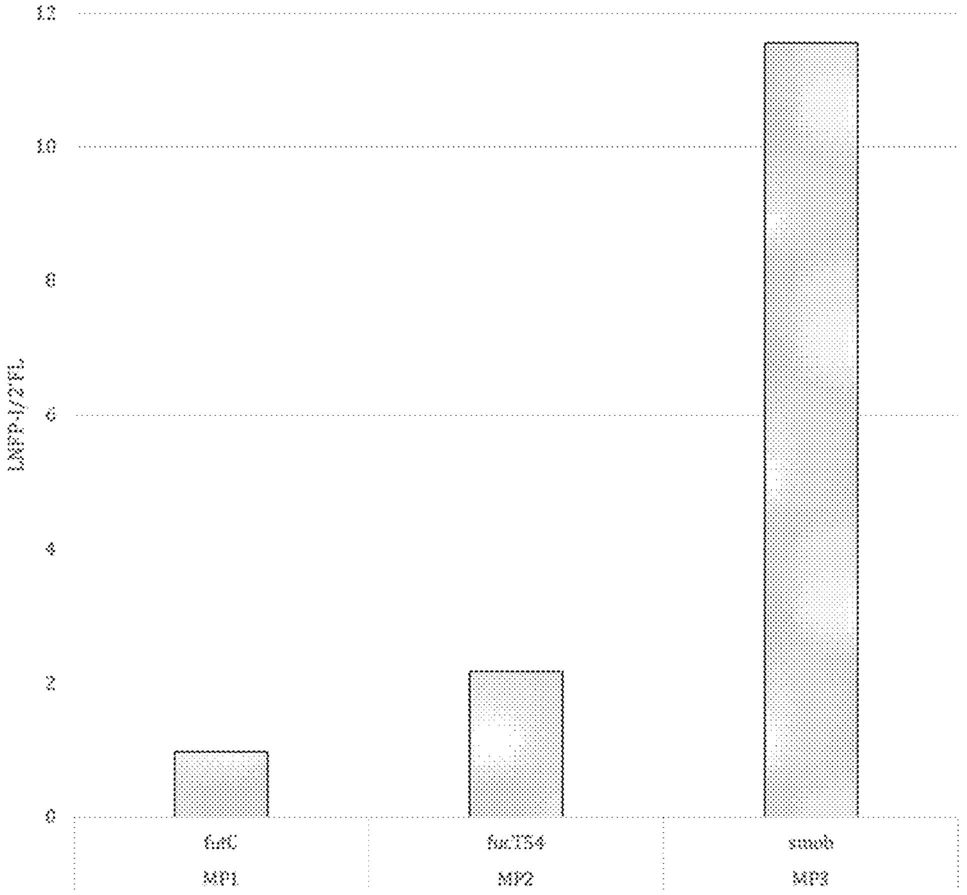
FIG. 2 LNFP-I to 2'-FL molar ratios for strains expressing the FutC, FucT54 or Smob enzymes.
Figure 3:
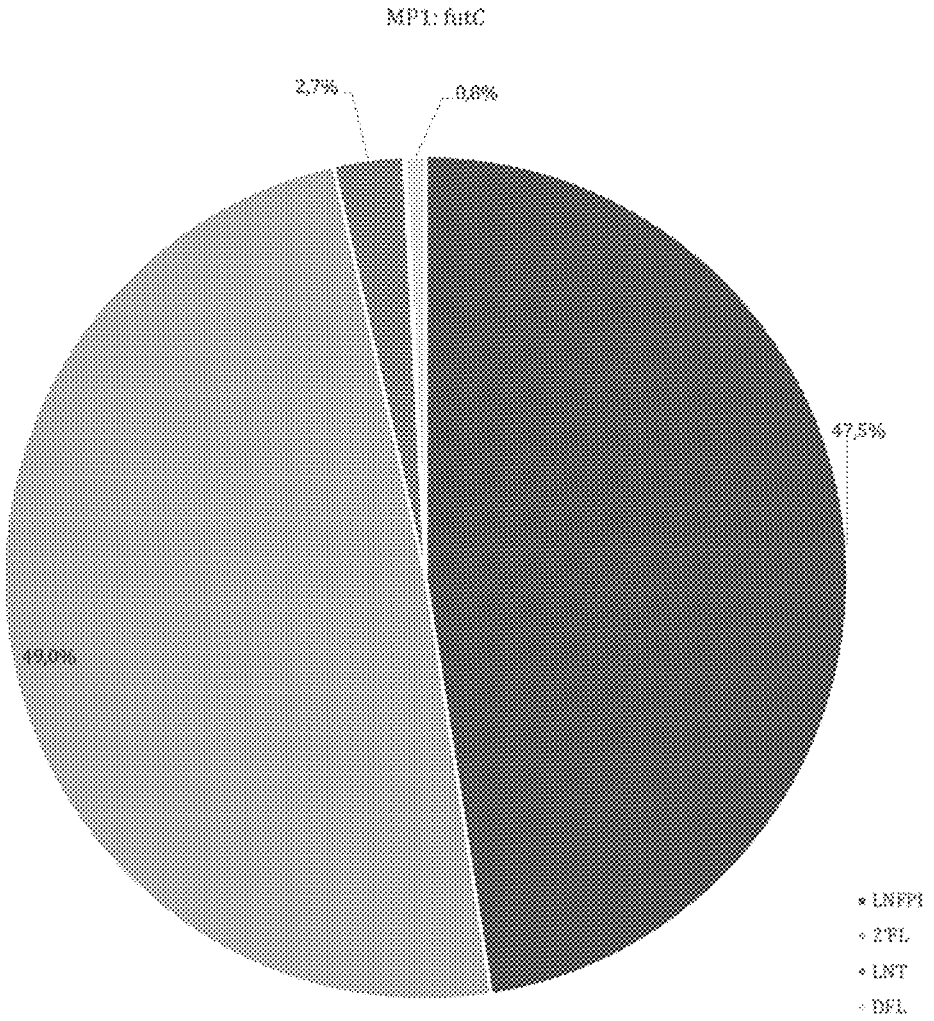
FIG. 3 Molar % fraction of each HMO in the final HMO blend acquired by strain MP1 expressing the futC gene.
Figure 4:
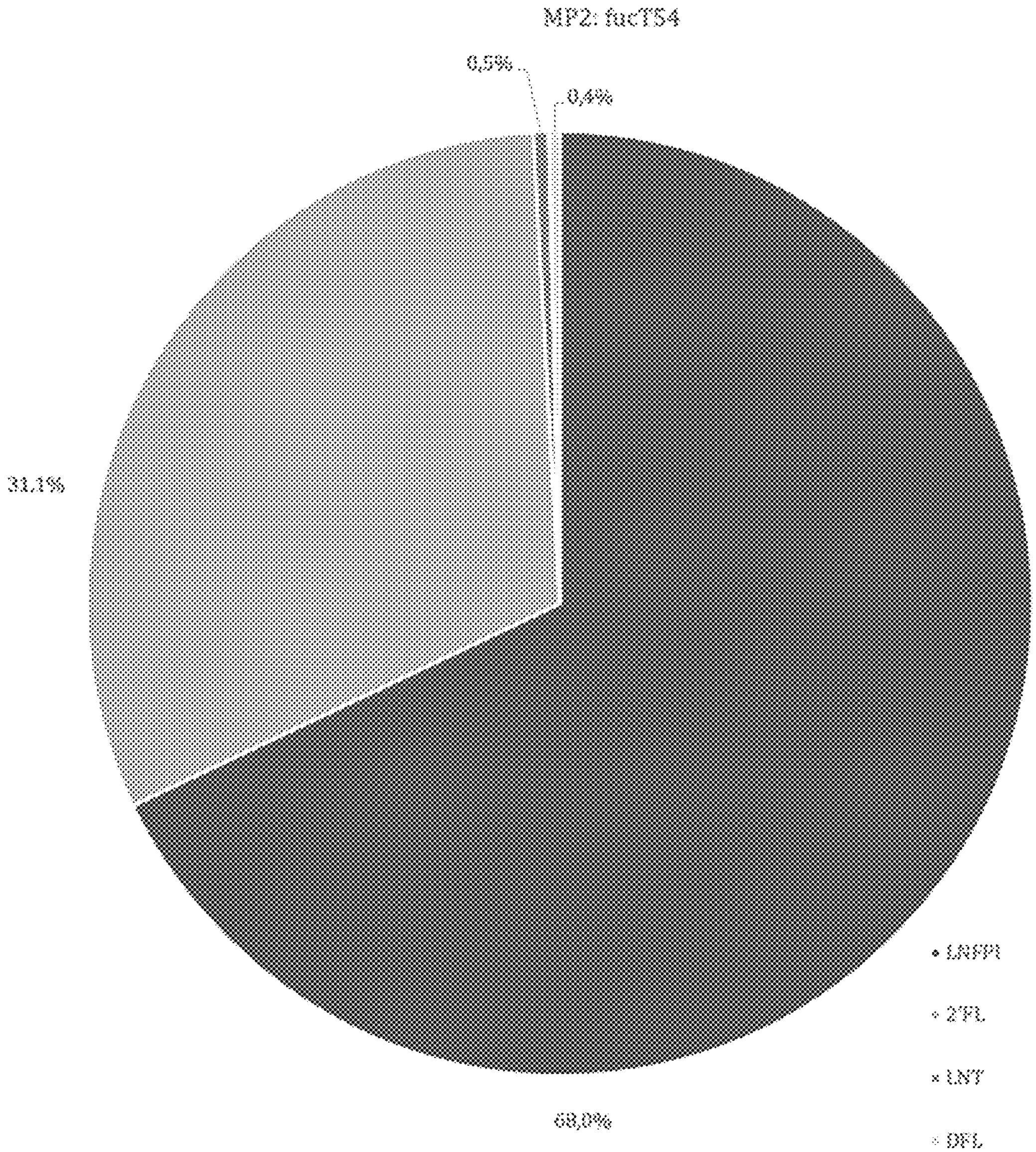
FIG. 4 Molar % fraction of each HMO in the final HMO blend acquired by strain MP2 expressing the fucT54 gene.
Figure 5:
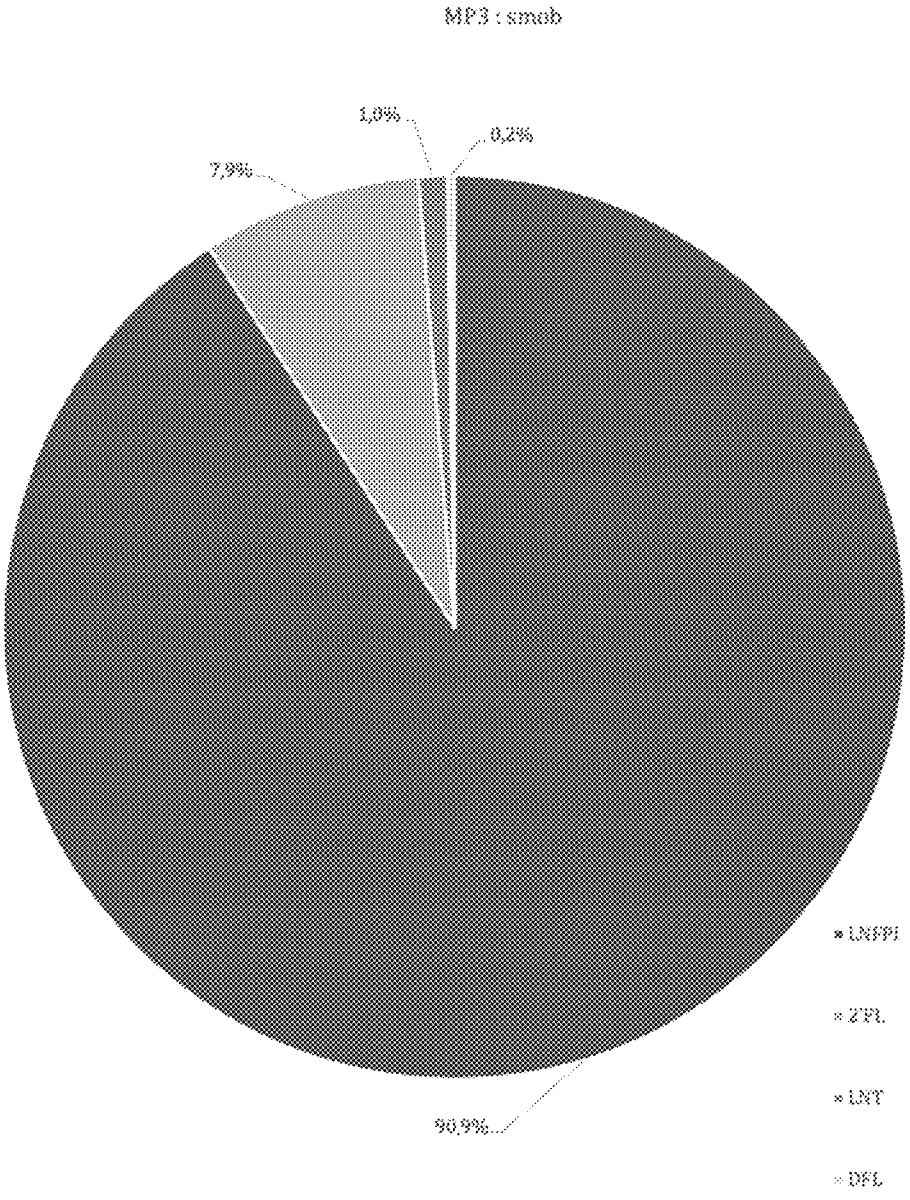
FIG. 5 Molar % fraction of each HMO in the final HMO blend acquired by strain MP3 expressing the smob gene.

As revealed by the analysis of the total samples in deep-well cultures and the calculations mentioned above, the enzyme identified in the present disclosure, namely Smob, appears to be superior to the FutC and FucT54 enzymes in terms of producing LNFP-I due to its inherent high specificity for LNT. As shown in FIG. 1, final LNFP-I titers of the strains expressing the fucT54 gene (strain MP2) and the smob gene (strain MP3) are, respectively, 40% and 70% higher than the LNFP-I titer reached with the strain expressing the futC gene (strain MP1). Likewise, the 1:1 LNFP-1/2'-FL ratio in futC-expressing cells is changed to 2:1 in fucT54- and 11:1 in smob-expressing cells (FIG. 2). As shown in FIG. 3-5, the HMO content in the blends acquired by cells expressing the futC, fucT54 or smob genes differs markedly from strain to strain. Specifically, the almost 50%:50% LNFP-I:2'FL content in the HMO blend delivered by the strain MP1 (FutC) is turned to almost 70%:30% in the strain MP2 (FucT54) or even 90%:10% in the strain MP3 (Smob).

These results highlight the unique advantage offered by the Smob enzyme to generate neutral HMO blends enriched in LNFP-I, or cells producing almost exclusively LNFP-I, which is a highly desired strain engineering goal. Also, the fact that the Smob enzyme meets the above expectations to a higher degree than the previously identified FucT54 enzyme (WO2019008133A1) is unexpected and thereby strengthens the impact of the present disclosure on the HMO field.

Example 2—The Concomitant Expression of the Smob Enzyme and Either of the Heterologous MFS Transporters Nec or YberC is the Key for an Efficient LNFP-I Cell Factory Description of the Genotype of Strains MP4, MP5, MP6 and MP7 Tested in Deep Well Assays Based on the platform strain ("MDO") described in example 1, the modifications summarised in Table 3, were made to obtain the fully chromosomal strains MP4, MP5, MP6 and MP7. The strains can produce the pentasaccharide HMO LNFP-I. The glycosyltransferase enzymes LgtA (a β-1,3-N-acetyloglucosamine transferase, SEQ ID NO: 40) from *N. meningitidis*, GalTK (a β-1,3-galactosyltransferase, SEQ ID NO: 41) from *H. pylori* and Smob (α-1,2-fucosyltransferase (SEQ ID NO: 1) from *S. mobilis* are present in all four strains. Moreover, the strain MP6 expresses the heterologous transporter of the Major Facilitator Superfamily (MFS) YberC (SEQ ID NO: 5) from *Yersinia bercovieri*, while the strains MP5 and MP7 express the heterologous MFS transporter Nec (SEQ ID NO: 4) from *Rosenbergiella nectarea*. The only difference between the latter two strains lies in the strength of the promoter that drives the expression of the nec gene, i.e. a PglpF-driven nec copy is present in the strain MP5, while the strain MP7 expresses the nec gene under the control of the Plac promoter.

The present Example describes an optimized strain engineering approach to construct a highly efficient LNFP-I cell factory that produces LNFP-I at high titers, with a significant fraction of the product being found in the supernatant of the culture. Following the approach described here, HMOs other than LNFP-I constitute only a minor fraction of the total HMO blend delivered by the engineered cell. In the framework of the present Example, introducing the heterologous genes, smob and nec or yberC, ito the genome of an *E. coli* DH1 K12 strain that already produces LNT can be advantageously employed with a high copy number for the IgtA gene to deliver an efficient LNFP-I cell factory with the beneficial traits described above.

See: Table 3. Genotypes of the strains MP4, MP5, MP6 and MP7

Description of the Applied Deep Well Assay Protocol for Strain Characterization

The strains disclosed in the present example were screened in 96 deep well plates using a 4-day protocol. During the first 24 hours, precultures were grown to high densities and subsequently transferred to a medium that allowed induction of gene expression and product formation. More specifically, during day 1, fresh precultures were prepared using a basal minimal medium supplemented with magnesium sulphate, thiamine and glucose. The precultures were incubated for 24 hours at 34° C. and 1000 rpm shaking and then further transferred to a new basal minimal medium (BMM, pH 7.5) in order to start the main culture. The new BMM was supplemented with magnesium sulphate, thiamine, a bolus of 20% glucose solution (50 ul per 100 mL) and a bolus of 20% lactose solution (10 ml per 175 ml). Moreover, 50% sucrose solution was provided as carbon source, accompanied by the addition of sucrose hydrolase (invertase), so that glucose was released at a rate suitable for C-limited growth. The main cultures were incubated for 72 hours at 28° C. and 1000 rpm shaking.

For the analysis of total broth, the 96-well plates were boiled at 100° C., subsequently centrifuged, and finally the supernatants were analysed by HPLC. For supernatant samples, the initial centrifugation of microtiter plates was followed by the removal of 0.1 mL supernatant for direct analysis by HPLC. For pellet samples, the cells were initially washed, then dissolved in deionized water and centrifuged. Following centrifugation, the pellets were analysed for HMO content in the cell interior after resuspension, boiling, centrifugation and analysis of the final supernatant.

Results of the Deep Well Assays

The expression of many host genes as well as the heterologous genes encoding enzymes involved in the in vivo synthesis of a HMO of interest needs to be fine-tuned to achieve an optimal fermentation output, where the desired HMO product is formed at high titers while molecules other than the main product (i.e., precursor or heavily decorated sugars) are formed in minimal amounts. Moreover, the export of the newly formed HMO of interest needs to be exported in the cell exterior to alleviate the cell from the HMO-imposed osmotic stress. The identification of sugar exporters and the fine balancing of their expression can be a key for the success of such production systems. This task can though be challenging, since only the HMO of interest, and not the precursor or elongated versions thereof, should be bound and exported by the chosen sugar exporter.

After following some strain engineering rounds to balance the expression of the enzymes involved in LNFP-I synthesis, sugar transporters that were proven to be able to export the LNFP-I product out of the cell, namely Nec and YberC (FIG. 9), were also introduced in the LNFP-I production system. Relevant strains were constructed and characterized in deep well assays as described in the previous sections. Samples were collected from the total broth as well as the supernatant and pellet fractions of the cultures. All samples were analysed for HMO content by HPLC following the 72-hour protocol described above. The concentration of the detected HMOs in each sample was used to calculate the % quantitative differences in the HMO content of the strains tested, i.e., the % HMO content of nec- and yberC-expressing cells relative to the HMO content of cells that do not express a heterologous transporter.

Figure 6:
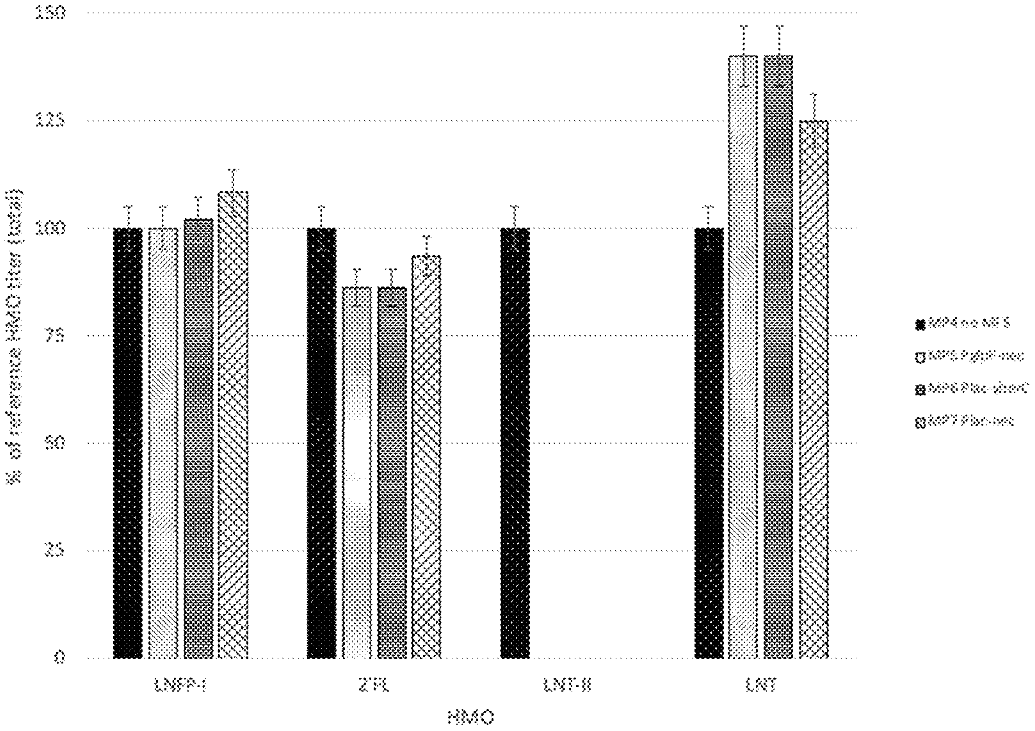
FIG. 6 The final HMO titers for smob-expressing strains that bear a genomic copy of the nec (strains MP5 and MP7) or yberC (strain MP6) genes, shown relative to the final HMO titers of smob-expressing cells that do not express an MFS transporter (strain MP4), as revealed by the analysis of total samples. The reference level (given as 100%) is shown for strain MP4.

As revealed by the analysis of the total samples in deep-well cultures, minor gains in LNFP-I titers can be achieved when a transporter is expressed in a LNFP-I system with balanced expression of glycosyltransferases, i.e. up to 10% higher LNFP-I titers are observed for then strain MP7 (Nec) than the strain MP4 (no transporter) (FIG. 6). Moreover, the introduction of a sugar exporter in LNFP-I production strains induces drastic changes in the abundance of the other HMOs in the final blend. Specifically, LNT II is absent from the total broth of all transporter-expressing cells, with the latter reaching approximately 20% lower 2'-FL and up to 40% higher LNT titers (strains MP6 and MP5) compared to the strain that does not express a sugar transporter (strain MP4) (FIG. 6). It should be noted that the relatively large increase in LNT titers (up to 40%) observed for the transporter-expressing cells can be attributed to the low values of LNT concentrations reported for all four strains.

Figure 7:
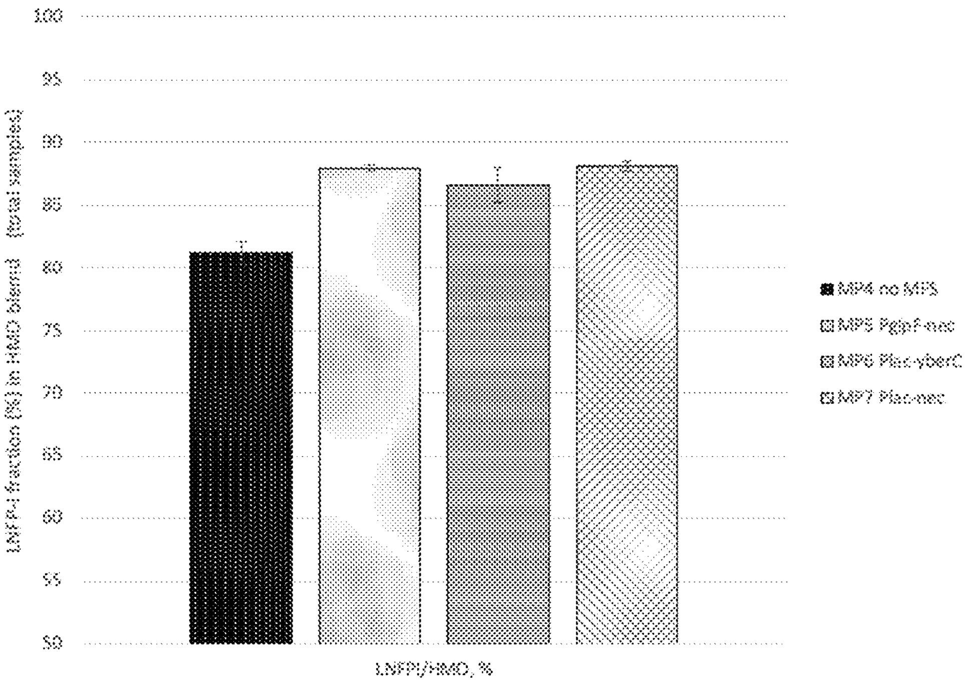
FIG. 7 Fraction of LNFP-I (in molar %) in the final HMO blend for smob-expressing cells that do not express a MFS transporter (strain MP4) and cells that bear a genomic copy of the nec (strains MP5 and MP7) or yberC (strain MP6) genes, as revealed by the analysis of total samples.

The minor gains in the relative final LNFP-I titers and the drastic changes in the relative abundance of other HMOs observed for MFS-expressing cells was expectedly reflected in the absolute LNFP-I fraction (%) that was measured in the final HMO blend. Specifically, as revealed by the analysis of the total samples, the absolute fraction of LNFP-I in the final HMO blend reached approximately 88% for cells expressing the Nec transporter (strains MP5 and MP7), while this fraction corresponded to approximately 81% for cells that do not express a MFS transporter (FIG. 7).

Figure 8:
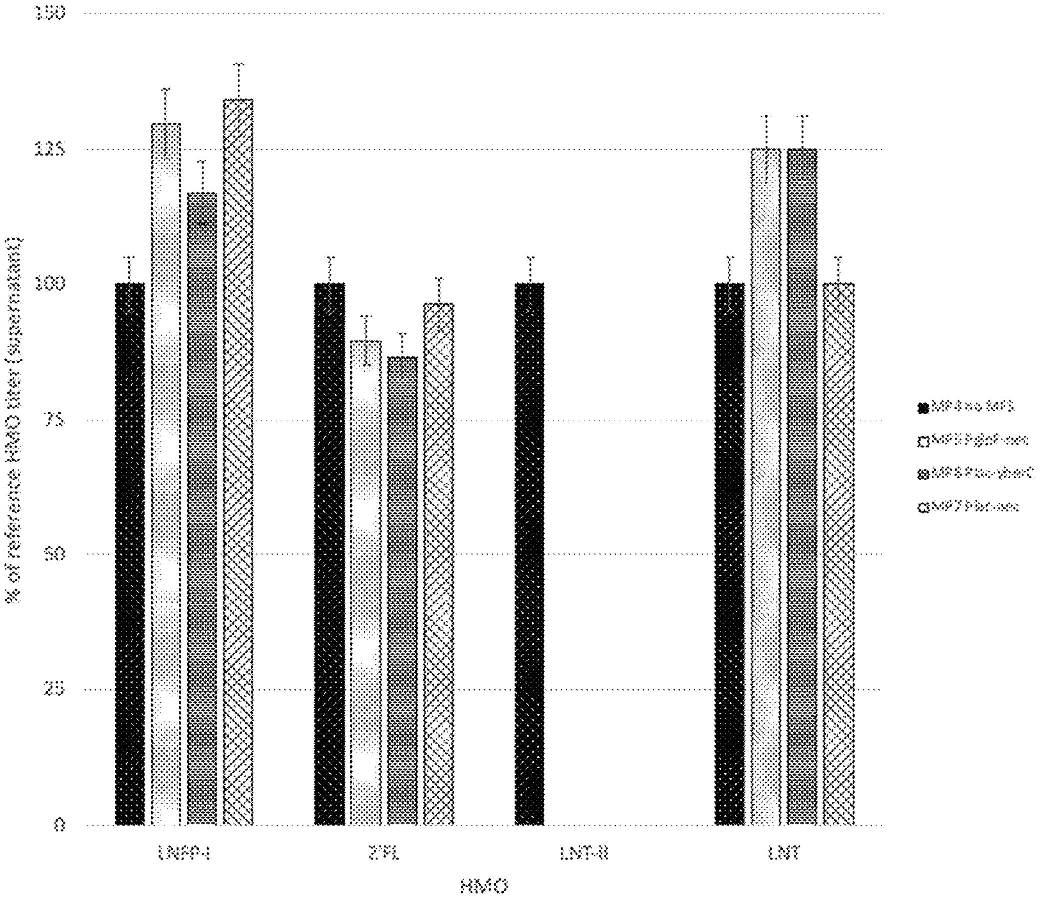
FIG. 8 The final HMO titers for smob-expressing strains that bear a genomic copy of the nec (strains MP5 and MP7) or yberC (strain MP6) genes, shown relative to the final HMO titers of smob-expressing cells that do not express an MFS transporter (strain MP4), as revealed by the analysis of the supernatant fraction of the corresponding cultures. The reference level (given as 100%) is shown for strain MP4.

The analysis of the supernatant and total samples of strains tested in deep-well cultures revealed similar trends regarding the observed relative abundance changes in LNT II, LNT and 2'-FL for transporter-expressing cells (FIGS. 6 and 8). However, the analysis of supernatant samples revealed a striking fact about LNFP-I. In detail, although only a minor relative overall gain in LNFP-I titer can be achieved by the strain MP7, which expresses the Nec transporter under the control of the Plac promoter (FIG. 6), the extracellular LNFP-I fraction of this strain is much higher (up to 30%) than the strain MP4, which does not express a sugar transporter (FIG. 8). The same trend is observed for the strains expressing the YberC transporter (strain MP6) or the Nec transporter from a PglpF-driven genomic copy (strain MP5) (FIG. 8).

Figure 9:
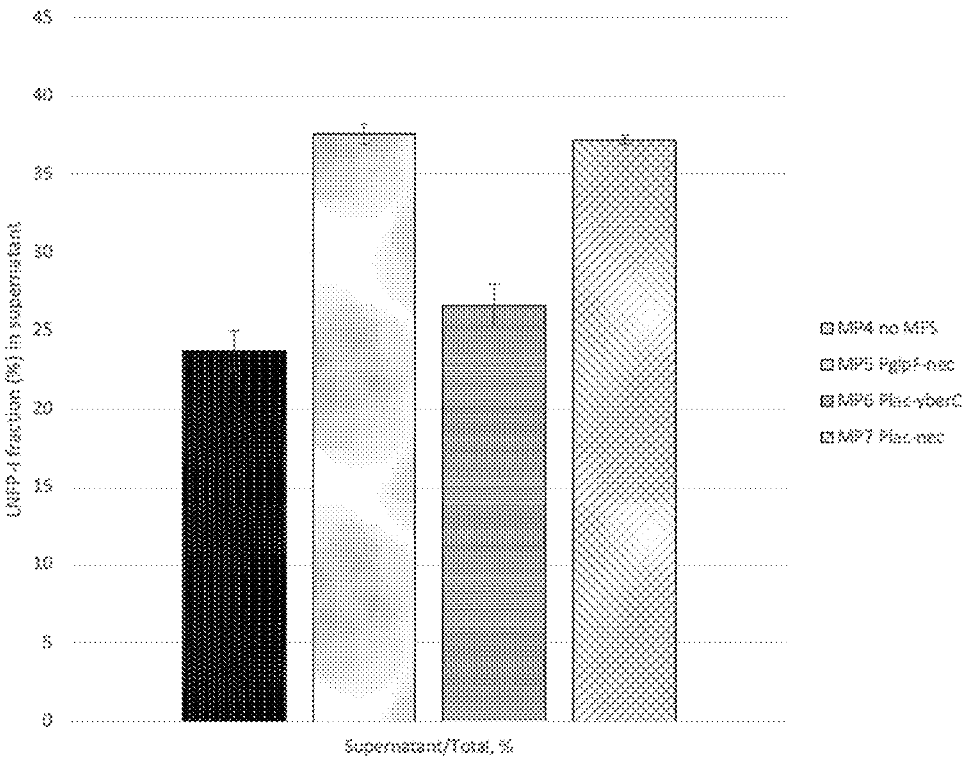
FIG. 9 Fraction of LNFP-I detected in the supernatant (in % of total LNFP-I) in cultures of smob-expressing cells that do not express a MFS transporter (strain MP4) and smob-expressing cells that bear a genomic copy of the nec (strains MP5 and MP7) or yberC (strain MP6) genes.

The marked increase in the supernatant fraction of LNFP-I for MFS-relative to no MFS-expressing cells was expectedly reflected in the absolute LNFP-I fraction (%) that was detected in the supernatant of the corresponding cultures. In detail, only 24% of the total LNFP-I was detected in the supernatant for cells that do not express an MFS transporter (strain MP4), while approximately 38% of the synthesized LNFP-I was detected in the supernatant of cultures for cells expressing the Nec transporter (FIG. 9).

In conclusion, the balanced expression of the β-1,3-N-acetyloglucosamine transferase LgtA, the β-1,3-galactosyltransferase GalTK, the α-1,2-fucosyltransferase Smob and either of the MFS transporters Nec or YberC constitute an effective strain engineering strategy for the generation of a highly productive LNFP-I cell factories. Such microbial systems produce LNFP-I at high titers, with a significant fraction of the product being found in the supernatant of the culture, and HMOs other than LNFP-I representing only a minor fraction of the total HMO blend delivered by the engineered cell.

Example 3—The SacC_Agal Sucrose Utilization Technology can be Successfully Applied to Engineer *E. coli* Cells Producing the Complex Pentasaccharide LNFP-I Description of the Genotype of Strains MP5, MP8 and MP9

Based on the platform strain ("MDO", MP1) described in example 1, the modifications summarised in Table 6 were made to obtain the fully chromosomal strains MP5, MP8 and MP9.

The strains can produce the pentasaccharide HMO LNFP-I, the tetrasaccharide HMO LNT and the trisaccharide HMO 2'-FL. The glycosyltransferase enzymes LgtA (a β-1,3-N-acetyloglucosamine transferase) from *N. meningitidis*, GalTK (a β-1,3-galactosyltransferase) from *H. pylori*, Smob (α-1,2-fucosyltransferase) from *S. mobilis* and the heterologous MFS transporter Nec from *Rosenbergiella nectarea*. are present in all three strains. Contrary to the strain MP5, the strains MP8 and MP11 can utilize sucrose as the carbon and energy source since the gene sacC_Agal from *Avibacterium gallinarum* is integrated on their genome in one or two loci, respectively.

This invention demonstrates how the introduction of an extracellular invertase such as SacC_Agal can be advantageously used to confer an engineered *E. coli* that produces the complex pentasaccharide LNFP-I the ability to utilize sucrose as carbon and/or energy source. The only difference between the strains MP5 and MP8 or MP9, as shown in the table below, is the absence of the SacC_Agal enzyme from the former and its presence in the latter two strains. Although the strain MP8 bears a single PglpF-driven copy of the sacC_Agal gene, the strain MP9 bears two such copies.

In the present Example, it is demonstrated that sacC_Agal-expressing cells not only grow robustly in batch cultures containing sucrose, but they also produce LNFP-I at high titers in fed-batch fermentation processes.

Description of the Protocol Applied During Growth Monitoring Assays

The strains disclosed in the present example were screened in 96 well microtiter plates using a 2,5-day protocol. During the first 24 hours, cells were grown to high densities while in the next 36 hours cells were transferred to a medium containing sucrose as the main carbon and energy source. Specifically, during day 1, fresh inoculums were prepared using a Luria-Bertani broth containing 20% glucose. After 24 hours of incubation of the prepared cultures at 34° C., cells were transferred to a basal minimal medium (200 uL) supplemented with magnesium sulphate and thiamine to which an initial bolus of 20% glucose solution and 15 g/L sucrose solution as carbon source was provided to the cells. After inoculation of the new medium, cells were shaken at 1200 rpm at 28° C. for 72 hours. The cells were grown in a batch mode of cultivation in microtiter plates that were compatible with the Varioskan LUX Multimode Microplate Reader from ThermoFisher Scientific.

Fermentation Protocol

The *E. coli* strains were cultivated in 250 mL fermenters (Ambr250 HT Bioreactor system, Sartorius) starting with 100 mL of mineral culture medium consisting of 30 g/L glucose or sucrose (AL-X16 and AL-X17 respectively) and a mineral medium comprised of $NH_4H_2PO_4$, $KH_2PO_4$, $MgSO_4x7H_2O$, NaOH, citric acid, trace element solution, antifoam and thiamine. The dissolved oxygen level was kept at 20% by a cascade of first agitation and then airflow starting at 700 rpm (up to max 4500 rpm) and 1 VVM (up to max 3 VVM). The pH was kept at 6.8 by titration with 8.5% $NH_4OH$ solution. The cultivations were started with 2% (v/v) inoculums from pre-cultures comprised of 10 g/L glucose (AL-X16) or sucrose (AL-X17), $(NH_4)_2HPO_4$, $KH_2PO_4$, $MgSO_4x7H_2O$, KOH, NaOH, citric acid, trace element solution, antifoam and thiamine. After depletion of the glucose or sucrose contained in the basal minimal medium, a glucose (AL-X16) or sucrose-(AL-X17) containing feed solution was continuously added to the fermenter at a rate that maintained carbon-limiting conditions. The temperature was initially at 33° C. but was dropped to 30° C. after 3 hours of feeding. Lactose was added as a bolus addition of 25% lactose monohydrate solution 36 hours after feed start and then every 19 hours to keep lactose from being a rate limiting factor. The growth, metabolic activity and metabolic state of the cells was followed by on-line measurements of reflectance and $CO_2$ evolution rate. Throughout the fermentations, samples were taken to determine the concentration of HMO products, lactose and other minor by-products using HPLC.

Results of the Growth Monitoring in Assays

Strains were tested in growth monitoring assays using the 60-hour protocol described above, with the cultures being operated at the batch mode in the presence of sucrose. To evaluate the ability of different strains to grow on sucrose as a function of their genetic makeup (i.e., expression or not of the SacC_Agal enzyme that is directly associated with sucrose utilization), the raw data on culture absorbance (in 600 nm), reported by the Varioskan LUX system, was used to inspect the growth curves on sucrose for the strains tested, namely MP5, MP8 and MP9. The data analysis software Skanlt was used to extract all growth curves and execute various calculations.

Figure 10:
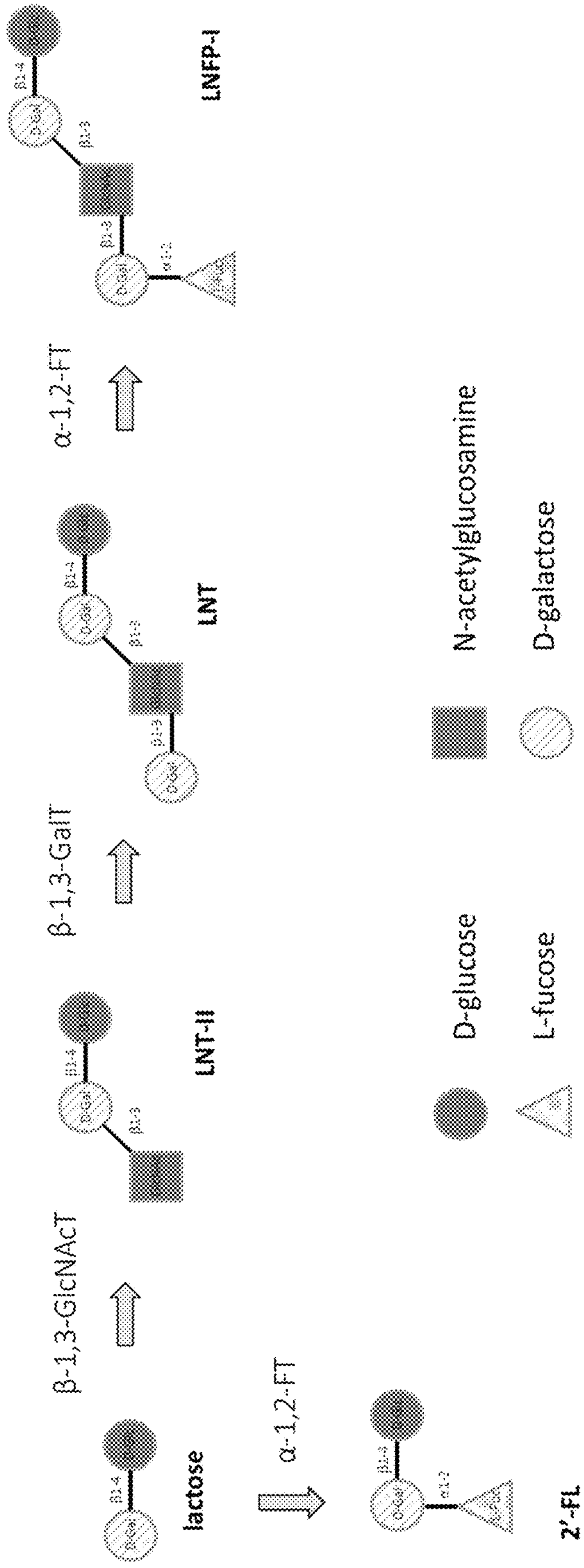
FIG. 10 Pathways for producing LNFP-I and 2'-FL respectively from lactose. 2'FL is produced in a single step from lactose in the presence of the enzyme α-1,2-fucosyltransferase (α-1,2-ft) adding fucose to the lactose. Production of LNFP-I is a 3 step process where a β-1,3-N-acetylglucosaminyltransferase (β-1,3-GlcNacT) adds N-acetylglucosamine to lactose to form LNT-II to which a β-1,3-galactosyltransferase (β-1,3-GalT) adds galactose forming LNT on which an α-1,2-fucosyltransferase (α-1,2-ft) adds a fucose to form LNFP-I. As illustrated in example 1 different α-1,2-fucosyltransferase may have different substrate specificities, i.e. FutC seem to have higher specificity for lactose whereas smob seems to have higher specificity for LNT as substrate.
Figure 11:
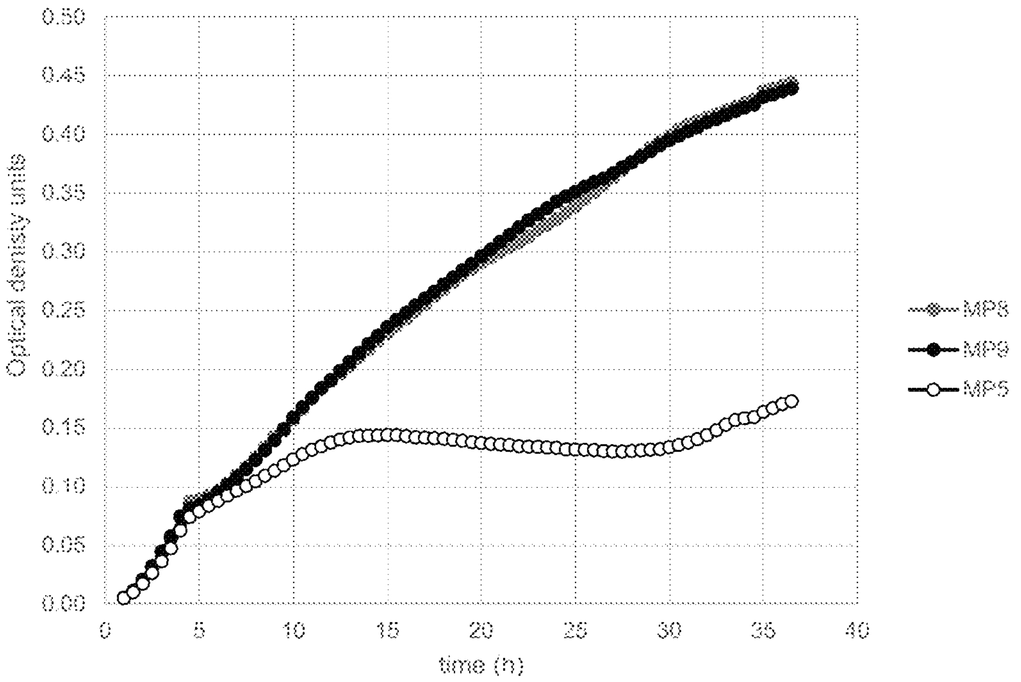
FIG. 11 Batch growth profile on sucrose for *E. coli* cells that do or do not express protein(s) that enable the utilization of sucrose as the main and/or the sole, carbon source and/or energy source. The strain MP5 is not capable of utilizing sucrose, while the strains MP8 and MP9 express the extracellular sucrose hydrolase SacC_Agal from one or two PglpF-driven genomic copies, respectively

As shown in FIG. 11, the strain MP5, which does not bear the sacC_Agal on its genome, cannot grow on the sucrose that is provided in the medium being present in the prepared batch cultures. After a little growth (due to the provided low levels of glucose and the potentially partially degraded sucrose that could be present in the medium), the strain MP5 has a flat growth profile (FIG. 11). On the contrary, the strain MP8 and MP9, which bear a single or two PglpF-driven copies of the sacC_Agal gene, respectively, grow nicely on sucrose over time and reach much higher optical density values than the strain MP5 (FIG. 10). It is also noteworthy that the strains MP8 and MP9 have an almost identical growth profile, which indicates that a single PglpF-driven copy of the sacC_Agal gene should be sufficient to support robust growth on sucrose (FIG. 11).

In this manner, the present disclosure indicates an efficient strain engineering tool for producing flexi-fuel strains (capable of growing on more than one carbon source) with a normal cell physiology, which could indicate a presumably low metabolic burden in sacC_Agal-expressing cells compared to other multi-gene sucrose utilization technologies that are known in the art (e.g., scrBRYA).

In the present example the SacC_Agal sucrose invertase was introduced into the LNFP-I expressing host cell, identified in table 4 as MP5. In detail, the sacC_Agal gene was placed under control of the PglpF promoter and integrated in the chromosome in a single (strain MP8) or two copies (strain MP9). Also, it is hereby demonstrated that sacC_Agal-expressing cells not only grow robustly in batch cultures containing sucrose, but they also produce LNFP-I at high titers in fed-batch fermentation processes as shown in the fermentation results below.

Fermentation Results

The production of LNFP-I, LNT, 2'FL and LNT-II is shown as the fraction % of the total HMO produced. A single fermentation was run with the strain MP5, while the fermentations of the strain MP9 were done in duplicate. The fermentation end-point data is presented in Table 5. In general, in the selected fermentation processes, both strains MP5 and MP9 were producing LNFP-I at high levels and similar titers.

Specifically, the strain that cannot grow on sucrose, namely MP5, provided an HMO profile that consisted of 3 HMOs when a glucose-based process (AL-X16) was implemented. In detail, the HMO profile of the strain MP5 contains approximately 95% LNFP-I, 1% LNT and 4% 2'-FL (Table 5). The strain expressing sacC_Agal under the control of the PglpF promoter (strain MP9) produced a bit higher amount of 2'-FL compared to the strain MP5 when a sucrose-based process (AL-X17) was implemented. In particular, the HMO profile of the strain MP9 contains approximately 90% LNFP-I, and 10% 2'-FL, but no LNT (Table 5).

TABLE 5

HMO blend composition in total broth sample at fermentation timepoint 89 h. The strain MP5 grows on glucose (process AL-X16) while the strain MP9 (two independent runs) expresses the SacC_Agal enzyme and can thus utilize sucrose as the carbon and/or energy source (process AL-X17).

| Fermentation Batch ID GDF22xxx | Strain | Process ID | LNFP-I/ HMO (%) | 2'-FL/ HMO (%) | LNT/ HMO (%) | LNT-II/ HMO (%) |
|---|---|---|---|---|---|---|
| 240 | MP5 | AL-X16 | 94.9 | 4.2 | 0.9 | 0.0 |
| 243 | MP9 | AL-X17 | 90.5 | 9.5 | 0.0 | 0.0 |
| 244 | MP9 | AL-X17 | 90.3 | 9.7 | 0.0 | 0.0 |

In conclusion, the SacC_Agal sucrose utilization technology enables the high-level LNFP-I production using an accordingly engineered cell, which provides an HMO profile that is highly similar to the one obtained using glucose as the carbon source.

Sequences

The current application contains a sequence listing in text format and electronical format which is hereby incorporated by reference as are the sequences listed in the corrected sequence list in the priority application DK PA 2021 70250. Below is a summary of the sequences which are not presented in Table 4.

SEQ ID NO: 1 [smob protein]
SEQ ID NO: 2 [smob gene]
SEQ ID NO: 3 [bad]
SEQ ID NO: 4 [nec]
SEQ ID NO: 5 [YberC]
SEQ ID NO: 6 [Fred]
SEQ ID NO: 7 [Vag]
SEQ ID NO: 8 [Marc]
SEQ ID NO: 9 [scrY]
SEQ ID NO: 10 [scrA]
SEQ ID NO: 11 [scrB]
SEQ ID NO: 12 [scrR]
SEQ ID NO: 13 [SacC_Agal protein]
SEQ ID NO: 14 [Bff protein]
SEQ ID NO: 40 [IgtA]
SEQ ID NO: 41 [GalTK]
SEQ ID NO: 42 [GlpR]

The invention claimed is:

1. A genetically engineered cell capable of producing lacto-N-fucopentaose I (LNFP-I) comprising a recombinant nucleic acid sequence encoding an α-1,2-fucosyltransferase protein comprising SEQ ID NO: 1, or a functional homologue thereof having an amino acid sequence which is at least 90% identical to SEQ ID NO: 1, wherein the α-1,2-fucosyl-transferase is capable of transferring of a fucosyl moiety from a donor molecule onto a galactose moiety of lacto-N-tetraose (LNT) through an α-1,2 coupling.

2. The genetically engineered cell according to claim 1, wherein the predominant fucosylated human milk oligosaccharide (HMO) produced by the cell is LNFP-I.

3. The genetically engineered cell according to claim 1, wherein the cell further comprises a nucleic acid sequence encoding a β-1,3-N-acetyl-glucosaminyltransferase protein and a β-1,3-galactosyltransferase protein.

4. The genetically engineered cell according to claim 1, further comprising a recombinant nucleic acid sequence encoding the major facilitator superfamily (MFS) transporter protein Nec comprising SEQ ID NO: 4 or YberC comprising SEQ ID NO: 5, or a functional homologue thereof having an amino acid sequence which is at least 90% identical to any one of SEQ ID NOs: 4 or 5.

5. The genetically engineered cell according to claim 1, wherein the cell is selected from the group consisting of *Escherichia coli, Corynebacterium glutamicum, Lactococcus lactis, Bacillus subtilis, Streptomyces lividans, Pichia pastoris*, and *Saccaromyces cerevisiae.*

6. The genetically engineered cell according to claim 1, wherein the expression of the recombinant nucleic acid is regulated by a promoter sequence selected from the group consisting of SEQ ID NO: 16-38 and 39.

7. The genetically engineered cell according to claim 6, wherein the promoter sequence is selected from the group consisting of SEQ ID NO: 27, 22, 28, 29, 30, 32, 33, 34, 37, 38, or 39.

8. The genetically engineered cell according to claim 5, wherein the genetically engineered cell is capable of utilizing sucrose as sole carbon and energy source.

9. The genetically engineered cell according to claim 8, wherein the genetically engineered cell utilizes sucrose by expressing a polypeptide capable of hydrolyzing sucrose into fructose and glucose selected from the group consisting of the SEQ ID NOs: 13 or 14, or a functional homologue thereof having an amino acid sequence which is at least 90% identical to any one of SEQ ID NOs: 13 or 14.

10. A nucleic acid construct comprising a recombinant nucleic acid sequence which is at least 85% identical to SEQ ID NO: 2, wherein the expression of the nucleic acid construct is regulated by a promoter sequence selected from the group consisting SEQ ID NO: 16-38 and 39.

11. A method for producing one or more fucosylated human milk oligosaccharides (HMOs), the method comprising the steps of, a. providing a genetically engineered cell of claim 9, b. culturing the cell in a suitable cell culture medium to express; and c. harvesting one or more fucosylated HMOs produced.

12. The method according to claim 11, wherein the one or more fucosylated HMOs are selected from the group consisting of 2'-fucosyllactose (2'-FL), lacto-N-fucopentaose I (LNFP-I), difucosyllactose (DFL) and lacto-N-difucohexaose I (LNDFH-I).

13. The method according to claim 11, wherein the method predominantly produces LNFP-1.

14. The method according to claim 11, wherein the one or more fucosylated HMOs comprise LNFP-I and 2'-FL, and wherein the method produces a molar ratio of LNFP-I: 2'-FL in the harvested HMOs in step c) in the range of 20:1-2:1.

15. The method according to claim 11, wherein the one or more fucosylated HMOs comprise LNFP-I, and wherein the method produces a molar ratio of LNFP-I: LNT in the harvested HMOs in step c), in the range of 1000:1 to 10:1.

16. The method according to claim 11, wherein the genetically engineered cell comprises a heterologous nucleotide sequence encoding a heterologous polypeptide capable of hydrolyzing sucrose into fructose and glucose which enables utilization of sucrose as sole carbon and energy source of said genetically engineered cell, and wherein the polypeptide capable of hydrolyzing sucrose into fructose and glucose is SacC Agal comprising SEQ ID NO: 13 or Bff of SEQ ID NO: 14, or a functional homologue thereof having an amino acid sequence which is at least 90% identical to any one of SEQ ID NOs: 13 or 14.

17. The method according to claim 11, wherein the genetically engineered cell is cultured in sucrose as sole carbon and energy source.

18. The method according to claim 11, wherein the genetically engineered cell comprises a heterologous nucleotide sequence encoding a major facilitator superfamily (MFS) transporter protein selected from Nec comprising SEQ ID NO: 4 and YberC comprising SEQ ID NO: 5, or a functional homologue thereof having an amino acid sequence which is at least 90% identical to any one of SEQ ID NOs: 4 or 5.

19. The method of claim 11, wherein the one or more fucosylated HMOs harvested in step (c) are further purified to a degree that the one or more HMOs can be used as a food ingredient.

* * * * *